US011250621B2

(12) United States Patent
Tran

(10) Patent No.: US 11,250,621 B2
(45) Date of Patent: Feb. 15, 2022

(54) REALITY SYSTEMS

(71) Applicant: Bao Tran, Saratoga, CA (US)

(72) Inventor: Bao Tran, Saratoga, CA (US)

(\*) Notice: Subject to any disclaimer, the term of this patent is extended or adjusted under 35 U.S.C. 154(b) by 0 days.

(21) Appl. No.: 17/114,832

(22) Filed: Dec. 8, 2020

(65) Prior Publication Data

US 2021/0125405 A1 Apr. 29, 2021

Related U.S. Application Data

(63) Continuation of application No. 16/868,063, filed on May 6, 2020, now Pat. No. 10,891,785, which is a continuation of application No. 16/361,141, filed on Mar. 21, 2019, now Pat. No. 10,685,481, which is a continuation of application No. 15/795,252, filed on Oct. 26, 2017, now Pat. No. 10,282,914.

(51) Int. Cl.
| | |
|---|---|
| *G06T 17/00* | (2006.01) |
| *G06T 19/00* | (2011.01) |
| *A61B 5/11* | (2006.01) |
| *A61B 5/00* | (2006.01) |
| *A61B 5/107* | (2006.01) |
| *G06T 11/00* | (2006.01) |
| *G06T 3/00* | (2006.01) |
| *G06T 19/20* | (2011.01) |
| *A61B 5/0205* | (2006.01) |
| *G01G 19/44* | (2006.01) |
| *A61B 5/16* | (2006.01) |
| *A61B 5/103* | (2006.01) |
| *G06Q 30/06* | (2012.01) |
| *G06T 7/20* | (2017.01) |

(52) U.S. Cl.
CPC .......... *G06T 17/00* (2013.01); *A61B 5/0205* (2013.01); *A61B 5/1036* (2013.01); *A61B 5/1079* (2013.01); *A61B 5/1112* (2013.01); *A61B 5/1118* (2013.01); *A61B 5/1128* (2013.01); *A61B 5/165* (2013.01); *A61B 5/6829* (2013.01); *A61B 5/6898* (2013.01); *A61B 5/742* (2013.01); *G01G 19/44* (2013.01); *G06Q 30/0643* (2013.01); *G06T 3/0093* (2013.01); *G06T 7/20* (2013.01); *G06T 11/001* (2013.01); *G06T 19/006* (2013.01); *G06T 19/20* (2013.01); *A61B 2576/02* (2013.01); *A63B 2220/00* (2013.01); *G06T 2215/16* (2013.01); *G06T 2219/2012* (2013.01)

(58) Field of Classification Search
None
See application file for complete search history.

(56) References Cited

U.S. PATENT DOCUMENTS

| | | | | |
|---|---|---|---|---|
| 10,282,914 B1 * | 5/2019 | Tran | ...................... | A61B 5/1128 |
| 10,685,481 B2 * | 6/2020 | Tran | ...................... | A61B 5/1112 |
| 10,891,785 B2 * | 1/2021 | Tran | ...................... | A61B 5/1079 |
| 2007/0130020 A1 * | 6/2007 | Paolini | ............... | G06Q 30/0621 |
| | | | | 705/26.62 |

(Continued)

*Primary Examiner* — Eileen M Adams
(74) *Attorney, Agent, or Firm* — Tran & Associates

(57) ABSTRACT

Systems and methods are disclosed method for rendering reality for an object by performing motion tracking and area learning of an environment; selecting a pattern or color from a plurality of product variations; blending the pattern or color of the object and the environment; and displaying the color on the object as an augmented reality view.

20 Claims, 16 Drawing Sheets

Place foot adjacent an object (coin or grid) with known dimensions (10)
Take multiple images or videos of the foot and object (12)
Determine dimensions of points of interest on the foot based on object size (14)
Select a standard foot template (16)
Morph/Warp the standard foot template to match points of interest (18)
Select shoe or footwear with interior best matching the morphed foot template (20)

(56) References Cited

U.S. PATENT DOCUMENTS

| | | | |
|---|---|---|---|
| 2008/0128498 A1* | 6/2008 | Fausak | G06Q 10/087 235/385 |
| 2010/0111370 A1* | 5/2010 | Black | G06T 7/75 382/111 |
| 2013/0249947 A1* | 9/2013 | Reitan | G06F 3/011 345/633 |
| 2014/0020192 A1* | 1/2014 | Jones | B33Y 10/00 12/146 B |
| 2016/0015152 A1* | 1/2016 | Ajiki | G06K 9/00288 132/200 |

* cited by examiner

Place foot adjacent an object (coin or grid) with known dimensions (10)

Take multiple images or videos of the foot and object (12)

Determine dimensions of points of interest on the foot based on object size (14)

Select a standard foot template (16)

Morph/Warp the standard foot template to match points of interest (18)

Select shoe or footwear with interior best matching the morphed foot template (20)

FIG. 1A

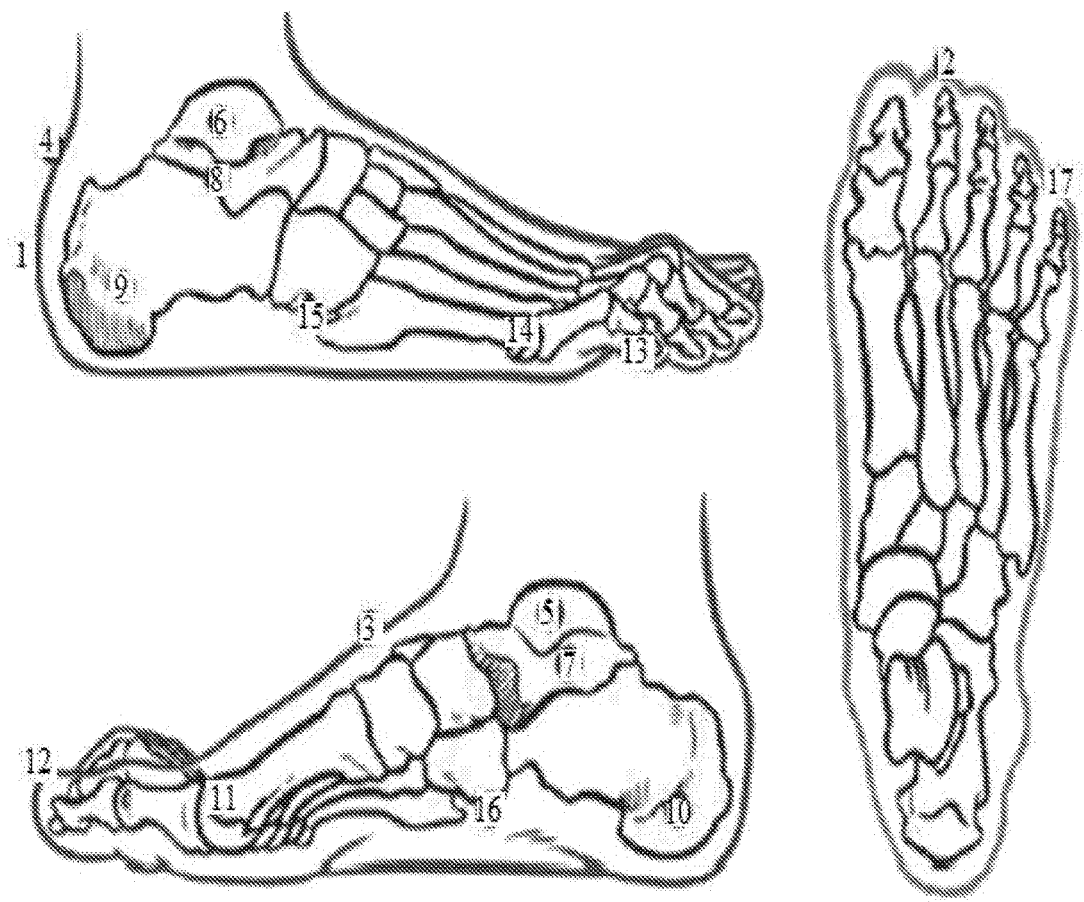

FIG. 1B

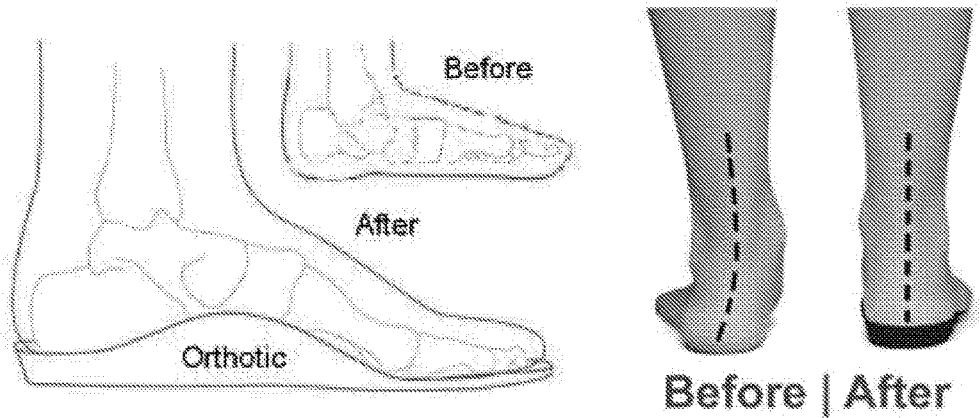

FIG. 10

Place body adjacent an object with known dimensions (40)
Take multiple images or videos of the body and object (42)
Apply photogrammetry to create 3D model of the body (44)
Optionally select a standard body template and Morph/Warp the standard body template to match 3D body model (46)
Select best fitting wearable item or apparel (48)

FIG. 2

Scan a bar code or insignia with a makeup product to retrieve color characteristics of the makeup product (220)
Analyze skin pigment from 2D or 3D model of user's face and/or head (222)
Receive a sequence of hand gestures and postures as well as the use of touch and stylus forming a virtual make-up session and apply the color of the makeup product to user skin tone (224)
Apply virtual make-up features to the 2D or 3D model, to yield a 3D make-up model, based on said received hand gestures and postures (226)

FIG. 3B

FIG. 4A
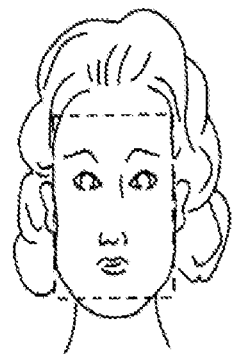
FIG. 4B
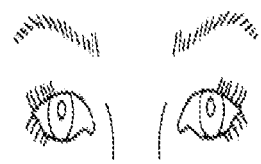
FIG. 5A
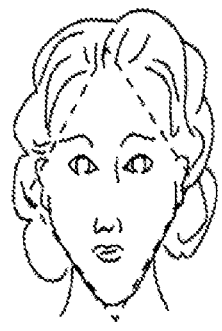
FIG. 4I
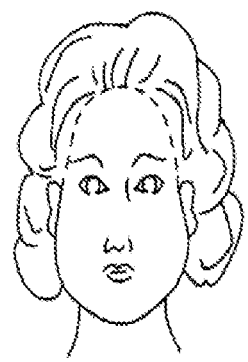
FIG. 4C
FIG. 4D
FIG. 5B
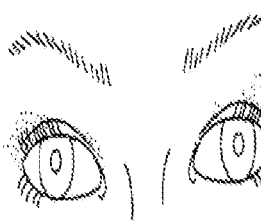
FIG. 5C
FIG. 4E
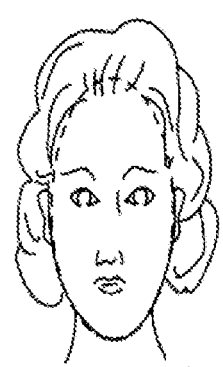
FIG. 4H
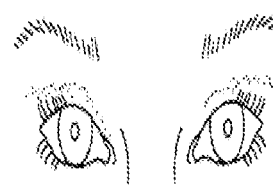
FIG. 5D
FIG. 4F
FIG. 4G
FIG. 5E Capture 3D model of clothed body (310)

Digitally remove current dress (312)

Select new fashion styles from new trends (314)

Morph or project clothing onto the 3D model of body (316)

Allow user to iterative change fashion color, length until satisfied with new clothing (318)

Allow user to select from a library of jewelry and shoes to provide realistic simulation (320)

Order desired clothing with custom measurements (322)

FIG. 8A

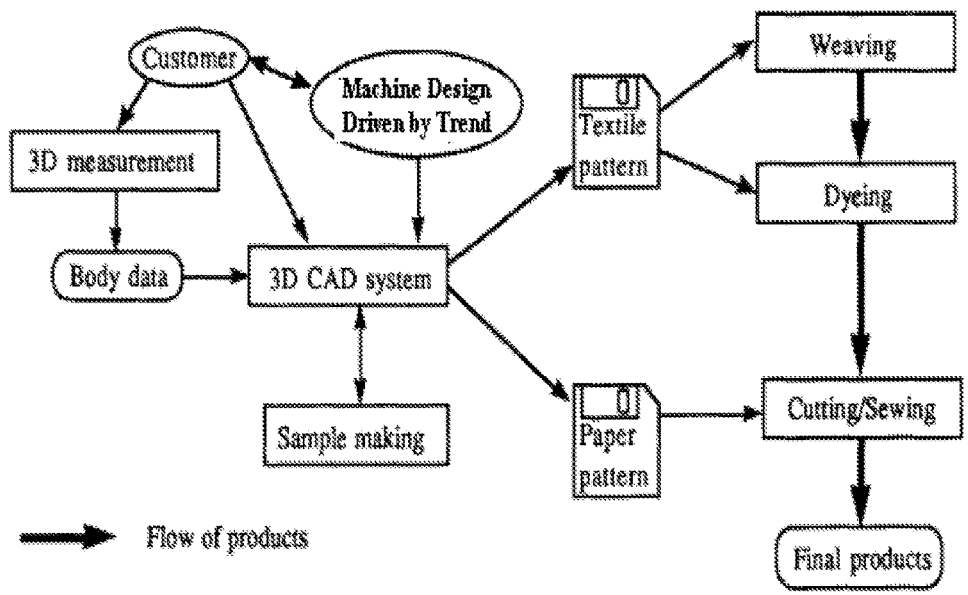

FIG. 8C

Capture 3D model of head (350)

Remove current hair (352)

Select hair styles from new trends (354)

Morph or project hair onto the 3D model of head (356)

Allow user to iterative change hair styling until satisfied with new hairdo (358)

Allow user to select from a library of wardrobes to provide realistic simulation (360)

Share desired hair style with professional to achieve desired hairdo (362)

FIG. 9A

Capture 3D model of products including furniture/appliance (370)

Capture target space (372)

Move or remove current product as desired (374)

Select new product and retrieve (376)

Morph or project product into the target space (378)

Allow user to iterative change product position until satisfied (380)

Allow user to select from a library of additional products to provide realistic simulation (382)

Purchase product (384)

FIG. 9B

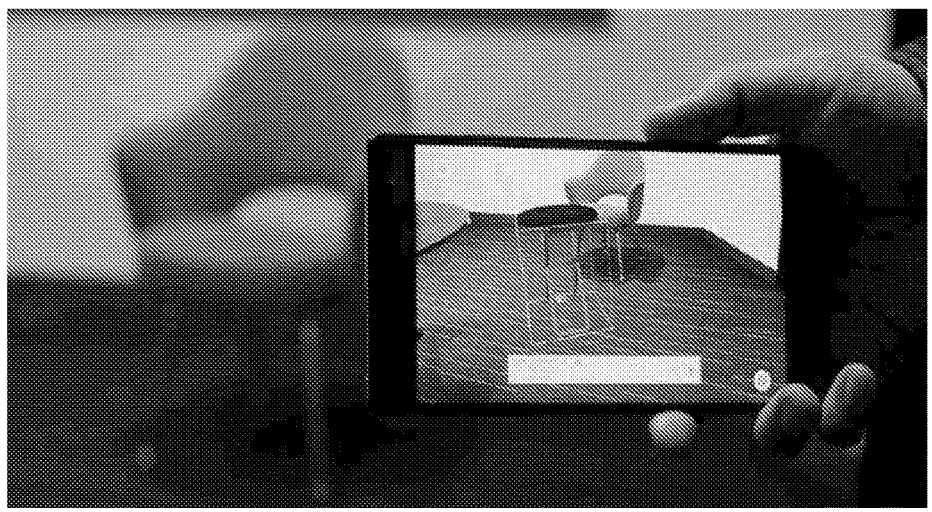

FIG. 9C

Capture 3D model of user (370)

Isolate breast or butt region (372)

Model shape and size of breast or butt increase due to implant (374)

Morph or project the shape/size of breast or butt increase onto the 3D model of user (376)

Allow user to iterative change breast/butt shapes/sizes until satisfied with new shape (378)

Allow user to select from a library of wardrobes to provide realistic simulation (380)

Send desired shape and provide feedback to plastic surgeon to implement desired shape and size (382)

FIG. 10

REALITY SYSTEMS

The present invention provides a method for fitting product.

BACKGROUND

In fields such as surgery, clothing, footwear, and 3D printing, among others, needs exists for a method to capture the anatomy in the world and either reproduce them with a 3D printer, share, or virtually operate on the anatomical 3D model. Existing system to scan the user in three dimensions require specialized hardware. For example, some systems can create an estimate of the depth of a body by simultaneously acquiring images with multiple image capture devices, by using a known and structured light source, by using a laser solution, or some combination thereof. This creates additional expenses and software requirements for the user.

SUMMARY

In one aspect, systems and methods are disclosed for fitting a subject by generating one or more 3D deformable models for an anatomical portion; capturing images of a user anatomical portion and a reference object using a mobile camera; generating an updated model of the user anatomical portion by selecting a closest 3D deformable model to the user anatomical portion and matching points on the closest 3D deformable model to one or more predetermined points on the user anatomical portion; and selecting a best-fit product from a plurality of product variations based on the 3D model.

In another aspect, a method for selecting a product includes selecting one or more 3D models from a product database; capturing images of a user view of a location and a reference frame using a mobile camera; generating an updated model of the location by selecting a closest 3D product model to the user view and matching points on the closest 3D product model to one or more predetermined points on the user view; and selecting a best-fit product from a plurality of product variations based on the 3D model.

In a further aspect, a method for fitting includes selecting one or more 3D models from a product database; capturing images of a user view relative to a reference frame using a mobile camera with a wide angle lens and an infrared sensor; determining dimensions for the user view by motion tracking, area learning, and depth sensing of objects in the user view; generating an updated model of the user view by selecting a closest 3D model to the user view and matching points on the closest 3D product model to one or more predetermined points on the user view; and selecting a best-fit product from a plurality of product variations based on the 3D model.

In another aspect, a smart mirror provides relevant information to a user to prepare him/her for daily tasks. The smart mirror overlays a graphical user interface over a partially reflective glass. The user interface can provide news, traffic and weather information, emails, social network communications. The smart mirror can act on the user's verbal requests or gestures. A mirror gesture control system includes a plurality of cameras mounted proximal to the mirror to detect edges of an object; and a processor to translate the edges as mouse movement and mouse clicks to control the vehicle by moving hands.

In another aspect, a camera tracks movements and a 3-D scanner analyzes the viewer's physique. Body recognition software analyzes the body shape to determine weight loss or gain. In addition to shoe/clothing suggestions, the system can provide clothing/jewelry/hair styling suggestions along with augmented reality view of the suggestions so that the user can visualize the impact of the clothing or jewelry or styling. Facial recognition software inspects the face shape to determine health. The smart mirror can provide make-up suggestions along with augmented reality view of the applied suggestions so that the user can visualize the impact of the makeup. The smart mirror can provide non-surgical body augmentation suggestions such as breast/buttock augmentations along with augmented reality view of the body enlargements or size reduction so that the user can visualize the impact of the footwear or apparel when worn, along with body enhancement, clothing or jewelry or hair styling changes.

In yet another aspect, built-in sensors in combination with mobile phone usage pattern and social network communications can detect signs of stress and other mental/emotional health states of the user. The smart insole or shoes with sensors could also be combined with other health-related apps to keep track of calorie count, vital signs, fitness level and sleep quality. By extrapolating from the user's current behaviors, vitals and bone and muscle structure, the augmented-reality mirror can forecast the user's future health. The camera can measure breathing activity and/or heart rate of the user in front of the mirror or alternatively the system can bounce WiFi off the chest to detect breathing activity. The mirror highlights hard-to-see changes in the body, such as increased fatigue, minute metabolic imbalances and more. A DNA analyzer can receive swipes from tongue, ear, and saliva, bodily fluids to capture genetic data at a high frequency and such data can be correlated with the fitness wearable devices for signs of health problems. Additionally, the data can be analyzed at a metropolitan level for public health purposes.

Advantages may include one or more of the following. The system provides convenience and time efficiency when selecting products online. The system reduces product returns due to unexpected size differences with the user's anatomy. As today's habits shape future health, the 3D model of the body can be used to encourage users to take healthy actions. The system can continually monitor health and proactively report any changes before they get serious. The body sensor camera provides people with more "granular" health data that may otherwise be undetected until their yearly checkups. When these effects are considered in aggregate, one or more of the methodologies described herein may obviate a need for certain efforts or resources that otherwise would be involved in convenience to the user. Efforts expended by user or provider of fashion products may be reduced by one or more of the methodologies described herein. Computing resources used by one or more machines, databases, or devices may similarly be reduced. Examples of such computing resources include processor cycles, network traffic, memory usage, data storage capacity, power consumption, and cooling capacity.

BRIEF DESCRIPTION OF THE FIGURES

FIG. 1A shows an exemplary process for creating a 3D model of a body portion such as a foot.

FIG. 1B shows exemplary anatomical points on the foot.

FIG. 1O shows exemplary orthotic insole or sole produced using the above system.

FIG. 2 shows another exemplary process for creating a 3D model of the body.

FIG. 3A shows an exemplary user interface on the phone for virtually testing the make-up products prior to order, while FIG. 3B shows an exemplary method for testing make up techniques and/or make-up products.

FIGS. 4A-4I illustrate representations of representing eight of the classic facial configurations.

FIGS. 5A-5E illustrate various computer recommendation on eye-formations.

FIG. 8A shows an exemplary process for suggesting styles for the user.

FIG. 8C shows a mass-customized clothing fabrication network that is driven by current fashion and hot celebrity trends.

FIG. 9 shows an exemplary hair style suggestion process.

FIG. 10 shows an exemplary medical cosmetic suggestion process with the 3D body model.

DESCRIPTION

Figure 1C:
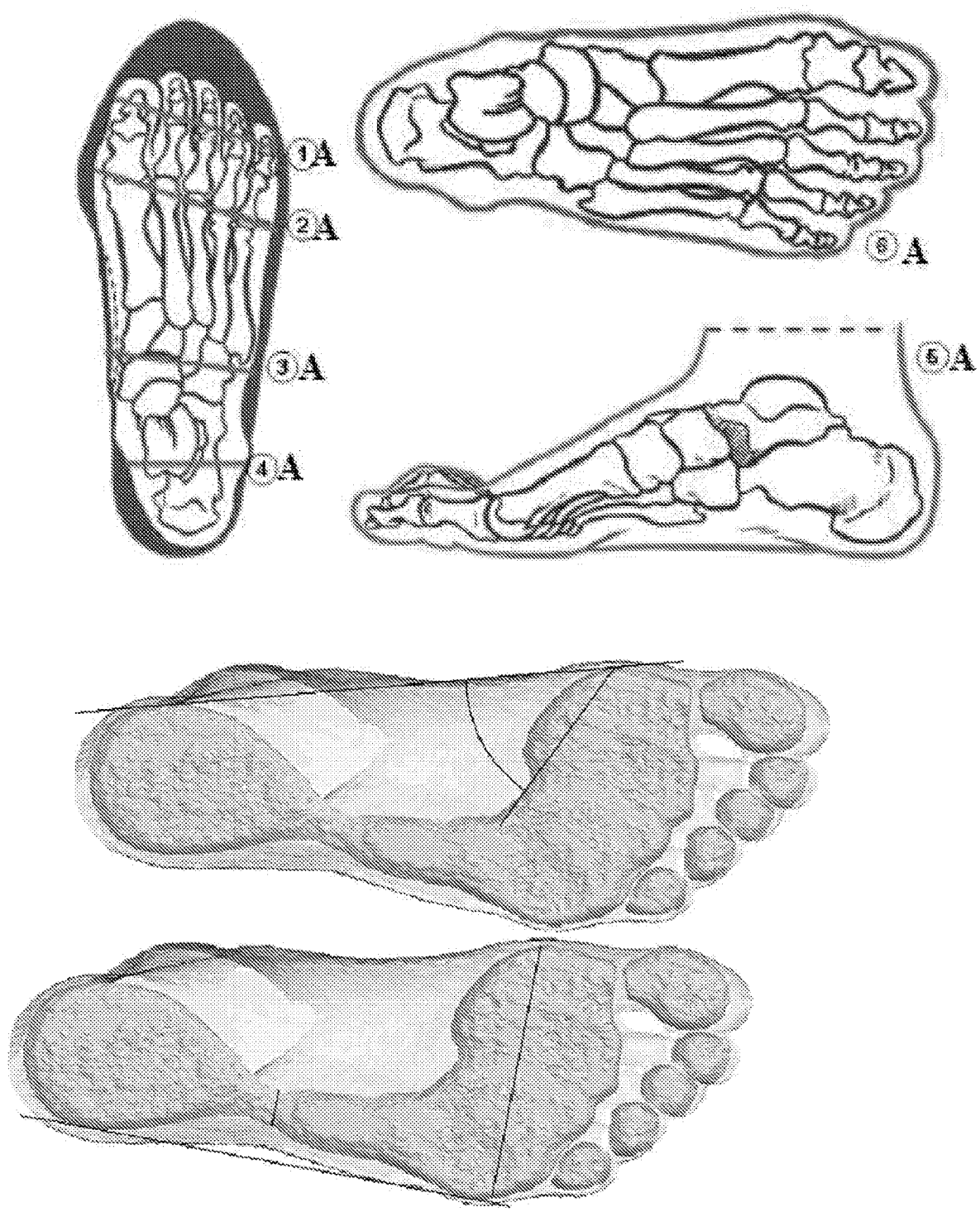
FIG. 1C shows shoe matching based on key sections and girths of the foot.

As used in this document, the singular forms "a," "an," and "the" include plural references unless the context clearly dictates otherwise. Unless defined otherwise, all technical and scientific terms used herein have the same meanings as commonly understood by one of ordinary skill in the art. As used in this document, the term "comprising" means "including, but not limited to."

Deformable 3D Master Models of Body Portions

First, the process forms a set of deformable models of the body such as the face, hand, or foot models. The deformable 3D master model is subsequently match to the user's body simply by matching reference points. In various embodiments, the deformable models can be done by sex, weight or by disease classification, for example.

In one embodiment for foot products, an initial set of feet is scanned using a smart phone, a camera, or a combination of camera and infrared laser/camera, and the points are used in constructing a library of deformable 3D model of feet. The library of deformable 3D models are created and matched to images of the feet through deformations to the points of interest to precisely match the user's actual feet. A physically accurate 3D model can be created therefrom without significant storage of the 3D points and the 3D model of the user can be done using minimal computation resources. The 3D models of feet allow new feet to be customized to a particular 3D template, thus avoiding storage requirements of millions or billions of 3D models of feet. To enhance accuracy, instead of one model for everyone, a plurality of deformable master models can be formed for each of discrete sizes such as US sizes 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, and 18, for example.

The morphable or deformable foot model can be generated from a set of unregistered 3D foot model. The process computes a dense point-to-point correspondence between the vertices of the foot. The process finds the best match of a given foot only within the range of the morphable model. To determine residual deviations between a new foot and the best match within the model, as well as to set unregistered prototypes in correspondence, in one embodiment the process uses an optic flow method that computes correspondence between two feet without the need of a morphable model.

Constructing a deformable or morphable foot model from a set of unregistered 3D scans is done through a computation of the flow fields between each foot and an arbitrary reference foot. Given a definition of shape and texture vectors for the reference face to each face in the database can be obtained by means of the point-to-point correspondence provided by feet in the database.

A recursive process for enhancing the deformable foot model is described next. The process finds rough correspondences to the new foot using the (inadequate) morphable model and then improves these correspondences by using an optic flow method. Starting from an arbitrary foot as a temporary reference, preliminary correspondence between all other feet and this reference is computed using the optic flow algorithm. On the basis of these correspondences, shape and texture vectors can be computed. To handle noise, each deformable model is run through a plurality of foot scans, and if the same correspondences appear, they are used and correspondences from noisy data are discarded. Alternatively, their average serves as a new reference foot. The first morphable model is then formed by the most significant components as provided by a PCA decomposition. The current morphable model is now matched to each of the 3D feet according and the optic flow method computes correspondence between the 3D foot and the approximation provided by the morphable model. Combined with the correspondence implied by the matched model, this defines a new correspondence between the reference foot and the example. Iterating this procedure with increasing expressive power of the model (by increasing the number of principal components) leads to reliable correspondences between the reference foot and the examples, and finally to a complete morphable foot model.

Another embodiment determines a 3D Correspondence using Optic Flow and finds corresponding points in grey-level images and a gradient-based optic flow method to establish correspondence between a pair of 3D scans, taking into account color and radius values simultaneously. The algorithm computes a flow field that minimizes differences of in a norm that weights variations in texture and shape equally. Surface properties from differential geometry, such as mean curvature, may be used as additional components. On foot regions with little structure in texture and shape, the results of the optic flow method are sometimes spurious. A smooth interpolation is done based on simulated relaxation of a system of flow vectors that are coupled with their neighbors. The quadratic coupling potential is equal for all flow vectors. On high-contrast areas, components of flow vectors orthogonal to edges are bound to the result of the previous optic flow computation. The system is otherwise free to take on a smooth minimum-energy arrangement. Unlike simple filtering routines, the technique fully retains matching quality wherever the flow field is reliable. Optic flow and smooth interpolation are computed on several consecutive levels of resolution.

In one embodiment, the closest deformable model is selected to match to a new foot. The selection of the closest model can be done based on size or a suitable attribute such as weight or disease, for example. The closest deformable model is then selected to be matched to the new foot. The method transfers foot motion vectors from a source foot model to a target user model having different geometric proportions and mesh structure (vertex number and connectivity). Using an automated heuristic correspondence search, the system can select fewer than ten points in the model to match to a new scan. The method allows new 3D foot scans to be easily retargeted to a library of foot templates or models.

A similar process can be used to create deformable face models, hand models, stomach models, ear models, breast models, and buttock models for cosmetic and health purposes.

3D Models of Subjects Using Phone Cameras

FIG. 1A shows an exemplary process for creating a 3D model of a body portion such as a foot. First, the body portion such as a foot is placed adjacent an object (coin or grid) with known dimensions (20). For example, an A4 sheet of paper can provide known dimensions to scale to the foot. Similarly, a quarter coin can provide known thickness and diameter dimensions used to scale the image. Alternatively, paper with grids imprinted thereon can be used to provide reference dimensions.

The system then takes multiple images or videos of the foot and object (22). In one embodiment, the user can simply use a smart phone directly create the 3D model in the phone or upload the images to a server for processing. Next, the system can determine dimensions of points of interest on the foot based on object size (24). For example, FIG. 1B shows exemplary points of interest including anatomical Points: (1) Rearest point of the Heel (2) Most advenced point of the 2nd Toe (3) Point of the Instep (4) Insertion of Achille's tendon in Calcaneus (5) Most prominent point of the internal malleolus (6) Most prominent point of the external malleolus (7) Below internal malleolus (8) Below external malleolus (9) Most prominent point of the external heel (10) Most prominent point of the internal heel (11) Most prominent point of the head of the 1st metatarsal (12) Highest point of the 1st toe (13) Most lateral point of the 5th toe (14) Most prominent point of the 5th metatarsal (15) Styloid-apophysis of the 5th metatarsal (16) Lowest point of Navicular (17) Forest point of the 5th toe.

Turning back to FIG. 1A, the process selects a standard foot template (26) and morph/warps the standard foot template to match points of interest (28), and then selects a footwear or a shoe with interior best matching the morphed foot template (30). For example, in FIG. 1C, the matching to the footwear or shoe can be based on key sections and girths of the foot: (1A) Toe Section (2A) Metatarsals Section (3A) Midfoot Section (4A) Heel Section (5A) Profile of the foot (6A) plantar contour. "Footwear" refers to any type of apparel that may be worn on a person's lower body, specifically the feet and optionally also the lower legs. Examples include athletic shoes and other shoes, work boots, ski boots and other boots, sandals, slippers, and any other apparel item designed to be worn on the foot and optionally also the lower leg.

The process can store body dimensions in a computer, a data storage device, cloud storage, or in a separate data storage facility as well as identifying information for a plurality of wearable items and data related to each wearable item. The data can include a set of internal measurements and other fit and performance parameters that may be obtained for each wearable item and imported into the data set such that a two dimensional (2D) or three dimensional (3D) representation of the wearable item may be constructed. The data set also may include feedback about the wearable items as reviewed by multiple consumers, as will be described in more detail below. For example, for a footwear model, the internal measurements can include a total length measurement, a total width measurement, heel width, arch length and arch width. When applicable, additional parameter measurements can also be stored, including, but not limited to, toe box height, forefoot height, and arch height. Three dimensional measurements may be stored within the data set as well, such as toe box girth, forefoot girth, and heel to toe girth. Measurement parameters such as tapering or change in width as a percentage of total length can also be stored within the data set. It should be noted that this list of measured parameters is provided by way of example only, and additional parameters measurements may be included such as heel height, arch height, girth, foot opening diameter, and any other relevant information. In additional to dimensional measurements described above, other parameter measurements may be associated with a footwear model depending on model type. For example, a miming shoe may have feature-based parameter measurements associated with stability whether or not the shoe has motion control, racing spikes, and any other relevant parameters. Tactile measurements such as cushioning, stretch and deformation also may be available for various areas in the footwear model. The system may receive these parameter measurements from one or more scanning devices that scan the footwear model and collect measurement data from the footwear model.

In one embodiment, the user captures images from all angles around the body (such as the foot). When the user finishes scanning the foot, the plurality of images is transferred to a processor. For exemplary purposes, the processor may be on a remote server. A reconstruction and generation operations are performed on the plurality of images. An optimization is performed on the plurality of images to simultaneously determine a pose of the image capture device for each image in the plurality of images, as well as a camera matrix for the image capture device used, the camera calibration matrix or camera intrinsics, as well as one or more radial distortion parameters. The pose of the image capture device includes an X, Y, and Z location in a universal coordinate frame, which describes distances from an origin in a three dimensional coordinate system along three orthogonal basis vectors. The pose of the image capture device also includes a roll, a pitch, and a yaw, which correspond to rigid body rotations about each of the three orthogonal basis vectors. The total pose of the image capture device may be described as $<x, y, z, r, p, q>$, or may also be given as a translation in three dimensions plus a quaternion, or a rotation matrix and translation vector. The camera matrix includes a two-dimensional center point, a focal length in a first axis, and a focal length in a second axis. In addition, one or more radial distortion factors which describes a radial distortion associated with the plurality of images due to a lens used in the image capture device is extracted. As an alternative to a single radial distortion factor expressing, for example a fish-eye lens, a series of coefficients may be extracted which expresses additional radial distortion parameters if the lens model is a polymer. For exemplary purposes, the optimization is a non-linear least squares optimization using a series of points associated with the regular pattern of first shapes and second shapes as determined in every image. In an alternative embodiment, the camera can be equipped with a plurality of sensors. The sensors may include accelerometers, sonar, gyroscopes, magnetometers, laser range finder, and global positioning systems where the surface with the regular pattern of first shapes and second shapes is not required. In the scanning step, sensor data from the plurality of sensors is also acquired between every image captured in the plurality of images. The sensor data is also sent to the processor in the scanning step. In the reconstruction, the optimization is performed not over the series of points associated with the regular pattern of first and second shapes, but features extracted from each image in the plurality of images, as well as the sensor data. A feature conveys data which is unique to the image at a specific pixel location, such as unique image gradients or pixel intensities. For exemplary purposes, features are extracted from the images and can be related to (1) Rearest point of the Heel (2) Most advenced point of the 2nd Toe (3) Point of the Instep (4) Insertion of Achille's tendon in Calcaneus (5) Most prominent point of the internal malleolus (6) Most prominent point of the external malleolus (7) Below internal malleolus (8) Below external malleolus (9) Most prominent point of the external heel (10) Most prominent point of the internal heel (11) Most prominent point of the head of the 1st metatarsal (12) Highest point of the 1st toe (13) Most lateral point of the 5th toe (14) Most prominent point of the 5th metatarsal (15) Styloid-apophysis of the 5th metatarsal (16) Lowest point of Navicular (17) Forest point of the 5th toe. The features can be unique image gradients or pixel intensities or can also be math derivatives using Harris corners, FAST features, FREAK features, SIFT features, ORB features, SURF features, BRISK features, or the like. Codebook of features can be used to map the user anatomy to one of a plurality of deformable or morphable 3D foot models. The process can then selects footwear or a shoe with interior best matching the deformable/morphable foot template key sections and girths of the footwear: (1A) Toe Section (2A) Metatarsals Section (3A) Midfoot Section (4A) Heel Section (5A) Profile of the foot (6A) plantar contour.

Next, the process can form codebooks of foot features. Alternatively, a continuous density model can be used because it avoids any errors that could be introduced in the quantization phase. The codebook approach classifies each frame into one of N categories, each represented by canonical vector that is associated with a symbol in the code book. Once a foot is classified by a codebook, can be represented by a single symbol that indicates which code value it is closest to. Code book vectors are defined by training on a training corpus of feet that minimizes the overall distortion, which is the sum of each input vectors' distance from the code book vector that it is identified with. The process iteratively improves the entire set of code book vectors using a K-means clustering algorithm where, given an initial set of N code book vectors $C_i$ and a set of training vectors, the process performs:

Classification: Cluster the training vectors by its closest code book vector according to a distance function;

Centroid Update: Update each code book vector to be the centroid (relative to the a difference function used) of the training vectors assigned to it.

Iteration: If the improvement in overall distortion is greater than a threshold, then repeat from step 1.

Continuing in the reconstruction, once the pose of the image capture device and the camera matrix is determined for every image in the plurality of images, it is possible to estimate the depth at specific images in the plurality of images using both intensity values contained in the image as well as the image capture device pose for every image. For exemplary purposes, the depth may be acquired by a minimization of an energy defined. The minimum of the energy may be solved for by performing a Legendre-Fenchel transform and expressing the optimization in both a primal and dual variable. By expressing the problem in both the primal and dual forms, it is possible to use a primal-dual hybrid gradient approach to finding the minimum of the energy. Because a primal-dual hybrid gradient is used, the minimum may be determined by performing a primal descent and a dual ascent for every pixel in the image in parallel on a graphics processing unit (GPU). Sequential subsets of the plurality of images are used to form a depth image, wherever a depth image is desired, by first determining the inverse depth for every pixel in the cost volume which maps to the lowest cost. Once a minimum is estimated, a dual ascent is performed in dual step, a primal ascent is performed in a primal step and an update is performed in an update step. In the update step, a similar search through the cost volume is performed as in the depth estimate, however the search is augmented by the difference of the primal variable with the slack variable, squared, divided by twice the mediation variable. The dual step, primal step, and update step are repeated until a stopping criterion is reached. For exemplary purposes, the stopping criterion is reached once the mediation variable is reduced below a threshold or a change in the energy computed is below a certain threshold. Once the stopping criterion is reached, the depth at every pixel calculated is stored in a depth image.

Alternatively, a buffer of a predetermine number of frames is created from a video sequence. If a previous depth image is known (determined via the previous depth estimate or by raycasting a truncated signed distance function storing a fusion of previous depth estimates), the full pose of the image capture device for every image is updated by performing dense tracking using the previous depth estimate, image taken at the previous depth estimate, and a current image. Dense tracking calculates the pose by performing a minimization with respect to the pose of a reprojection error between the previous image, the previous depth, and the current image using every pixel of both images.

Once the cost volume is calculated, a depth per frame is calculated by first performing a minimum search along every inverse depth element for every pixel in the cost volume. This rough depth estimate is then smoothed using a weighted Huber regularizer via the same primal-dual hybrid gradient optimization schema as above. To further increase the accuracy of the depth estimates, the output of the optimization is used to initialize a wide baseline polishing step. In this wide baseline polishing step, a linearization of reprojection errors from the reference image of four additional frames further from the reference frame than the 20 frame selected subset, but within 80 cm of the reference frame, is regularized with a similar weighted Huber regularizer and minimized using a primal-dual hybrid gradient approach yielding a depth image. All of the depth images form a series of depth images. Since the pose of the device is known relative to the surface, it is possible to remove all information from the depth image that is at or below the surface. This leaves only the foot object in an updated depth image. The series of updated depth images may be stored in a volumetric representation of depth. For exemplary purposes, the volumetric representation of depth is a signed distance function. Each depth image is then loaded into the signed distance function representation. A model is formed using the volumetric representation of depth and stored in a model file. For exemplary purposes, the model file is a mesh. Further, it is contemplated that the model file is created from the volumetric representation of depth. One such volumetric representation of depth is a signed distance function. Alternatively, a truncated signed distance function may be used. Once every image is acquired, it is fused into the signed distance function. The model file may be extracted from a signed distance functions by such algorithms as marching cubes, marching tetrahedral, or Poisson reconstructions.

Although the foregoing discusses phone based cameras, other consumer cameras that work with a desktop computer can be used. In one embodiment the Microsoft Kinect camera can be used, while in another embodiment, a 3D camera such as the Intel RealSense uses three components: a conventional camera, a near infrared image sensor and an infrared laser projector. Infrared parts are used to calculate the distance between objects, but also to separate objects on different planes. In one embodiment, a processor to translate the edges as mouse movement and mouse clicks to control the vehicle by moving hands. They serve for facial recognition as well as gestures tracking. The Intel 3D camera can scan the environment from 0.2 m to 1.2 m. Its lens has a built in IR cut filter. The video camera has a frame rate up to 60 fps with a 90° FOV, moreover its lens has an IR Band Pass filter. The IR laser integrates an infrared laser diode, low power class 1, and a resonant micro-mirror. The 3D camera can provide skeletal and depth tracking and may gather spatial data that describes objects located in the physical environment external to the depth sensor (e.g., the user's bath room). The skeletal and depth tracking technology may be implemented in a depth sensor (e.g., the Kinect, the Intel Realsense), stereo cameras, mobile devices, and any other device that may capture depth data. In some example embodiments, the skeletal and depth tracking technology is implemented on a server using algorithms that utilize the RGB and depth channels. In some example embodiments, depth sensing technologies use structured light or time of flight based sensing. For example, an infrared (hereinafter, also "IR") emitter that is part of the preference analysis machine 310 and that is located in the user's living room, may project (e.g., emit or spray out) beams of infrared light into surrounding space. The projected beams of IR light may hit and reflect off objects that are located in their path (e.g., the user or a physical object in the user's living room). A depth sensor (e.g., located in the user's living room) may capture (e.g., receive) spatial data about the surroundings of the depth sensor based on the reflected beams of IR light. In some example embodiments, the captured spatial data may be used to create (e.g., represent, model, or define) a 3D field of view that may be displayed on a screen (e.g., of a TV set, computer, or mobile device). Examples of such spatial data include the location and shape of the objects within the room where the spatial sensor is located. In some example embodiments, based on measuring how long it takes the beams of IR light to reflect off objects they encounter in their path and be captured by the depth sensor, the preference analysis machine may determine the location (e.g., the distance from the depth sensor) of the objects off which the beams of IR light reflected (e.g., the user, a furniture piece, or a wall). In various example embodiments, based on the received spatial data, the system may determine details of the objects in the room, such as spatial measurements of the objects in the room (e.g., the dimensions of the user's body). The camera determines one or more measurements (e.g., dimensions) of the body of the user as part of the analysis of the image and the model. The processor with 3D model information from the user may also determine, based on the measurements of the user's body, one or more sizes of fashion items from different brands (e.g., manufacturers or sellers of fashion items) that may fit the user's body.

One embodiment for clothing includes obtaining a 3D model of a user standing in front of the display and rendering one or more articles or products on the 3D model. Images such as photographs or videos can be made of the user (also referred to as customer or client) when trying on different articles. These images can be seen on the display and can simply be ordered/edited/deleted by the user by "dragging" them across the screen. In this example, the display is designed as a touch screen. In this manner, the articles tried on can be compared more realistically and more easily by the user.

Footprint for Authentication or Identification

Figure 1D:
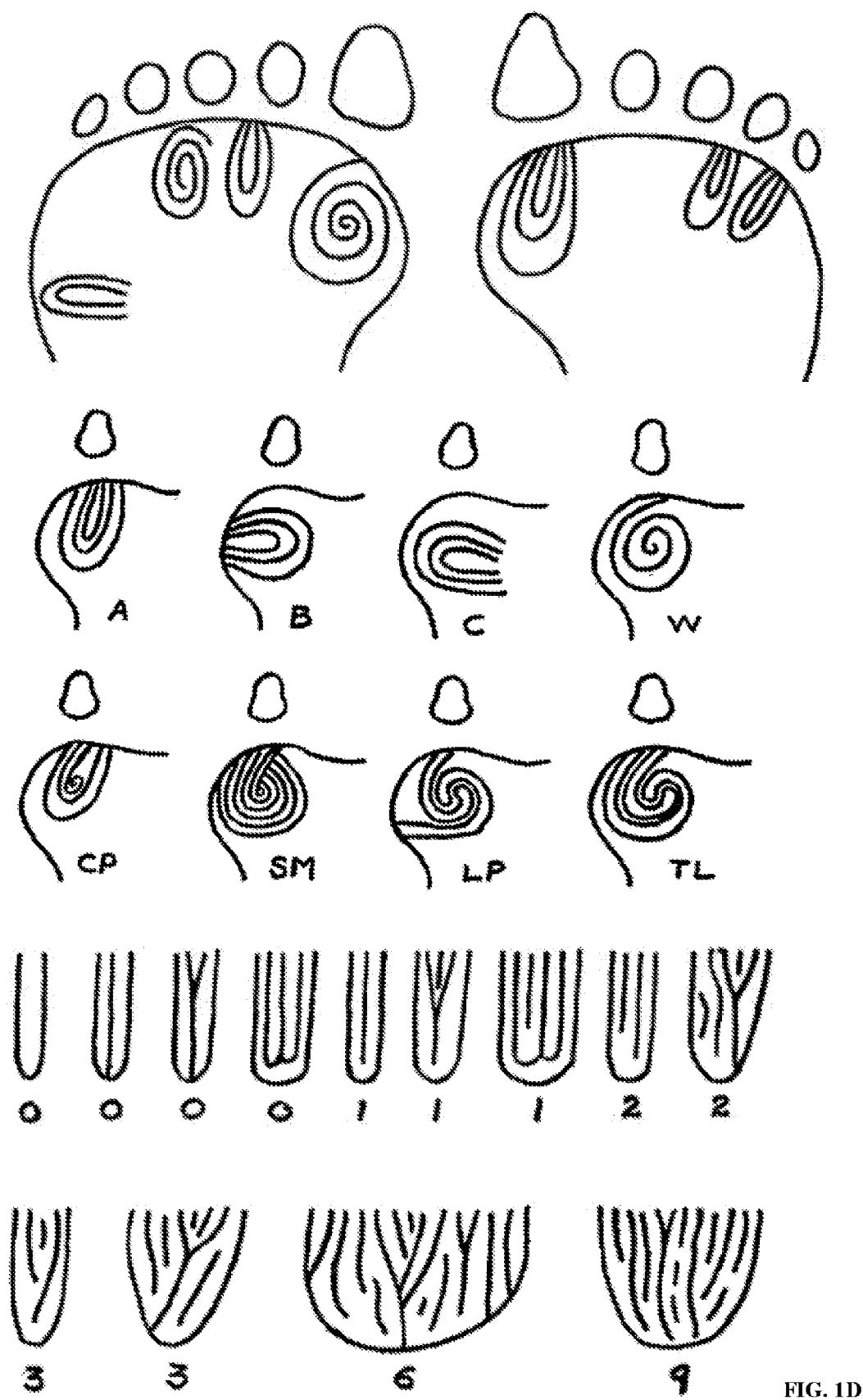
FIG. 1D shows an exemplary process for determining back foot features.

FIG. 1D shows an exemplary system for identifying people based on foot prints. The top of FIG. 1D shows exemplary left and right foot print regions that are analyzed to uniquely determine a person for authentication, ecommerce as part of a multi-factor authentication, baby identification, or criminology purposes, among others. FIG. 1D next shows exemplary hallucal area patterns near the big toe, while the bottom of FIG. 1D shows ridge counts and shape at the core of the patterns. The numbers in each case indicate the count for each pattern. On the ball of the foot there are five pattern bearing areas. One is proximal to the great toe (the hallucal); three others lie lateral to the hallucal, below the small toes, and together form the plantar area; and the fifth, or hypothenar, is located on the lateral edge of the sole proximal to the third plantar area. The first plantar area lies nearest the hallucal. Here we find the open field (0), the upright loop opening distally (U), the inverted loop opening proximally (U), and the whorl (W). The hypothenar area contains principally loops (U), rarely a whorl or an arch. These five areas may be likened to the five finger tips.

Figure 1E:
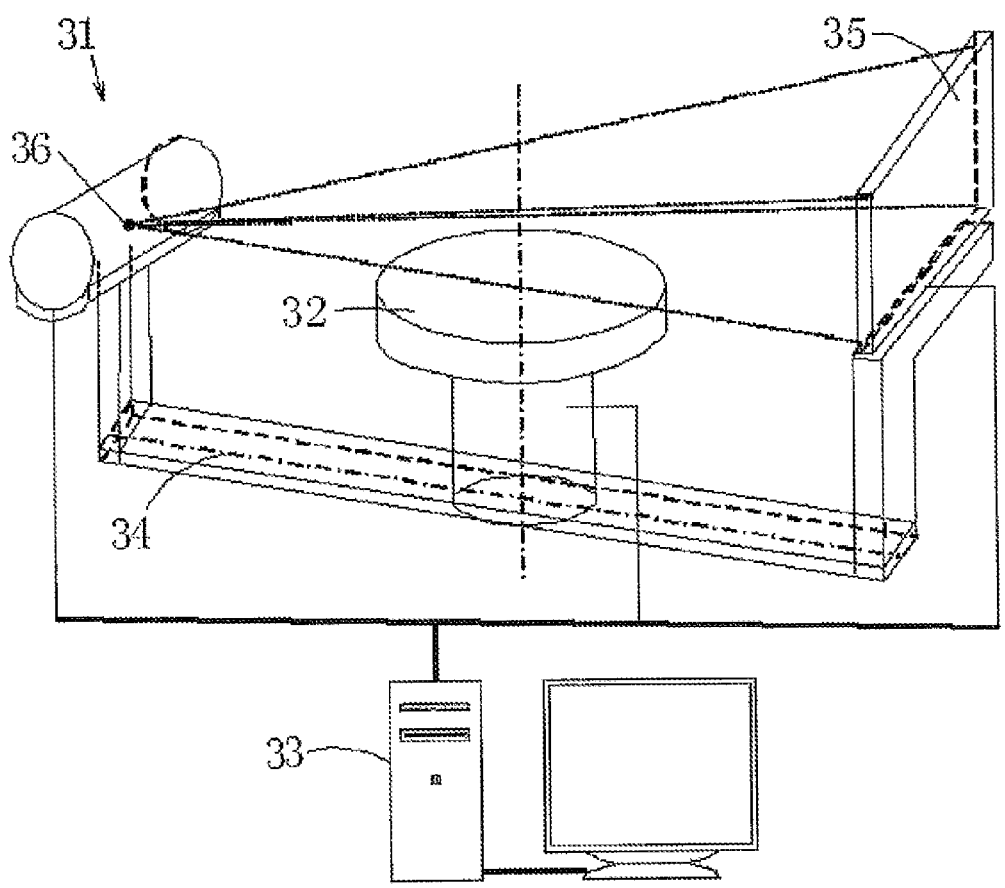
FIG. 1E shows an exemplary shoe scanner for scanning interior dimensions of shoes/footwear.

CT SCAN of Shoes While shoe manufacturers often have the 3D dimensions of their products for user fitting purposes, some may not. A high speed shoe scanner is used in such cases. As shown in FIG. 1E, a CT scanner can provide inside dimensions of the footwear that can be used to best-match the user's foot. Additionally or instead, the system may receive measurement data for at least some footwear models via user input, via a communication from manufacturer of the footwear, or both.

As shown in FIG. 1E, the X-CT scan system according to the embodiment of the invention comprises a main controlling and data processing computer 33, a base 34, a shoe rotary support and mechanical control device thereof 32 placed at the center of the base 34 and for placing the shoe to be modeled in 3D, a X-ray generation device 31 and a data acquirement system which are at two sides of the base 34. The data acquirement system comprises a planar array detector 35, a readout circuit and control logic unit for detecting X-ray projection data and the projection data on the detector. The main controlling and data processing computer 33 is responsible for the main controlling during the X-CT system operation, and processes the project data obtained by the data acquirement system to reconstruct a three-dimension image of the whole the shoe, and display it on a display. One side of the planar array detector 35 is leveled to the prolong line of the connecting line between the X-ray source 36 of the X-ray generation device 1 and the center of the shoe rotary support. That is to say, the planar array detector 35 is axially deviated with one side thereof passing the axis. The X-ray source can be an X-ray tube, an accelerator radiation source or an isotope source, which depends on the shoe size and application circumstance. The number of the detectors in the data acquirement system is reduced by half than that in the convention one, and the projection data related to the entire acquirement system is reduced by half.

The control, data transmission and image reconstruction of the CT system is executed by a computer workstation. The scan control information, position information and projection data are transmitted through the data acquirement system to the computer workstation, which performs the three-dimension image of the shoe, and displays it in three-dimension on a display. In order to precisely reconstructing the image, the X-ray imaging system should accurately measure or define the following parameters, the distance D from the X-ray source point to the detector, the distance R from the X-ray source point to the axis of the rotary support, the mapping position $P(\theta, u, v)$ on the imaging screen of the X-ray source point, the pixel size dx of the imaging screen, and the rotary degree $\theta$ of the rotary support. According an embodiment, the reconstruction algorithm uses the cone-beam rebinning method. Firstly, the cone-beam projection data intercepted in 360 degree scope derived from the output of the detector is rebinned to parallel-beam projection data of 180 degree scan scope. A complete three-dimension image of the shoe is reconstructed through a convolution back-projection method.

Depending on the information available, some additional measured parameters may be assigned a numerical or descriptive value representing the measurement. For example, one particular model of running shoe may have approximately 1 cm of stretch in the heel area. Another model may have a high level of cushioning. In the data set, for this shoe model the measurement parameter for cushioning may be set to "high" or a similar numerical value representing a high level of cushioning. Alternatively, some additional measurement parameters may be assigned merely a binary value representing a true/false or yes/no value, indicating whether or not the footwear model exhibits this additional parameter. For example, a running shoe having racing spikes may only have an associated value of "yes" (or "true" or "1") as the value for a "racing spikes" parameter in the data store.

In addition, the parameters may include additional retail-specific parameters. For example, information related to consumer ratings can be stored in the data set. Similarly, information such as return or replacement numbers and reasons for return can be stored in the data set to provide additional information related to a particular wearable item.

The computing device can access the data set to retrieve the stored information related to the user-selected item, and analyze the stored measurements and parameters associated with the user-selected item. The computing device may also prompt the user to provide sizing information. For example, the system prompts the user to provide the size that he or she typically wears in a running shoe. Alternatively, the system may retrieve the user's primary size from information previously provided by the user, such as a user profile or previous purchase data. After the system receives the user's primary sizing information, the system may determine a recommended size of the user-selected item and provide the recommendation. The determined size may be a primary size or an alternate size, depending on the model selected and whether or not the selected size of that model runs true to fit. The size determination process will be described in more detail below.

Insole Sensors and Environmental Controller

Figure 1F:
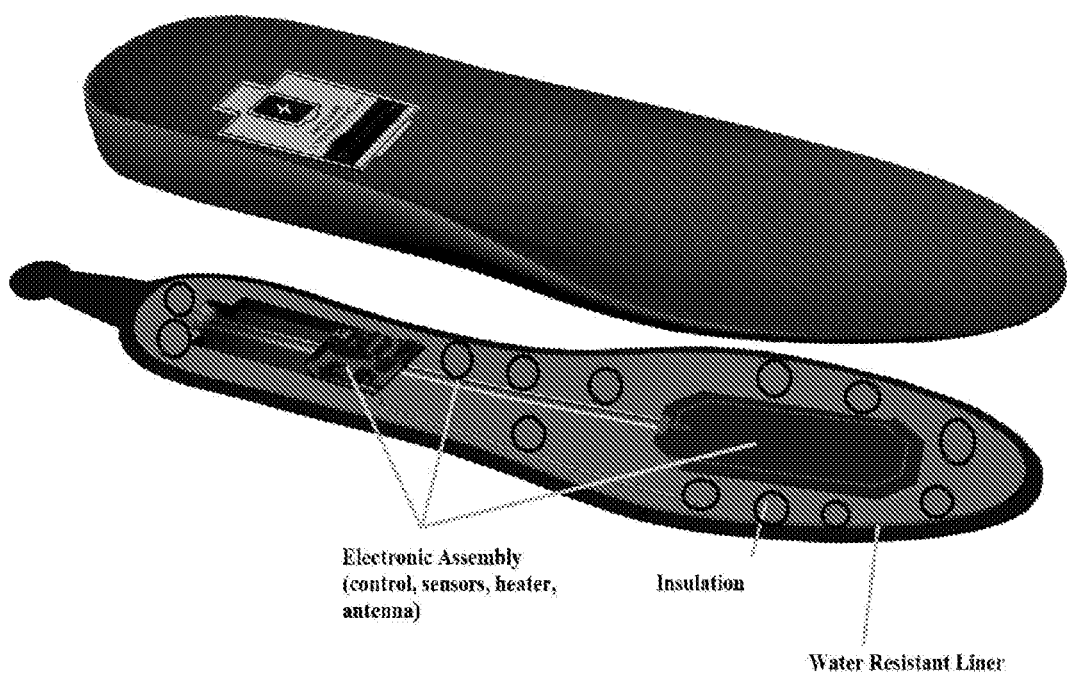
FIG. 1F shows exemplary footwear with sensors and heater/cooler embedded therein.

FIG. 1F shows the insole with foot sensors for the above data capture. The insole can optionally include heater/cooler for comfort. The cooler can run during the summer months, while the heater units operate in the winter months. Based on a remote setting, the heated/cool Insoles heat to a specific temperature, providing the user with just the right amount of warmth. Like the thermostat in the home, heated Insoles reach the temperature of the user—then temporarily turn off—coming back on when more heat or cool is needed. These insoles are designed to warm up to specific temperatures where you will remain warm and comfortable, but don't overheat and sweat. An insulated layer is provided between the feet and the bottom of the shoes or boots to stop heat/cool air from escaping. The water-resistant fabric liner absorbs any moisture, and the molded, flexible polyurethane material provides the dry comfort. Removable, replaceable batteries can b used to swap them out without having to take the insole out of the shoes or boots. A esilient, shock-absorbing Poron battery cover is used for added cushion and protection. The device of FIG. 1F may also be a sole of a shoe, a sandal, a sock, sock type device, or a boot. The device contains a plurality of sensors connected by connections to a control electronic. Sensors may be resistive pressure sensors, but are not limited to resistive pressure sensors and can be a variety of other types of pressure sensors as well as other physiological and biomechanical sensors. In either case, the controller receives raw data from pressure sensors and generates pressure data for transmission to a local base station or a smart phone. As many sensors as needed are contemplated. A transmitter is used to transmit the pressure data to the base station such as a Bluetooth PC or mobile phone, for example. In operation, pressure sensors sense pressure from a foot placed on them. The pressure sensor can be piezoelectric sensors, capacitive sensors, or resistive sensors. For example, where pressure sensors are resistive sensors, the resistance in primary pressure sensors varies as different pressure and/or force is applied to them. The controller sends current through pressure sensors and determines the pressure at each pressure sensor from the resistance detected. Based on the pressure, the shoe can be customized to compensate for any unsuitable pressure experienced by the wearer and optimize the walking experience.

In addition to pressure sensing, other personal data can be captured. For example, the sensors can include foot bio-impedance sensors that use bioelectrical impedance analysis (BIA) to estimate the heart rate by amplifying the pulsatile impedance component superimposed on the basal impedance. One embodiment detects the heart rate (HR) from bioimpedance measured in a single foot. Four electrodes are used for measurement of bioimpedance signal; two electrodes for injecting current and the other two to capture the voltage signal from human body. The bio-impedance signal shows deflections corresponding to systole and diastole activity as a measure of heart rate. The electrodes embedded in the footwear can apply a 50 kHz voltage between the outer electrode pairs and measure the drop in voltage across the inner electrode pairs in one embodiment. An impedance converter AD5933 separates impedance into real and imaginary part using discrete Fourier transform. The real and imaginary values of the measured bio-impedance signal are processed by a processor to obtain a continuous signal. The bioimpedance signal obtained after de-noising using adaptive thresholding. For heart rate detection, synchronous demodulator plays vital role by demodulating the bio-impedance signal from current carrier. To achieving high CMRR in signal in analog differential synchronous demodulator for AC signals, the signal is synchronously demodulated using the floating-capacitor with high CMRR. An impedance analyzer is used for getting bio-impedance signal. Wavelet thresholding methods can be used for noise removal where wavelet coefficients are threshold in order to remove their noisy part.

Another embodiment measures heart rate and/or EKG with sensors directly provided in the footwear or using external wearable devices and such data combined with foot-ground contact information is used for ambulatory estimates of maximal aerobic power from foot. The user's maximal rate of oxygen uptake sets the upper limit for sustained physical activity and is the standard measure of aerobic fitness.

The footwear can include piezoelectric elements that generate electricity and also can be actuated to cancel or dampen vibrations. In this piezoelectric embodiment, a shoe body is positioned above a base that includes a plurality of spring blades or leaf spring elements. Each spring blade has a top portion that extends from the base in a curved manner and a bottom portion secured to a blade foot. The blade can be plastic springs, which get compressed with each foot strike and recoil as the wearer proceeds through the gait cycle. In one embodiment, the base and the spring blade can be a piezoelectric composite that is directly molded into the shape of the base and the spring blades. The base can be an energy storage device, as detailed below. In another embodiment, the base is connected to individually tuned blades designed to propel runners. In one embodiment, 16 blades are composed of a highly elastic, piezoelectric polymer that is angled forward for high energy return in any environment. In addition, each blade is tuned to provide support in each phase of a runner's stride. The shoe can spring back with each step and propel a runner forward. The blades have different thicknesses and angles, which can influence the amount and direction of that energy return. Each blade is "tuned" differently to correspond to its position on the shoe, as well as to take into account body mass; men and women will get shoes with the appropriate amount of flex and response.

In an embodiment, the base can have a flexible and stretchable battery composed of strain free LiFePO4 cathode, Li4Ti5O12 anode and a solid poly ethylene oxide (PEO) electrolyte as a separator layer. Featuring solid thermoplastic electrolyte as a key enabling element this battery is potentially extrudable or drawable into fibers or thin stripes which are directly compatible with the weaving process used in smart textile fabrication. In an embodiment, a materials system for the design of a drawable lithium polymer battery with a view of eventually obtaining a battery-on-fiber is disclosed. The cathode material used in one embodiment is LiFePO4. While the base or sole can be the battery, the upper or flexible portion covering the foot can also include the battery or a suitable energy harvesting device such as solar cell.

In one embodiment where the insole is strengthened at the bottom to become a sole, the shoe has an upper surface (upper) that can be fabric, leather, or synthetic materials for cooling/warming the foot. One embodiment of the shoe covers the upper surface with a solar electricity generator whose output is connected to a power regulator. Inside the shoe, a sole contains a piezoelectric device covering the entire foot is used to generate electricity. In one embodiment, the sole can be a piezo sole from Smart-Material Corp. of Sarasota, Fla. The shoe also contains electronics such as CPU, transceivers, energy store (such as batteries or supercapacitors) and power regulator. The regulator can accept electric output from a variety of sources including piezoelectric devices and solar cells, for example. The sole plate can include a connector such as a micro USB connector to recharge a flexible energy storage device such as a flexible battery, or alternatively can be a flexible supercapacitor. The shoe can also receive recharge through inductive charging or other wireless charging systems. In one embodiment, the human foot electrically touches a pad on the shoe to provide contacts for a BAN communication network with sensors mounted on the wearer's body. As noted above, the sensors can be an EMG detector, EEG detector, an EKG detector, an ECG detector, a bioimpedance sensor, an electromagnetic detector, an ultrasonic detector, an optical detector, a differential amplifier, an accelerometer, a video camera, a sound transducer, or a digital stethoscope. The bioimpedance sensor can determine one of: total body water, compartmentalization of body fluids, cardiac monitoring, blood flow, skinfold thickness, dehydration, blood loss, wound monitoring, ulcer detection, deep vein thrombosis, hypovolemia, hemorrhage, blood loss, heart attack, stroke attack. The sensor can also communicate with an indoor position sensor, a motion sensor, a door sensor, a bathroom sensor, a water overflow sensor, an exercise equipment sensor, a smoke detector, an oven sensor, a cooking range sensor, a dish washer sensor, a cabinet door sensor, a refrigerator sensor, a refrigerator container sensor, a kitchen water flow sensor, a dish sensor, a bowl sensor, a chair sitting sensor, a sofa sitting sensor, a bed sensor, a weight sensor, a television viewing sensor, a radio listening sensor.

Insole Weight Scale

The shoe can contain a weighing system to provide real-time measurement of the wearer's weight. Alternatively, a shoe pad insert or a sock or an adhesive band-aid can contain the weighing elements for temporarily measuring the wearer's weight. The system can have an array of force sensing resistors or weight sensitive sensors such as piezoelectric sensors. One embodiment can provide a resistor array in the form of a resistive (carbon) sheet with interdigitated contacts that can be shorted when weight is applied to change the overall resistance of the resistor. The resistor is calibrated to convert a predetermined resistance to a particular weight. The resistor can be flexible polymers to deal with loading conditions. In a liquid sensing embodiment, a fluid cavity or an array of fluid cavities is provided with a liquid that is displaced or pressurized as a function of weight. The array of cavities may be constructed to handle different pressures and sensitiveness. For example, a large cavity can be positioned under the foot section that absorbs most of the weight, and a small cavity can be positioned near the center of the foot as that part receives light pressure. With the single or array of cavities, a calibrated pressure sensor is used to detect weight. Alternatively, a pressure sensor can be embedded in the shoe, insert, sock, or band-aid to directly measure weight without the fluid cavity. The system can include temperature and altimeter sensors to better predict weight and to capture health parameters, for example. Using the sensors, a wearer can review his or her weight at nearly any time. Runners using such a system and device to know their hydration loss; chiropodists may wish to monitor weight distribution over a patient's feet; and athletic trainers may wish to analyze weight distribution and forces. In one embodiment, only a portion of the foot need to be covered, covering a certain percentage of the overall weight; and that percentage is scaled to a user's full weight. Weight and compression forces monitored in a shoe or shoe insert, in accord with the system, can further assist in gauging caloric and/or physical effort.

The weight sensors can communicate with processor in the sole or can communicate with a wireless phone using a personal area network such as Bluetooth or with a remote processor using WiFi, for example. The shoe weight is known and can be subtracted from the total weight to arrive at the wearer weight. Precise weight and heart rate measurement data can be used as part of a population health management system to keep patient weight to an ideal health. The weight information can be used to detect short term loss of water such as after marathon, race, soccer/football game, or intense outdoor activities such as hiking, for example. If weight loss indicative of dehydration, the processor can let the wearer know to drink water and rehydrate, for example. As the sensors also detect foot/ground impact, they can detect improper walking/running postures and report to users or doctors for corrective actions.

A shoe-mounted or shoe-integrated device can monitor shoe usage and indicate when the shoe has exceeded its useful life. The sensor can detect events of the footgear due to activity of a wearer. The events can be impact events or rotational events, but are not limited to such events. For detecting impact events, the sensor can be an accelerometer responsive to motion. For detecting rotational events, the sensor can be a Hall-effect sensor, which can be responsive to a rotating element, such as a Ferris element. The processor can count the events detected by the sensor and maintain a cumulative event total. The processor can then compares the cumulative event total to an event threshold, which can be calculated from the predetermined number of events and an individualized factor. The individualized factor can include at least one of the wearer's weight, the climate where the footgear is worn, a type of predominate surface on which the footgear is worn, the wearer's age, the wearer's foot pronation or running style (such as whether the user is a heel striker or toe striker), and the wearer's injury history. The sensor, processor, and display can be secured within the footwear and communicates with a smart phone or a computer using a PAN such as Bluetooth and the sensor can be powered by a coin cell battery, solar cell, or piezoelectric electric generator.

The device can estimate distances run or can measure the shoe's operating parameters, such as cushioning. In a particular embodiment, the device can include a sensing unit, a programmable processor interpreting data from the sensing unit, and an indicator for notifying the wearer of the shoes' status. The processor can be programmed during manufacturing to incorporate typical variable values that are relevant to measuring shoe life. The processor can also be field programmed by the retailer or end user to enter individualized, wearer-specific variable values.

In one embodiment, a wear monitor can indicate when a shoe or component may have exceeded its expected useful life. The indication can be triggered by a measure of use, such as steps taken or distance accrued in the shoes, either through estimation or actual measurements. The monitor can take into account varies parameters related to the wearer of the shoe and environmental factors to more accurately determine when a pair of shoes has reached a wear out period. By employing sensors, the monitor can also be measure certain operating parameters of the shoe, such as the loss of a critical amount of resilience, and indicating to the wearer that the shoes are no longer adequate to protect the wearer from injury. The wear monitor can be fabricated into the shoe during manufacturing or can be a portable stand-alone device and can employ various technologies to provide a status indication to the wearer.

Another particular embodiment can include a method for estimating wear to a component of footgear based on the expected functional life of the component, as determined by a predetermined number of events. The method can include calculating an event threshold based on the predetermined number of events and an individualized factor, counting the events detected by a sensor, maintaining a cumulative event total, and comparing the cumulative event total to the event threshold. The method can also include displaying a representation of the comparison on a display device.

The individualized factor can include at least one of the wearer's weight, the climate where the footgear is worn, and a type of predominate surface on which the footgear is worn, the wearer's age, the wearer's foot pronation or running style (such as whether the user is a heel striker or toe striker), and the wearer's injury history.

The processor can calculate an event threshold based on the predetermined number of events and individualized factor, count the events detected by a sensor, from the counting, maintain a cumulative event total, and compare the cumulative event total to the event threshold. The individualized factor can include at least one of the wearer's weight, the climate where the shoe is worn, and a type of predominate surface on which the shoe is worn, the wearer's age, the wearer's foot pronation or running style (such as whether the user is a heel striker or toe striker), and the user's injury history.

Mass-Customized Sole/Insole Design Process

The above processes can arrive at the inside dimensions of a particular shoe that best fits the user. However, the standard shoes may still need further customization to support the user's particular body dimensions such as arches. Thus, a mass-customized insole is detailed next.

One embodiment is a diagnosis and a system for design of patient-specific orthotics focused principally on dealing with the kinetics of pronation. In the functioning foot there are specific relationships between the anatomical structures commonly identified from both the frontal plane and the sagittal plane of reference. Instability can result from a misalignment between the forefoot and rear-foot which prevents the foot from functioning in a fully integrated manner. However such a simple structural (kinematic) classification as this overlooks the critical matter of how muscular energy is transmitted through anatomical structures in such a way as to confer normal motion (kinetic function) on the foot. For example, the pronation force about the sub-talor joint axis is known to increase as a result of structural misalignment. But an analysis in kinetic terms would account for the origin and magnitude of the pronation force and why this force affects the sub-talor joint. Once the problem is presented in kinetic terms, the anatomical structures are seen to play their part in the resolution and transmission of forces rather than suggesting their source.

The system also models kinetic processes in the foot using Kirby's dynamic equilibrium between the sum of pronation and supination forces occurring about the sub-talar joint axis. ("Rotational Equilibrium" theory (Kirby, K. A. 2001 "Sub-talar joint axis location and rotational equilibrium theory of foot function" JAPMA 91(9): 465-487)), the content of which is incorporated by reference. Assessed from the sagittal plane of reference, the foot has been described as a compound pivot made up of three key pivots. The three key sagittal plane pivots can be named the "Heel rocker" the "Ankle Rocker" and the "Forefoot Rocker". Foot pronation results when a restriction occurs at either the ankle pivot or the forefoot pivot during gait. Restriction is revealed by the inability of the ankle or forefoot rocker to function normally. Restriction can be anatomical or physiological in origin and its extent can be influenced by footwear or orthotics or both. If restriction at a key pivot sites persists of foot becomes chronically unstable, pronation becomes endemic. This process can lead to deterioration in pivotal function and further instability.

The fabrication of an orthotic insert or shoe for a patient's foot can include providing shoe sensors with pressure sensors or accelerometers (as detailed in FIG. 1F which shows exemplary footwear with sensors and heater/cooler embedded therein) to the user to pace the foot to one or more of the following tests and ascribing a test value(s) within a predetermined set of relative values for each test which is indicative of one or more properties of the patient's foot:

(i) supination resistance test (as defined); and
(ii) Jack's test (as defined);
(b) recording each test value in a database;
(c) comparing the test values to control values indicative of one or more predetermined orthotic designs stored in the database; and
(d) selecting an orthotic design(s) from the predetermined orthotic designs dependent on that comparison.

The process may further include one or more of a skeletal integrity test, a fascial chord tension test, an ankle joint stiffness-lunge test, a principal activity velocity test, a sagittal plane morphology test, and a hamstring stiffness test. More explanation of the various tests is as follows:

(a) Supination Resistance Test—This is the amount of force required to resupinate the foot. With the patient standing in a relaxed weight bearing position, the force is graded on various levels and recorded from very low to very high. This index reveals where the centre of pressure is to be applied to the foot by the orthotic device, whether towards the back or the front. Foot integrity is also estimated from the amount of change in arch amplitude observed when the foot goes from a non-weight bearing position to a weight bearing. The change in arch amplitude may be measured within a range of five increments categorized from very low to very high; if the amplitude changes by two increments, the foot is classified as a foot with poor integrity, whereas if the change is just one increment the foot would be classified as one with good integrity. If there is no change then the integrity measure is scored as excellent. These integrity measures give further information for application of the design parameters that relates to the amount of rear foot to fore foot support.

(b) Windlass mechanism test—Jack's Test and Fascial Chord Tension Test. The force required to lift the hallux when the patient's foot is in a full weight bearing position is determined by The Jacks Test. When the hallux is lifted, the foot automatically begins to resupinate. The force to initiate the foot resupination is graded on three levels form low to high. This index provides additional information as to the placement of the centre pressure in the orthotic design. Fascial Chord Tension Test is as follows. With the foot non-weight bearing, the first metatarsal is dorsi-flexed and the prominence of the fascial chord is recorded. The prominence of the fascial chord is graded from low to high. This parameter is important as this allows the design to be modified to accommodate the fascial chord by way of a fascial groove. It is important to be able to adjust the design this way to help protect and facilitate the windlass effect. The orthotic design may require further adjustment including wedging in the rear foot to help push the chord out of the way.

(c) Sagittal plane morphology test. This categorizes the foot in terms of the gradient, the anterior calcaneal surface and the foot apex position. The gradient is evaluated as low, medium, or high. The foot apex position when combined with the gradient is categorized as rear, central, or forward, providing key information on the amount of soft tissue that surrounds the anterior heel area and can affect the amount of rear foot orthotic contour applied in the design.

(d) Hamstrings tension test. This is a test indicating the amount of tension in the hamstrings so as to determine the possible compensatory impact on the ankle joint in the close kinetic chain. Hamstring tension is graded on three levels low, medium and high. When the tension is categorized as high changes are made to the design so as to facilitate sagittal plane function.

(e) Lunge test. Failure in this test implies that greater ankle joint facilitation must be provided for in the design. The design will reflect the increased force needed to establish foot resupination.

(f) Principal activity velocity test. The principle activity velocity is defined as the level of activity the device is being designed for whether that is predominantly standing or moderate walking or running The activity is graded on three levels from low to high. This is recorded as an index. When applied to the design it influences whether there is a need to more closely contour to the foot type or wedge more the rear foot area of the orthotic. The greater the velocity the greater the force of correction required and the further back the device apex should be.

One exemplary process applies the following Criteria for Classification of Foot Posture (Cross and Lehman)
Supination of the Subtalar Joint
Inverted calcaneus
Shallow concavity superior to the lateral malleolus
No concavity inferior to the lateral malleolus
High arch Neutral Subtalar Joint
Vertical or slightly inverted calcaneus
Even concavities above and below the malleoli
No curvature of the Tendo Achilles (TA)
No bulging of the medial aspect of the foot
Discernable medial arch
Pronation of the Subtalar Joint
Eversion of the calcaneus (relative to the lower leg), but only to vertical (relative to the weight bearing surface)
Bulging of the medial aspect of the foot
Long sloping concavity superior to the lateral malleolus
Small deep concavity inferior to the lateral malleolus
Flattened medial arch (differentiated from a pathological pes planus on external rotation of the weight bearing leg: if the arch configuration changes with external rotation of the lower leg the indication is that the arch can recover).
Hyperpronation of the Subtalar Joint
Eversion of the calcaneus (relative to the lower leg), beyond vertical (relative to the weight bearing surface)
Bulging of the medial aspect of the foot
Long sloping concavity superior to the lateral malleolus
Small deep concavity inferior to the lateral malleolus Flattened medial arch Helbing's Sign May Also be Apparent The design process begins in several different ways. One option is to load a scanned foot model. Another option is to load a generic, modified insole template. Generic templates of various sizes provide a useful starting point for the design of custom insoles. Another option is to load a third-party patient data file, which may contain information about pressure data (dynamic forces and pressure distributions created in the patient's foot while walking), laser scan data, or medical DICOM files as mentioned above. Together, the insole file, image file, and data files may be saved into a single patient insole file. An insole CAD system can be used to edit the foot model. The edit functions generally allow insole design personnel to add protrusions or carve out recesses in the insole to accommodate user specific requirements. For example, the PAD and MTT (Metatarsal) functions create pads on the surface of the insole that serve to redistribute forces in the patient's foot. Similarly, the CIRCLE and POCKET functions create recesses to alleviate pressure on injured or irregular surfaces of the foot. In addition to the four functions described, the EDIT menu in the Insole Modeler includes the following edit functions: Height Front, Height Back, Measuring, MultiPoint, Area, Plateau, and Arch Support. The HEIGHT FRONT and HEIGHT BACK functions are designed for elevating parts of the insole, which may be used for eliminating surplus elements on the front or the back of the insole, thereby making the insole thinner or for creating shoe fillings in cases of amputated feet or other deformities. The MEASURING function calculates distances between points in the model and can preferably provide linear as well as coordinate distances in pixels and inches or millimeters. The MULTIPOINT function is a true 3D function for generating new surfaces defined by multiple points interconnected by lines. This function is useful for deepening or raising the edges of the insole, for creating channels for releasing pressure from the plantar fascia, or for designing a heel cup, which is important in cases of tendonitis, bursitis, and partial or total ruptures of the Achilles tendon. The AREA and PLATEAU functions are similar in that they are free form raised or recessed areas defined polygonally by setting points on the surface of the insole. The difference between the two is that in the AREA function, the recess or raised portion converges to a point whereas the plateau rises or falls to a flat surface. The ARCH SUPPORT function is one of the most commonly used functions in the Insole Modeler 930. The function is relatively self-explanatory and is used to add outer support for the longitudinal arch area. The Final Adjustments Functions 1050 generally permit large-scale modifications to the insole. For example, the thickness of the insole is modified by the LIFT UP or LOWER DOWN functions while the lateral tilt is altered using the PRONATION or SUPINATION functions. The heel of the insole is defined by specifying the HEEL LENGTH, CROSSING LENGTH and HEEL DELTA HEIGHT parameters. The Global Change functions allow modification to the insole as a whole. For example, the SMOOTHING function is used to eliminate uneven surfaces created during the scanning procedure or to smooth sharp edges created by local editing functions. The SCALING function allows the designer to change the scale of the insole along any or each of the three Cartesian coordinates (i. e., X, Y, or Z axes). The ZOOMING function permits insole modelers to view the insole from different perspectives and with different magnifications. The MIRRORING function permits the copying of existing features about a user-defined mirror axis. The final insole 3D model is then sent to a mass-customized insole 3D printing system as detailed below.

3D Printed Soles

Figure 1G:
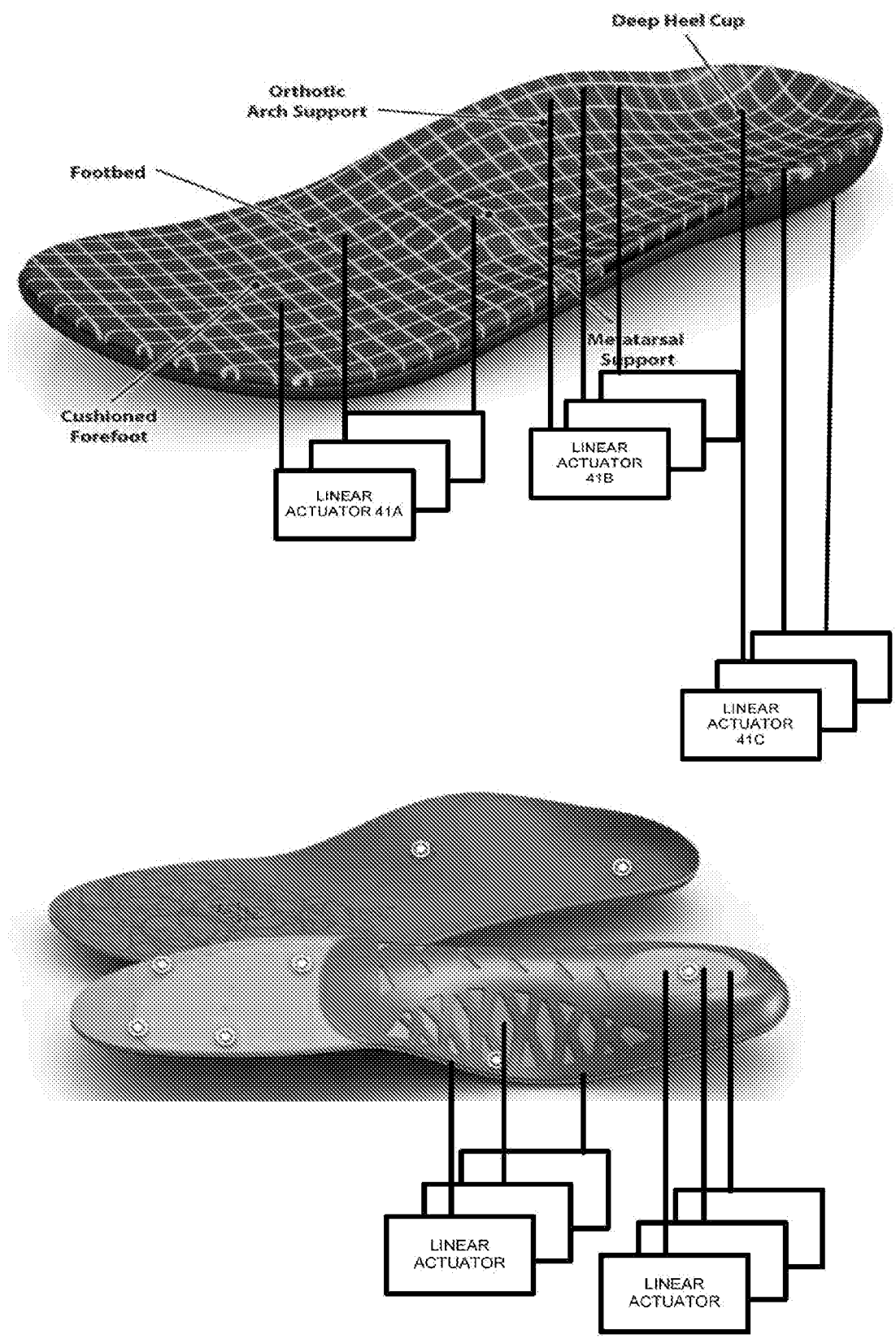
FIG. 1G shows exemplary templates for rapid, inexpensive 3D printing of insoles with sand.

FIG. 1G shows an exemplary template for rapid, inexpensive 3D printing of insoles using engineered sand technology as described in more details below. In this system, a plurality of templates is provided, one for each foot size such as 7, 8, 9, 10, 11 and in-between sizes. The right size for the user is selected and inserted into the bed of sand and a computer controls actuators 41A-41C to customize the curves to the user's dimensions. Sand is flowed over the customized templates and set. The template is removed, and rubber or suitable insole material is poured into the sand bed and cured and removed for final cleaning/polishing if needed. The sand bed can be reactivated for another insole or sole. For forming custom shoes, the insole can simply be padded with more materials, and an outer can be stitched or glued to the sole.

Each template is mechanically connected to an array of linear actuators that can morph the dimensions of the insole to personalize the insole to the specifics of the user. In the embodiment of FIG. 1E, a number of specific spots are adjusted such as the deep heel cup region, the orthotic arch support region, the foot bed region, and the forefoot region. The linear actuators 41A, 41B, and 41C can be electric or hydraulic or shape actuated materials such as nitinol and can push or pull the insole to provide the desired cusps to best fit the user.

Figure 1H:
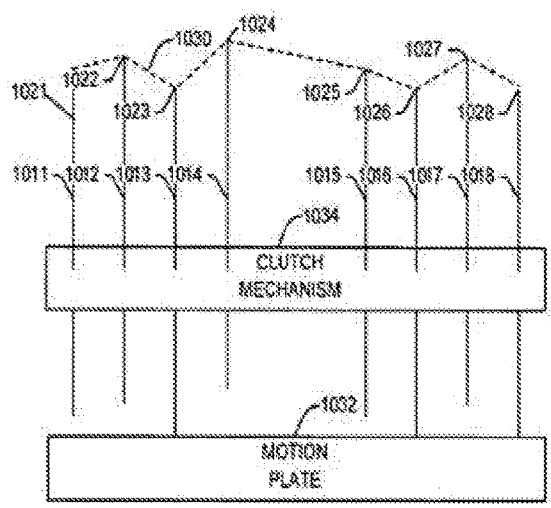
FIGS. 1H-1I show exemplary systems and techniques for manufacturing in volume with a wide range of materials are disclosed for fabricating shoes at mass customization scale.
Figure 1I:
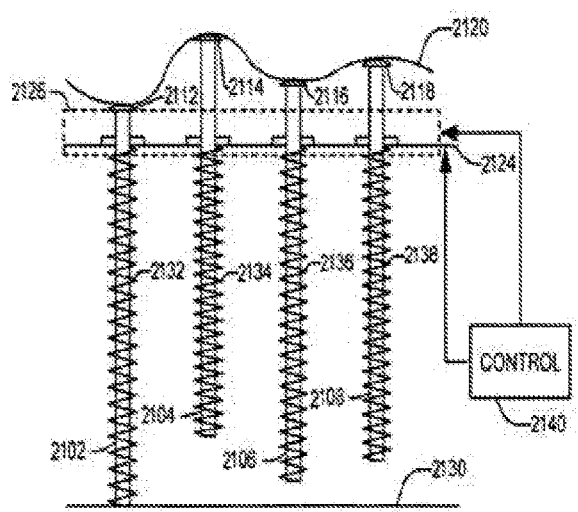

While conventional additive manufacturing 3D printers can be used for mass-customization of the shoes, the material available is limited and the print speed is slow, leading to fragile and expensive shoes. FIGS. 1H-1I show exemplary systems and techniques for manufacturing in volume with a wide range of materials are disclosed for fabricating shoes at mass customization scale. The system can also be further cleaned up after manufacturing using CNC for smoothing the soles, stiching fabrics onto the sole, or any other required post-processing manipulation of the fabricated shoes.

In one aspect, systems and methods are disclosed for shaping a reformable material by holding a volume of particles inside a container having a first elastomeric membrane surface; infusing the volume with a liquid to mobilize the volume of particles; and pressing a master shape into the membrane with atmospheric pressure.

In another aspect, a method to form an object includes infusing a liquid into a container having a first elastomeric membrane surface; pressing a master shape into the membrane with atmospheric pressure; and shaping a reformable material into the object according to the master shape.

In yet another aspect, a method to form an object includes infusing a liquid into a container having a frame with first and second elastomeric membranes; a first port to deaerate the volume of particles; and a second port to infuse the volume with a liquid for mobilizing the volume of particles; pressing a master shape into the membrane with atmospheric pressure; and shaping a reformable material into the object according to the master shape.

Implementations of the above aspects may include one or more of the following. The volume of particles can be deaerated. The liquid can be extracted through one or more screen elements placed proximal to the volume of particles. The atmospheric pressure continues to hold the particles in place against the elastomeric membrane when the master shape is removed from the outer surface of the membrane. The method includes heating and driving liquid from the particle volume. A residue of a binding adhesive is left to lock the particles into a continuous force-resisting mass. A complementary shape is impressed to the master shape in the membrane. A rigid outside frame can be used with top and bottom elastomeric membranes facing the top and bottom surfaces of the container. The master shape can be pressed against the top elastomeric membrane of the container by atmospheric pressure. The pressing operation includes applying a flexible vacuum cap which is sealed over the shape and against the container's top surface membrane; evacuating air from a space between the top membrane and the vacuum cap; extracting liquid from the volume; and pressing the particles within the container by atmospheric force acting in opposed directions against the vacuum cap and the bottom surface membrane. Air can be introduced into the vacuum cap, and then the cap and the master shape can be removed from the formed surface of the elastomeric membrane. The container is formed against the master shape. The method includes placing the master shape on an air-impermeable surface; placing a membrane of the container over the shape; and placing a vacuum cap or a vacuum-bagging film over the container to effect forming of the elastomeric membrane against the master shape. An envelope with a vacuum seal on its perimeter can be used to contain a mass of particles and to extract air from between the master shape and the envelope. The master shape can be placed on the top elastomeric surface of a first rigid-framed container and a membrane surface of a second container can be placed over the master shape. The second container fits inside the frame of the first container and a vacuum cap is placed over and sealed outside the second container against the surface membrane of the first container. The method includes evacuating the volume under the vacuum cap and pressing the master shape between the elastomeric sides of the first and second containers. The liquid is extracted so that the two volumes of particles are pressed together and against the membranes surrounding the contained shape. The vacuum cap can be vented with air and removed; the top container can then be removed; and the shape can then be removed from the membrane of the bottom container. The top container can be placed over the bottom container; and forming a closed, shaped cavity complementary to the surface of the master shape used to form the cavity. Two identical containers of either the first or the second container can be pressed around a master shape with or without using the vacuum cap. The containers can be joined and sealed by either a seal mounted on one or both of the containers or by seals mounted on a seal ring which fits between the two containers. The liquid can be extracted prior to the master shape being removed from the shaped reformable material. The liquid can be withdrawn to leave a residue of liquid on the shaped reformable material; and solidifying the residue. The method can include preforming a surface material over the master shape as with thermoforming or additive processing. The container walls can be air and liquid impermeable. An inelastic formable surface can be used that conforms to the master shape surface. A surface can be formed over the master shape to conform to the master shape and the shaped material surface can be pressed against the volume of particles without deforming the shaped material surface. The method includes providing a release surface to the master shape; pressing the master shape against the volume of particles to form the object against the release surface; and removing the object from the master shape with the release surface. The release surface can be applied to the master shape with a surface element covering the reformable material surface not overlaid with the master shape surface.

In another aspect, an apparatus to form an object in accordance with a master shape includes a container to hold a volume of particles, said container having a first elastomeric membrane surface; a first port to deaerate the volume of particles; and a second port to infuse the volume with a liquid for mobilizing the volume of particles; and a press coupled to the container to move the master shape into the membrane to shape a reformable material into the object according to the master shape.

Implementations of the above aspect may include one or more of the following. One or more screen elements can be placed proximal to the volume of particles to extract the liquid. Atmospheric pressure can be used to hold the volume of particles in place against the elastomeric membrane when the master shape is removed from the membrane. A heater can be used to heat and drive liquid from the particle volume. The container can be a rigid outside frame and top and bottom elastomeric membranes facing the top and bottom surfaces of the container, and wherein the master shape is pressed against the top elastomeric membrane of the container by atmospheric pressure. The apparatus can include a flexible vacuum cap sealed over the shape and against the container's top surface membrane; a third port to evacuate air from a space between the top membrane and the vacuum cap; and pressing of the particles within the container by atmospheric force acting in opposed directions against the vacuum cap and the bottom surface membrane. Air can be introduced into the vacuum cap and then the cap and the master shape can be removed from a surface of the elastomeric membrane. The master shape can be placed between an air-impermeable surface and the membrane of the container and wherein a vacuum cap or a vacuum-bagging film is placed over the container to form the elastomeric membrane against the master shape. An envelope with a vacuum seal on its perimeter can be used to contain a mass of particles and to extract air from between the master shape and the envelope. The master shape can be placed on the top elastomeric surface of a first rigid-framed container and placing a membrane surface of a second container over the master shape. The second container fits inside the frame of the first container and a vacuum cap is placed over and sealed outside the second container against the surface membrane of the first container. A vacuum pump can evacuate the volume under the vacuum cap and press the master shape between the elastomeric sides of the first and second containers. A pump can extract the liquid so that the two volumes of particles are pressed together and against the membranes surrounding the contained shape. The vacuum cap can be vented with air and removed; the top container is removed; and the shape is removed from the membrane of the bottom container and the top container is placed adjacent the bottom container to form a closed, shaped cavity complementary to the surface of the master shape used to form the cavity. The first and second containers can be identical and can be pressed around a master shape without using the vacuum cap. The containers can be joined and sealed by either a seal mounted on one or both of the containers or by seals mounted on a seal ring which fits between the two containers. A seal ring can be used to channel vacuum or air pressure between the containers and to hold the master shape in a precise orientation and position between the two opposed containers. An expander can be used within the container to press the particulate material against cavity walls of the container. The apparatus can include a second container cooperating with the first container to form a complementary cavity from the master shape; and a third container placed in the complementary cavity to replicate the master shape. A rigid frame or a flexible-edge frame can be used. The frame can form a continuous surface complementary to a master shape's surface. A second elastomeric membrane can be used, and the elastomeric membranes can overlap or abut each other. Additional containers each having a membrane can be used with the container's membrane to form a continuous surface of membranes. Further, additional containers can be used to form a shape complementary to the interior of a master cavity.

In another aspect, an apparatus to form an object in accordance with a master shape includes a container to hold a volume of particles, said container having a frame with first and second elastomeric membranes; a first port to deaerate the volume of particles; and a second port to infuse the volume with a liquid for mobilizing the volume of particles; and a press coupled to the container to move the master shape into the membrane to shape a reformable material into the object according to the master shape.

Implementations of the above aspect may include one or more of the following. The second membrane is bonded to the frame. The first membrane is mounted to a seal. A clamp can secure at least one membrane to the frame. One or more ports can be provided on the frame. Liquid, evacuation, and vacuum-activated seal tubes can be mounted to the frame. A rim evacuation screen element can be positioned in the frame. The frame can be rigid or flexible. A vacuum activated seal can be provided on the frame. A tube can be used for evacuating and filling the container. Double layer screens having feed elements to distribute and extract liquid through the volume of particles can be used. One or more screens can be used to conform to the master shape. One or more internal screens can be mounted with the particles flowing on both sides of each internal screen. The frame can have one or more containers joined together around the master shape or alternatively can have one or more containers joined by vacuum seals. One or more feed tubes can connect to an interior element inside the membrane. A flexible spine element can be used within an interior cavity of the container. One or more reinforcement fibers can be used, and in certain implementations, the fibers can be distributed in bundles within the volume of particles. An air pump or source can be used to provide internal pressurization. A vacuum source can provide a vacuum between a cavity in the container and the container. An air source and a vacuum source can alternately pressurize and vent the container to distribute the volume of particles therein. A seal ring can be used. The seal rings can be mounted against seals or can be mounted with attached seals. The attached seals can be vacuum activated. A second container can be joined with the container and wherein a vacuum is formed in an interior of the joined containers. The master shape can be mounted on the seal ring. Flanges can be mounted to control a mating line between opposed membranes of containers. A second container can be positioned within a cavity formed by an outside container. A vacuum seal can be used with a vacuum cap. A vacuum tube can be used that penetrates through the membrane. A vacuum cap with mounted container can be used in place of the membrane. One or more screen elements can be placed proximal to the volume of particles to extract the liquid. Atmospheric pressure holds the volume of particles in place against the elastomeric membrane when the master shape is removed from the membrane. A heater can be used to heat and drive liquid from the particle volume. The container can have a rigid outside frame and top and bottom elastomeric membranes facing the top and bottom surfaces of the container, and wherein the master shape is pressed against the top elastomeric membrane of the container by atmospheric pressure. An envelope with a vacuum seal on its perimeter can contain the mass of particles and extract air from between the master shape and the envelope. The master shape can be placed on the top elastomeric surface of a first rigid-framed container and a membrane surface of a second container placed over the master shape. An expander within the container can be used to press the particulate material against master shapes and against cavity walls of other containers. The apparatus can have a second container cooperating with the first container to form a complementary cavity from the master shape; and a third container placed in the complementary cavity to replicate the master shape. A second elastomeric membrane can be used that either overlaps or abuts the adjacent membrane. Additional containers each having a membrane coupled to the container can be used to form a continuous surface of membranes. Additionally, one or more additional containers can form a shape complementary to the interior of a master cavity.

In yet another aspect, a base station is disclosed to form an object in accordance with a master shape. The base station includes a liquid receiver; a vacuum source to evacuate air from the liquid receiver; an air compressor, pump or source to generate pressurized air; and a controller coupled to the liquid receiver, the vacuum source and the air compressor to form the object.

Implementations of the base station can include one or more of the following. Tubes can be used to provide vacuum and to control the flow of liquids to and from the receiver. Valves, sensors, and other circuits can be interfaced with the controller. An electrical power source can be used to provide power to operate valves, sensors, the vacuum pump and the air compressor. The controller can be a menu-driven process controller. A heater can be used to vaporize and expel liquid from containers of reformable material. The reformable material creates contours of the master shape or alternatively can be molded against a complementary surface of an elastomeric membrane. The liquid contains a soluble binder, which can be left on a shaped volume of particles. The binder locks a shaped volume of particles in place after the liquid is removed. The heater can be a radiant heater, a convective air heater, microwave heater, radio-frequency heater, or inductive heater. The heater can include one or more heating elements within the container. The heater is controlled by the controller. A container can be used to hold a volume of particles, said container having a frame with first and second elastomeric membranes; a first port to deaerate the volume of particles; and a second port to infuse the volume with a liquid for mobilizing the volume of particles; and a press coupled to the container to move the master shape into the membrane to shape a reformable material into the object according to the master shape. Alternatively, the container can have a first elastomeric membrane surface; a first port to deaerate the volume of particles; and a second port to infuse the volume with a liquid for mobilizing the volume of particles; and a press coupled to the container to move the master shape into the membrane to shape a reformable material into the object according to the master shape. The container can include a rigid outside frame and top and bottom elastomeric membranes facing the top and bottom surfaces of the container, and wherein the master shape is pressed against the top elastomeric membrane of the container by atmospheric pressure. The base station can also include a flexible vacuum cap sealed over the shape and against the container's top surface membrane; a third port to evacuate air from a space between the top membrane and the vacuum cap; and pressing of the particles within the container by atmospheric force acting in opposed directions against the vacuum cap and the bottom surface membrane. The master shape can be placed between an air-impermeable surface and the membrane of the container and a vacuum cap or a vacuum-bagging film can be placed over the container to form the elastomeric membrane against the master shape. The vacuum pump can be a mechanical pump or an air driven pump such as a Venturi pump. A second vacuum pump can be used. Isolating valves can be used, and a regulator and one or more valves can be used to pressurize a liquid tank. A vent valve can also be used to cycle from a vacuum source to a pressure source. A three-way valve can route air and vacuum to the liquid tank. A filter can be used to prevent particulate carryover. An air-liquid separator and/or a level indicator can also be used. A vacuum, pressure, liquid and temperature sensor can provide data to the controller for process control. A heat exchanger can be used to condense vapor. A slurry transfer tank can be connected to the container. The container can be a single unit, or can have a plurality of containers adjacent to or inside the container to form a cavity. The containers can be mated with a seal ring.

In yet another aspect, a method to shape a reformable material includes holding a volume of particles inside a container having a first elastomeric membrane surface; and infusing the volume of particles with a liquid; agitating the liquid to provide one or more surges of liquid to mobilize the volume of particles; and pressing a master shape into the membrane with atmospheric pressure.

Implementations of the above method may include one or more of the following. The method may provide locally distributed surges or globally distributed surges. The surges can exert differential liquid forces on particles to displace them relative to one another and facilitate their movement into a closely-packed volume. A differential pressure can be applied between a master shape side and a liquid-particle side of the membrane. The pressure between a vacuum cap and the membrane can be decreased to move the membrane in a first direction or increased to move the membrane in a second direction. The membrane is free to move relative to the master shape. Excess liquid can be removed to leave particles against the membrane. Air can be evacuated from space between the membranes. The particles can be packed against the membranes and the master shape. The liquid with the vacuum cap and membrane pressed against the master shape can pack the particles against the membranes and the master shape. The agitating operation can include pulsing or vibrating the liquid. The vibration frequency can be adjusted to displace one particle relative to another to keep the particles moving freely in relation to one another. The amplitude of the liquid pulsation can be proximally equal to a diameter of the particles. A first surge of liquid can be directed towards a desired transport direction and a second surge smaller than the first surge can be directed in an opposite direction to the transport direction. The agitating of the liquid can be used to minimize blockage. The method includes maintaining the volume of the container constant and completely filled to force the particles against the master shape. The method includes extracting transitional liquid from the container; and adding new liquid equal in volume to the transition liquid.

In yet another aspect, a shape-reformable composition includes a carrier medium having a carrier density; and a plurality of solid bodies having a density substantially similar to the carrier density, said solid bodies being transitionable from a formable state to a three dimensional solid shape. The bodies can have a density substantially lighter or heavier than that of the carrier if they have a high ratio of surface area to volume. The bodies can be stiff, flexible or elastomeric. The bodies can be regular or irregular and can be of substantially different types intermixed.

Implementations of the composition can include one or more of the following. The carrier medium fills voids or interstices between the solid bodies such that the voids or interstices are free of air or gas bubbles. The solid bodies can have near-liquid or fluent mobility during the formable state. The solid bodies can transition to the solid shape through an introduction and an extraction of a predetermined amount of the carrier medium. The solid bodies can be positioned in a container having a first elastomeric membrane surface. Liquid can be introduced to mobilize the volume of particles. A master shape can be pressed into the membrane with atmospheric pressure. The resulting solid shape is a stable, force-resisting shape. The solid bodies and carrier medium form a reversible state-changeable mixture. The carrier medium can be a liquid or a gaseous froth. The shape can be a reformable mold or a reusable template to capture dimensions of impressed shapes for transfer to a mold.

In other aspects, a system is disclosed for holding a volume of particulate material inside an air and liquid-impermeable container with at least one elastomeric membrane surface; deaerating the volume; infusing the volume with a liquid to cause it to be mobile; pressing a master shape into the membrane via atmospheric pressure; and extracting the liquid through one or more screen elements which are placed in or adjacent to the particle volume. The extraction causes atmospheric pressure to press the particles against the contours of the shape and against each other. This pressure continues to hold the particles in place against the elastomeric membrane when the master shape is removed from the outer surface of the membrane. The system further has a means to heat and drive liquid from the particle volume and, in certain embodiments, to leave a residue of binding adhesive which locks the particles into a continuous force-resisting mass.

Operation of one embodiment is as follows with a particular embodiment of the container which has a rigid outside frame and a membrane face on the top and bottom surfaces. With the particle volume infused by liquid, a master shape is pressed against the top elastomeric membrane of the container by atmospheric pressure, thereby causing the shape to impress a complementary shape in the membrane. This pressing is accomplished through use of a flexible or elastomeric vacuum cap which is sealed over the shape and against the container's top surface membrane, following which air is evacuated from between the top membrane and the vacuum cap. Liquid is then extracted from the volume and the particles within the container are pressed together by atmospheric force which acts on all exterior surfaces of the tool-bed but in particular in opposed directions against the vacuum cap and the bottom surface membrane. Air is then introduced into the vacuum cap, the cap removed and the master shape removed from the formed surface of the elastomeric membrane.

In another embodiment, the container is formed against a master shape with the process of liquid infusion, a pressing action via atmospheric pressure and a liquid extraction process. This embodiment is essentially a flat envelope with a flexible outside rim and two opposed elastomeric membranes. To use this embodiment a master shape is placed on an air-impermeable surface, a membrane of the container is placed over the shape, and either a vacuum cap or a vacuum-bagging film is placed over the container to effect forming of the elastomeric membrane against the master shape. The envelope may also have a vacuum seal on its perimeter and so has the combined function of containing a mass of particles and of serving to extract air from between the master shape and the envelope.

In implementations, there can also be a combined use of the first and second containers described above. A master shape may be placed on the top elastomeric surface of the first rigid-framed container and then a membrane surface of the second container is placed over the shape. The second container fits inside the frame of the first container and a vacuum cap is placed over and sealed outside the second container against the surface membrane of the first container. When the volume under the vacuum cap is evacuated the master shape is pressed between the elastomeric sides or faces of the two containers. Liquid is then extracted so that the two volumes of particles are pressed together and against the membranes surrounding the contained shape; the vacuum cap is vented with air and removed; the top container is removed; and the shape is removed from the membrane of the bottom container. When the top container is again placed over the bottom container, a closed, shaped cavity is formed which is complementary to the entire surface of the master shape which was used to form the cavity.

In yet another embodiment, a combination of containers can be used in which two identical containers of either the first or the second type may be pressed together around a master shape without use of the vacuum cap. In this case the containers are joined and sealed by either a seal mounted on one or both of the containers or by seals mounted on a seal ring which fits between the two containers. The seal ring may be further employed to channel vacuum or air pressure between the two containers and to hold the master shape in a precise orientation and position between the two opposed containers. The seal ring may also furnish access to the formed cavity for the purpose of injecting a moldable material into the cavity.

In yet another embodiment of the container the container itself is formed into a replica of a master shape, or into a shape complimentary to a master cavity by another combination of the elements and processes described above. The exterior of this third type of container may be formed entirely from an elastomeric material or may be formed from a combination of elastomeric, flexible and rigid materials. Though the container might be shaped against a single surface, it can also be shaped over substantially its entire surface by confining it within a master cavity formed by two or more closely-fitting mold parts. Key to this forming process is an expansion means within the third container which presses the particulate material against the cavity walls.

In another embodiment, there is combined use of the containers which employ the three types of containers described above for a single purpose. The first or second types can be used to form a complementary cavity from a master shape. The third type of container can then be placed in the cavity, which is now used as a master cavity, and the third type formed complementary to the master cavity contours, thereby creating a replica of the original master shape.

It can be appreciated that there are numerous variations of containers and varied combinations of containers which can be employed either to form a surface which is complementary to the exterior surface of a master shape in part or in whole, or to form a surface or surfaces complementary to the interior contours of a hollow master shape or master cavity.

For instance more than one container of the first type (rigid frame) or second type (flexible-edge) can be employed to form a continuous surface complementary to a master shape's surface, with the elastomeric membranes of the containers either overlapping or being abutted together. Containers of the second type may also have a membrane and particle configuration that allows two or more of the containers to be "tiled" together to form a continuous surface of particle-backed membranes. Likewise two or more containers of the third type can be employed together to form a shape complementary to the interior of a master cavity.

In yet other embodiments, a forming system also includes a base station which provides evacuation of air, liquid infusion into and liquid extraction from the particle filled containers. The base station also furnishes vacuum forces to enable the forming operations to be performed on the various containers either singly or in combination. The base station comprises a liquid receiver; onboard vacuum system or provision to connect to an external vacuum source; an air compressor or provision for external connection to pressurized air; valves, fittings and tubing or piping to provide vacuum and to control the flow of liquids to and from the containers; an electrical power supply to operate the valves, process sensors and any onboard mechanical vacuum pumps and air compressors; and a menu-driven process controller to operate the base station.

In another embodiment, a forming system includes a heater which may be used to vaporize and drive out liquid from the particle filled containers, and further to heat any materials which may be used to recreate the contours of the original master shape through molding against the complementary surface of the formed elastomeric membrane. The vaporizing or drying process is especially advantageous when the liquid contains a soluble binder which remains on the pressed-together particles and locks the shaped volume of particles in place when the liquid has been driven out of the container. The heater may take numerous forms to include a radiant heater, a convective air heater, heating elements within the particle-filled container, and various types of inductive (e.g., microwave or radio-frequency) heaters. The heater may be powered and controlled by the base station and its controller, or the heater may be powered and controlled separately.

Next a reformable footwear making embodiment is detailed. In this system, the 3D model of the footwear as customized by the user or a doctor for the user is provided to a reformable shape object fabricator 1006, which is detailed next. The fabricator renders a physical model of the 3D model and then applies a state-changeable mixture that includes uniform, generally ordered, closely-spaced solid bodies and a liquid carrier medium, with the liquid filling any voids or interstices between the bodies and excluding air or gas bubbles from the mixture. Within the mixture, the solid bodies can be caused to transition from a near-liquid or fluent condition of mobility to a stable, force-resisting condition. To create mobility, a small excess quantity or transition liquid is introduced to create a fluent condition by providing a slight clearance between the bodies which permits the gently-forced introduction of at least two simultaneous slip planes between ordered bulk masses of the bodies at any point in the mixture. Transition to the stable condition is caused by extraction of the transition liquid, removing the clearance between bodies and causing them to make stable, consolidated contact.

The 3D shape generator to generate the insole or sole is a complete computer actuated system that is enclosed in the object fabricator. CAD data is downloaded by wire or wireless connection to the shape generator. Based on the desired dimensions, one embodiment of the 3D shape generator forms a 3D object by having an array of computer controlled moveable pins whose height is adjusted in accordance with the CAD design file, and the overall shape is smoothed by a Lycra sheet or felt sheet. The pins or rods lift the felt or Lycra sheet to form a 3D object based on the CAD design file. In this embodiment, an array of N×N micro hydraulic actuators can be used to form the shape. This embodiment is a dense hydraulic planar pin-rod matrix array. Another embodiment actuates an N×N pin-rod matrix driven by servomotors. In either case, each pin-rod is controlled individually, similar to pixels on a screen except that the pixel has height as well.

In one embodiment, the N×N matrix can be an array of electro-mechanical pins positioned in a frame. The frame is adapted to hold the plurality of pins in a parallel position to one another in a series of columns and rows, such that the distal ends of the plurality of pins together form a flat virtual plane. Each pin of the plurality of pins includes an elongated housing member defining a linear axis there through, and a pin member adapted to slide linearly in either direction along the axis. Each of the housing members includes an upper electromagnet, and a lower electromagnet separated from the upper electromagnet. Each of the electromagnet is adapted to move its respective pin member linearly in either direction. Each of the pin member includes a linear potentiometer, a, magnet and an electronic transmitter attached to an opposite end to the distal end, such that when each of the pin members are moved linearly each respective linear potentiometer sends a signal to its respective transmitter which in turn sends an electronic signal describing its movement within its respective housing member, a plurality of electronic wires respectively connected to each transmitter, such that electronic signals can be relayed to and from each respective pin; an analog-digital converter connected to the plurality of electronic wires and adapted to convert the analog electronic signals relayed by the transmitters into digital format to be transmitted, processed, stored, and then converted back into analog form for return transmittal to the set of pins. A processor is connected to the converter and adapted to retrieve the electronic signals from the converter, store them, and retransmit them back to the converter when desired, such that a user can displace the pin members from the virtual plane in any pattern, have electronic signals sent, processed, stored, and returned to the same set of pins, or another separate set of pins, at a later time to thereby displace the pins to the same positions as the original pattern chosen by the user.

In one embodiment, the pin array device has each of the housing member of each pin comprise an upper frame upper electromagnet, upper spring, lower electromagnet, lower spring and shield along the entire upper frame wall to separate magnetic field between each interactive pin. The lower frame consists of the outer fixed part of the potentiometer and electronic transmission from electronic transmitter to both electromagnets. The pin consists of a magnet, a mobile portion of the potentiometer, electronic transmitter that picks up all the wire and sends position signal and feeds the power to both electromagnets via the lower housing. The electronic signal may be a Pulse Width Modulation signal, and the displacement of each of the pin members is proportional to the strength of the Pulse Width Modulation signal received by the electromagnets.

While FIGS. 1F-1G show actuators or pins at predetermined locations for insole use, the pins can be part of a grid array for adjusting arbitrary dimensions. In one embodiment, the pins are moved by the action of a plate, common to all or a portion of the pins, that can extend and retract along a single axis of motion. A clutch mechanism cooperates with the moving plate to fix the pins at a desired position. In an exemplary embodiment, the shape generator 1004 can include a membrane covering the pins. A plurality of pins 1011-1018 arranged in an array such that respective head portions 1021-1028 associated with the pins collectively define a surface 1030. It will be appreciated that the area of array is not necessarily defined by two Cartesian dimensions. For example, the pins could be arranged along a spherical or hemispherical surface, with the array spanning the azimuthal and polar dimensions across the surface of the sphere. The position of a given pin (e.g., 1011) can be adjusted along an axis of motion.

In one embodiment, an optional motion plate 1032 can be provided to move the pins along the axis of motion as to adjust the position of the pins. The motion plate 1032 can be moved by reasonable mechanical or electromagnetic means. For example, the plate 1032 can be moved via an electrical motor, a hydraulic assembly, or one or more solenoid coils exerting a magnetic force.

A clutch mechanism 1034 is operative to arrest the motion of a given pin at a desired position. The respective positions of the pins can be selected to deform the display surface into a desired raised image. The clutch mechanism can comprise reasonable means for selectively arresting the motion of the pins. For example, the clutch mechanism 1034 can comprise components for mechanically or magnetically engaging the pins.

One embodiment provides an upper plate with a plurality of apertures through which corresponding pins forming the object's surface can pass. The pins can include head portions with areas larger than that of their respective apertures, to more fully tessellate the display surface and to help maintain the pins within the apertures. The upper plate can house part or all of a clutch mechanism that selectively engages one or more pins to maintain the pins at a desired position. The upper plate houses one or more banks of solenoids that shift the position of one or more portions of the clutch (not shown) that physically communicate with the pins. In an exemplary embodiment, the solenoids shift the position of one or more bars such that they contact or release circumferential grooves on the surface of the pins. This embodiment also provides a lower plate and a base plate disposed parallel to the upper plate along one or more support posts. A lifting plate can be suspended between the lower plate and the base plate on one or more guide posts. The lifting plate can be raised or lowered via a motor and belt system to adjust the position of the pins. For example, the pins can be reset to a fully raised position by raising the lifting plate to its maximum height. The movement of the guide pins and the action of the clutch mechanism can be regulated by a processor.

Figure 11:
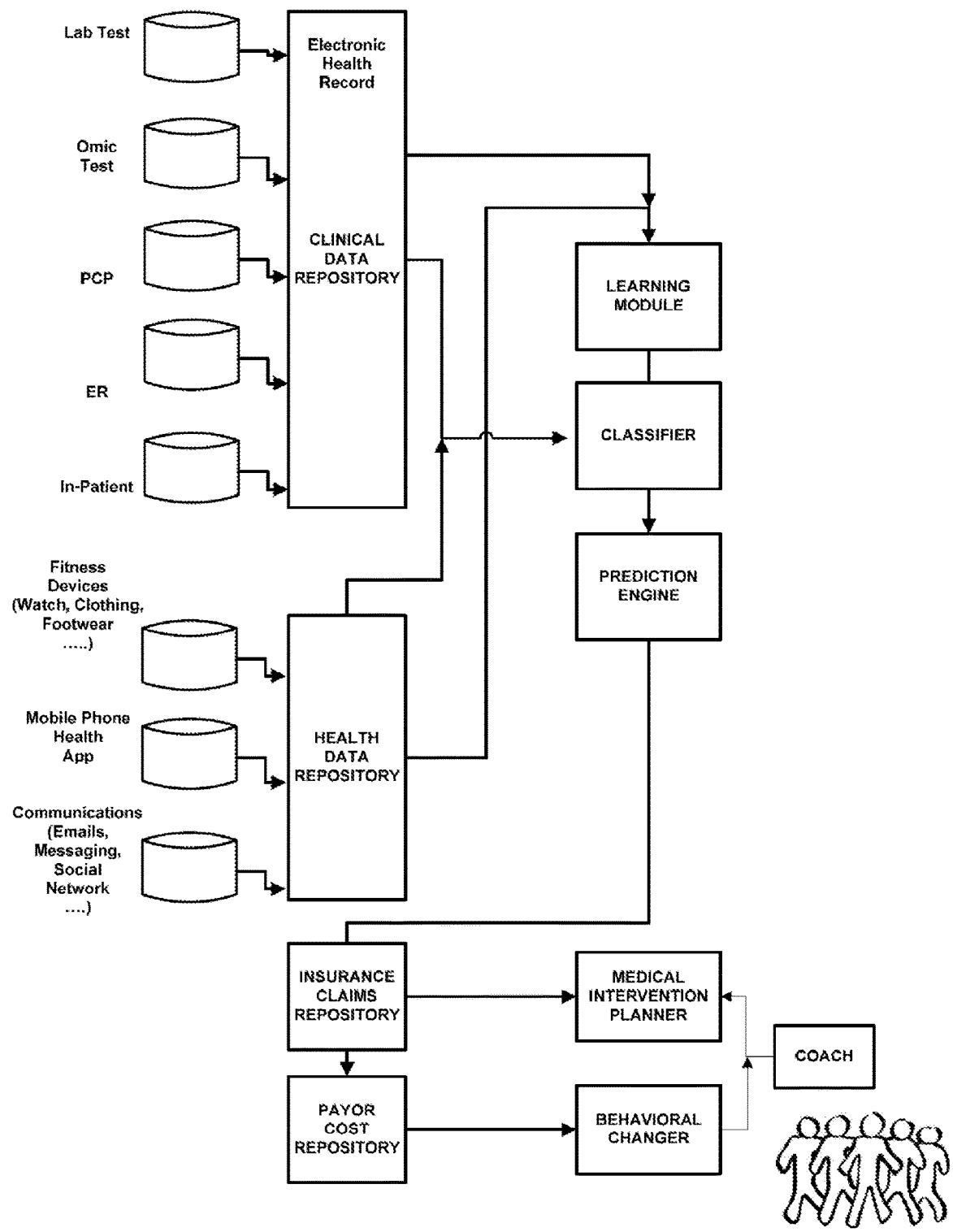
FIG. 11 shows an exemplary system for receiving health information from the user body and for mining health data as part of precision medicine.

As shown in FIG. 11, two facing and opposite bed of pins 2210-2212 can form a 3D shape for the sole or insert. The insert and/or the shoe can be produced in discrete sizes such as US sizes 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, and 18, for example. Thus, a plurality of sized beds can be used, or one large pair of beds covering size 20 can be used to produce all other smaller sizes. Turning back to FIG. 1H showing one of the beds 2210-2212, the selected view of the 3D object creator comprises one row of four pins 2102-2108. It will be appreciated that a functioning computer controlled 3D object creator can contain a large number of pins arranged across multiple rows in order to reproduce the shape of the 3D object with high fidelity.

In an exemplary embodiment, the rows containing the pins 2102-2108 are staggered as to form a honeycomb pattern. Accordingly, the pins 2102-2108 are arranged in a plurality of linear rows and one or more staggered columns. Alternatively, the pins can be arranged in a Cartesian grid, such that both the rows and the columns are linear. It will be appreciated that other methods of arranging the pins can be utilized, and that the placement of the pins will vary with the necessary size and spacing of the pins, as well as the desired shape (e.g., flat, spherical, recessed) of the array.

In the illustrated display, the pins 2102-2108 have respective cap portions 2112-2118 that define a raised surface. The cap portions 2112-2118 can be covered by an elastic membrane or felt layer 2120 to provide a relatively smooth surface for the object. The use of the pin caps 2112-2118 and the membrane 2120 will depend on the application. The pins 2102-2108 pass through respective apertures in a stationary, outer plate 2124. The outer plate 2124 houses a clutch mechanism 2126 that acts to maintain the pins in their desired positions. In an exemplary implementation, the clutch mechanism 2126 can comprise a series of row bars and column bars having two associated positions. In a first, open, position, a given bar allows the pins within its associated row or column to move freely. In a second, restraining, position, the bar is moved to physically contact the pins at one of a plurality of evenly spaced grooves on the pin, maintaining the pin at its position. The spacing of the grooves corresponds to a desired resolution of the display 2100. The position of the bars can be changed via one or more banks of solenoids. In an exemplary embodiment, the bars are biased, by a spring or similar mechanism, to remain in the restraining position, until a solenoid is actuated to move the bar into an open position.

During operation, the pins can be reset into a fully extended position by a reset plate 2130. The reset plate 2130 can then be incrementally withdrawn to allow the pins 2102-2108 to retract toward the interior of the display device. In an exemplary embodiment, the reset plate 2130 is moved by a motor and belt arrangement. The pins 2102-108 have associated springs 2132-2138, with each spring (e.g., 2132) attached at a first end to the underside of the outer plate 2124 and at a second end to the end of the pin (e.g., 2102) opposite the cap portion (e.g., 2112). When the pins 2102-2108 are fully extended, the springs 2132-2138 are compressed against the underside of the outer plate 2124. The springs 2132-2138 thus provide a tensive force on the pins 2102-2108 as to draw the pins toward the interior of the object being formed.

The movement of the reset plate 2130 and the operation of the clutch mechanism can be coordinated by a controller 2140 to adjust the position of the pins 2102-2108. The controller 2140 can provide information relating to the desired pin positions to the projector. The reset plate 130 can be incrementally withdrawn toward the interior of the object. In an exemplary embodiment, the reset plate 2130 withdraws in increments equal to the spacing between the grooves on the pins 2102-2108. After each retraction of the plate, the clutch mechanism 2126 can be selectively activated to release one or more of the pins, while leaving others secured. The tensive force provided by the springs 2132-2138 pulls the ends of the released pins flush against the reset plate 130, such that the released pins retract to a uniform level defined by the position of the reset plate. The secured pins remain at their previous level. The pins are then resecured by the clutch mechanism, and the plate is retracted by another increment. This process is repeated as the reset plate 2130 retracts to leave each pin at a desired level of extension.

In another embodiment, the pins pass through respective apertures in a stationary, outer plate housing a first portion of a clutch mechanism that acts to adjust the pins into desired positions. In an exemplary implementation, the first clutch portion can be piezoelectric restraints for the plurality of pins. In a default position, a given restraint loops around its associated pin, but allows the pin to move freely. Upon the application of an electrical current, the restraint contracts as to physically contact its associated pin at one of a plurality of evenly spaced grooves on the pin. This fixes the pin to the outer plate, maintaining the pin at a stationary position. The spacing of the grooves corresponds to a desired resolution of the 3D object being formed. The pins also pass through respective apertures in a moving plate which can be moved by a motor and belt arrangement. The moving plate houses a second portion of the clutch mechanism with piezoelectric restraints for the plurality of pins. The movement of the moving plate and the operation of the first/second clutch portions can be coordinated by a controller to adjust the position of the pins. The moving plate oscillates in a direction normal to the outer plate and a base plate between a first position, closest to the base plate and a second position, closest to the outer plate. In an exemplary embodiment, the first position and the second position are separated by a distance equal to the spacing between adjacent grooves. The pins begin in a default position, fixed to the outer plate by the first clutch portion. In an exemplary embodiment, the default position of the pins is a fully withdrawn position (e.g., the first clutch portion engages the uppermost groove of each pin). Since the default position of the pins is known, the controller can determine the distance between the default position and a desired position as a number of increments, as defined by the groove spacing of the pins. The controller can thus select one or more pins to extend by one or more increments. While the moving plate is in its first position, the selected pins are released by the first clutch portion. Simultaneously, the second clutch portion engages the selected pins, such that the pins are fixed to the moving plate. The moving plate can then be moved to its second position. Once the plate reaches the second position, the second clutch portion releases the selected pins, while the first clutch portion reengages the pins. It will be appreciated that the motion of the moving plate can be controlled by the controller such that the first clutch portion can engage the pins at a groove one increment below the default position. Accordingly, the selected pins are extended by one increment. This can be repeated a number of times, to allow one or more pins to be moved to a desired position up to a maximum extension. The final position of each pin will be determined by the number of times the first and second clutch portions are activated for the pin. This can be controlled by the controller according to the desired position of the pin. Once the pins have been positioned, the controller can direct the object fabricator 1006 to copy the 3D object formed by the pin grid 3D shape generator.

In another exemplary clutch mechanism, a pin can be encased in a solid restraining material having a low melting point. For example, the restraining material can be an alloy of lead and one or more other metals. The restraining material is contained in a container having a relatively high melting point. The clutch mechanism disengages by applying heat from a heat source to the restraining material in order to bring it to a liquid state. The heat source can be applied by a laser apparatus (not shown) directed on the restraining material or by a heating element associated with the container. In an exemplary implementation, the container is the heat source, producing resistive heat upon the application of an electrical current. While the restraining material is in a liquid state, the pin can move freely through the aperture. Once the heat source is deactivated, the restraining material cools and returns to a solid state, restraining the pin.

In yet another exemplary clutch mechanism, a wire has shape memory properties is looped around a pin. The material with shape memory properties has the ability to return to an imprinted shape when heated. A desired shape can be imprinted into the material by molding the material at a high temperature and maintaining the desired shape as it cools. Below a threshold temperature, the material is relatively flexible and can be deformed away from the imprinted shape with relative ease. Once the material is heated above the threshold temperature, however, it reverts back to the imprinted shape with some force. In an exemplary implementation, the wire is a formed from nitinol, an alloy of nickel and titanium. The wire is shaped such that the loop is opened around the pin and the pin can move freely through the loop. A current can be applied to the wire to heat the wire via resistive heating to a temperature greater than its threshold temperature. This causes the wire to return to its imprinted shape, engaging the pin as the loop closes. The wire returns to its imprinted shape somewhat forcefully, such that the tensive force on the ends of the wire is insufficient to restrain it. In an exemplary embodiment, the wire is looped around a groove in the surface of the pin to facilitate engagement of the pin. When the current is no longer applied, the wire 352 cools and returns to its more malleable state. Once the wire cools below threshold, the tensive force applied can once again deform the wire into an open shape, releasing the pin.

Figure 1J:
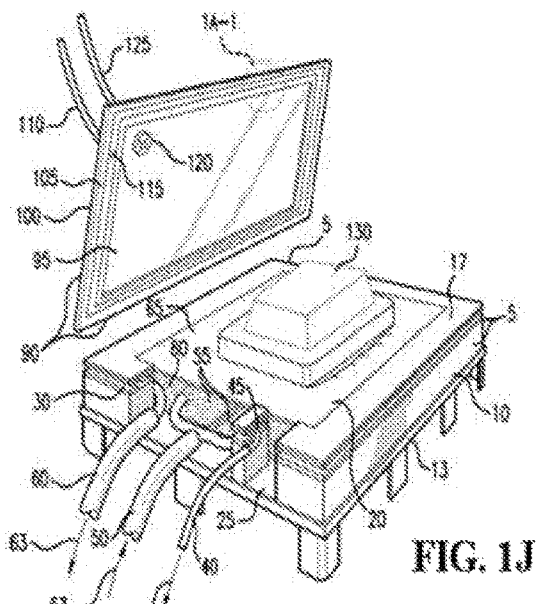
FIGS. 1J, 1K, 1L, and 1M show a first container embodiment, a master shape and a vacuum cap, and further show a sequence of operations to create a shaped impression, complementary to the master footwear shape, in the surface of one elastomeric membrane face of the container.

FIGS. 1J, 1K, 1L, and 1M show a first container embodiment, a master shape and a vacuum cap, and further show a sequence of operations to create a shaped impression, complementary to the master shape, in the surface of one elastomeric membrane face of the container. Turning now to FIG. 1J, a container 5 is shown with a rigid container frame 10 and elastomeric top and bottom membranes 20 and 25, resting on a base 13 which separates the bottom membrane 25 from contact with any surface that the base 13 and the container 5 rest on. The top membrane 20 is bonded to a perimeter frame 17 so as to have an air-tight interface between the container frame 10 and the membrane 20. The container frame 10 is affixed to a continuous vacuum-activated seal 30 which is bonded to the container frame 10. The seal 30 is resilient and acts much like a suction cup to hold the perimeter frame 17 to the container frame 10. The bottom membrane 25 is bonded directly to rigid container frame 10 since the membrane 25 is not a working surface wearer to damage, in contrast to the working surface of membrane 20 which is subject to damage. In one embodiment, the bottom membrane 25 can be affixed by a perimeter frame and vacuum seal as described above. In yet another embodiment with more complexity, mechanical clamps and a pressure seal can be employed to affix either top or bottom membranes. Tubes 40, 50 and 60 penetrate a toolbed or a container frame 10. The tube 40 communicates with a seal 30 through an opening 45, and the seal 30 affixes the membrane 20 to the container 5 by a vacuum (indicated by arrow 43) acting through the tube 40. The vacuum seal 30 can be inactivated by introducing air through the tube 40, allowing the membrane 20 and the frame 10 to be removed in order to insert or remove a volume of particles from the container 5, or to replace a damaged membrane 20 or internal screen element. The tube 50 communicates with a main particle screen 55 which is overlaid with a volume of particles 80. Arrow 53 indicates the flow of liquid into the particle volume through screens 55. The particle screens 55 serve to hold all particles in the container 5 while allowing liquid to flow in and out of the particle mass. There is a double layer construction of both screens 55 with the tubes 50 and 60 communicating between the layers. The particles cannot penetrate the outer layers of the screens and so do not move into the tubes as air is evacuated or liquid extracted. Detail 57 shows extensions of tubing 50 penetrating into the center of the double-layered screens. The extensions have perforations that enable distributed liquid flow along the length of the tube inside the screen. The tube 60 communicates with a rim evacuation screen element 65 which follows the entire inside upper perimeter of frame 10 and is likewise perforated along its length within element 65. Arrow 63 points outward to indicate deaerating vacuum force acting on the container volume via the evacuation element.

Turning now to the top of FIG. 1J, a vacuum cap 90 is shown with a continuous flexible or elastomeric membrane 95 bonded to another perimeter frame 100, the frame also having a continuous vacuum-activated seal 105 bonded to the frame 100. The seal 105 is identical in design and function to the seal 30. The vacuum cap 90 has a tube 110, which communicates with the vacuum seal through an opening 115, and a tube 125 which in turn communicates with the underside of membrane 95 through a port 120.

A master shape 130 is shown resting on membrane 20. The master shape will used to form a shaped impression in the membrane as described next. To prepare for the forming process, a membrane 20 is sealed to the container; air is removed from the volume of particles as shown by arrow 63; and liquid is introduced into the particle volume as shown by arrow 53. Liquid flow is cut off when there is sufficient liquid to allow particles to move in relation to adjacent particles as displacing force is exerted on either the top or bottom membrane of the container.

Figure 1L:
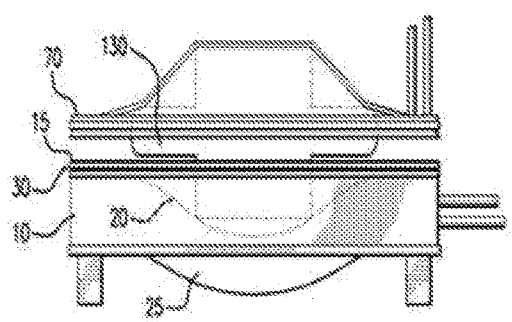
Figure 1K:
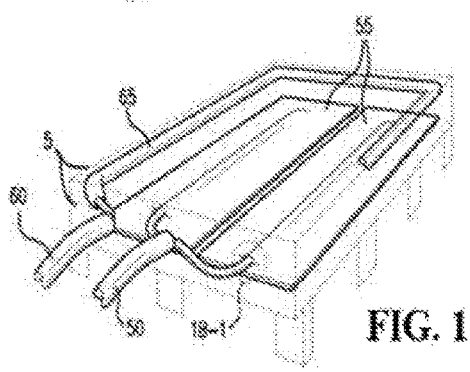
Figure 1M:
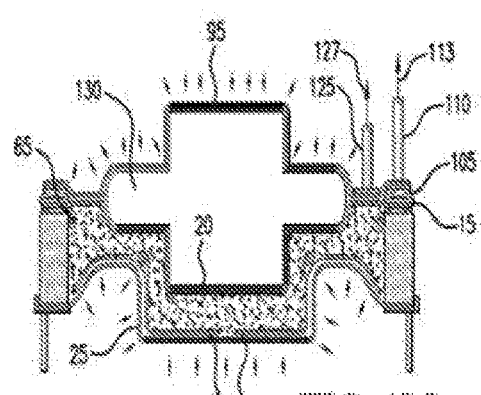

FIG. 1K shows a side view of the container frame 10 with a vacuum cap 70 resting over the master shape 130 prior to being sealed against the membrane perimeter frame 15 to which the membrane 20 is bonded, with the membrane affixed using the seal 30 to the container frame 10. The master 130 is resting on the unformed surface of membrane 20 with the movable particles between membranes 20 and 25.

FIG. 1L shows a cutaway view with the vacuum cap 90 affixed by the seal 105 against the perimeter frame 15 by vacuum through the tube 110 as shown by an arrow 113. In addition the space between the vacuum cap membrane 95 and the top membrane 20 has been evacuated through the tube 125 as shown by an arrow 127. The vacuum cap membrane 95 is pressed down against the master shape 130 and against the surface membrane 20 by atmospheric pressure which also acts oppositely against container bottom membrane 25. Liquid is then extracted by a pump or vacuum from the particle volume through a tube (not shown) through the particle screen 55, causing atmospheric forces acting on bottom membrane 25 to pack the particles against top membrane 20 which is forced against the master shape since air has been evacuated from between the vacuum cap membrane and top membrane 20. Any leakage of air into the container, which would add atmospheric pressure back to the container and so reduce the packing force on the particles, can be removed by continuing vacuum extraction of liquid through particle screens 55 or by vacuum extraction through the perimeter evacuation screen element 65.

When the master shape 130 is removed from the surface of the membrane 20, an impressed shape 135 remains which is complementary to the shape 130. The differential pressure on the container by vacuum extraction is continued, thereby maintaining opposed atmospheric forces that act to keep membranes 20 and 25 pressed against the particles and so immobilizing them to keep the impressed shape stabilized. In form the seal is a continuous channel with the legs angled outward. The channel has a single opening and a vacuum and vent tube connected to it as described with reference to FIG. 3A. The material of the seal is resilient since the legs will be pressed against a surface and must conform to and seal against the surface. The legs are separated by a sufficient distance that they will be pressed into contact with the surface by atmospheric pressure with a greater force per unit area than atmospheric pressure. In function, when the legs of the channel are pressed against a smooth surface and the vacuum introduced inside the channel, the seal legs deform against the surface and the deformed area is substantially less than the area inside the channel In experiments a ratio of deformed area to inside area of 1 to 2 has been shown to be very effective in sealing against a smooth surface if the durometer of the seal's elastomeric material is around 40. In operation the seal is simply placed against or gently pressed against a smooth air-impermeable surface. A vacuum is introduced through the tube, extracting air from within the seal and so enabling atmospheric pressure to force the seal against the surface. Any leakage from atmosphere outside the seal is scavenged by the vacuum and so does not enter the volume inside the perimeter of the seal even if a full vacuum is imposed on that volume. To release the seal air is introduced via the tube or a small blade can be slipped between the seal and surface to break the internal vacuum.

The particles can be a reversible state-changeable mixture having a plurality of solid bodies and a carrier medium, with the carrier medium filling any voids or interstices between the bodies. Within the mixture, the solid bodies can be caused to transition from a formable state, preferably a near-liquid or fluent condition of mobility, to a stable, force-resisting condition through introduction and then extraction of a slight excess quantity of the carrier medium beyond that required to fill the interstices of the bodies when closely packed. In most embodiments, the carrier medium is a liquid preferably excluding any air or other gases from the mixture, and most of the discussion will revolve around such embodiments. However, some embodiments use a carrier medium that is a liquid-gas froth.

The mixture can be rapidly shifted from a formable (preferably near-liquid or fluent) state to a stable force-resisting state and back again to the formable state, through slightly altering the carrier-solid proportions of the mixture, and the system further provides methods and apparatus for using the mixture. Embodiments are characterized by one or more of the following advantages: the ability to pressurize a mixture and drive it against a complex surface as if it were a liquid; the ability to create a "near-net" or extremely accurate representation of a shape due to the negligible volumetric change that accompanies a state change; the ability to effect the state-change with a very small volume of single-constituent transfer and with consequently small actuation devices without the need for a vacuum pump, without chemical reactions, and with no need for thermal or electrical energy to be applied to the mixture; the ability to greatly alter the volume of any elastic or otherwise dimensionally changeable container, envelope or chamber through the free-flowing transfer of the mixture from one container to another; and the ability to tailor the mixture to satisfy a wide variety of physical specifications in either the flowable or the stable state.

The mixture can be used in reformable molds or other shaping tools, and in reusable templates that capture the dimensions of impressed shapes for transfer to a mold. The mixture can also be used in any product or shape that benefits from the incorporation of arbitrary reformability or precise reconfigurability. The mixtures further provide useful properties for use in a wide range of shock-absorbing, leveling, protective and supportive elements or apparatus.

The mixture in its formable state may be loosely compared to quicksand, while the mixture in its stable state may resemble hard-packed sand or even cement, with the transition being caused by the transfer of a relatively small amount of liquid. Hence the mixture, while in the formable state, includes enough liquid to fill the interstices between the nested solid bodies, and an excess amount of liquid that is referred to as the transition liquid. In the stable state the transition liquid is absent and the bodies are completely packed or nested.

In preferred embodiments the solid bodies are uniform, generally ordered, and closely spaced, with the predominate mass of the bodies close-packed and touching. To create mobility, the transition liquid is introduced in just-sufficient quantity to create a fluent condition by providing a clearance between some of the bodies, which clearance permits the introduction of at least two simultaneous slip planes between ordered masses of the bodies at any point in the mixture. The bodies themselves separate freely from one another under movement of the liquid and without turbulent mixing, and shift relative to one another generally in ordered bulk masses. The bodies should be of a density that is close enough to that of the liquid to permit flow of the bodies along with the liquid, or should have a size or structure that facilitates movement of the bodies along with the liquid.

In an embodiment, the surface of the mixture while in the formable state is first made to conform to a desired shape. The bodies in the mixture are then caused to transition from the fluent condition to the stable condition through extraction of the transition liquid. This extraction removes the clearances required to provide slip-planes between ordered masses of the solid bodies, thereby causing the bodies to make nested, packed, interlocking or otherwise stable consolidated contact. The mixture, now in the stable state, has a surface that conforms to the desired shape.

The mixture can be used in molds, templates or other products through holding the mixture in, or transferring quantities of the mixture while in the fluent condition into and out of variable-contour or variable-volume containers or chambers. The mixture can be stabilized by removal of the transition liquid, which may cause an elastic membrane to be pushed against the consolidated bodies by ambient pressure, or by transition liquid removal that causes the solid bodies to pack together under liquid tensile forces, thereby creating an ordered, deformation-resisting structure through surface friction or through surface adhesion of one body to another.

In certain embodiments, the mixture can be held inside a container or transported into a container with a flexible, elastically deformable and stretchable wall. The process then extracts the transition liquid from the mixture so as to cause body-to-body contact and force-resisting stability through pressure external to the container acting on the confined, ordered, abutting bodies. Transfer of fluent mixture into and out of the containers, or displacement of mixture within the containers can be accomplished by pressure forces within the mixture, with these forces being distributed uniformly throughout the mixture by the liquid carrier medium.

This distribution of uniform pressure against the surface of each body, coupled with the clearance volume furnished by the transition liquid, assures that the bodies are not forced against one another while the mixture is in the fluent condition. This elimination of body-to-body compression forces in turn prevents the bodies from sticking together and resisting displacement while the mixture is in the fluent condition. Pressure forces in the liquid can be exerted through pressing a shape against an elastic, stretchable membrane that constitutes at least one surface of a chamber substantially filled with the fluent mixture, or such forces within the liquid medium of the fluent mixture may be induced by a two-way pump or other transfer system.

The bodies themselves may have various geometries and may be provided within a state-change mixture in one uniform type, or there may be two or more types or sizes of bodies dispersed or layered within a mixture. For example spherical bodies of one size might have smaller bodies filling the interstices between the larger bodies, or a layer of short fiber bodies might float above a layer of spherical bodies. Flake-like bodies can be also be used, in which case the flat faces of the bodies can be pressed against one another to create a force-resisting body mass. The flat faces provide many times the contact area of abutting spheres, with accordingly higher friction or adhesion potential when consolidated against one another. If the flakes are in the form of a laminate that has one side heavier than the carrier medium and one side lighter, and if the flakes are closely spaced and in a medium which suppresses turbulence and solid body tumbling, the bodies will tend to be supported in, and to be consolidated in, an ordered parallel configuration. In this case, as with the spherical bodies, the transition liquid quantity will be just sufficient to create shear motion of body masses under low displacement forces.

Mixtures with more than one type or size of body can be used with the bodies either intermingled or layered separately, as by differing densities or the inability of bodies of one layer to pass through bodies in the adjacent layer. Bodies of different sizes or types may also be separated from one another by flexible or extensible porous materials or fabrications that allow passage of liquids but not of the confined bodies.

The degree of accuracy or irregularity on the surface of a stabilized mass of the mixture is dependent upon the relationship between the fineness of the bodies and the dimensions to be captured, a covering membrane's thickness and conformability, and the size and degree of regular packing order of a state-change mixture's solid bodies. If the bodies are very small compared to the contours of a shape that is to be replicated, or if the interstices between larger bodies in the mixture are filled by such smaller bodies, the mobile solid bodies of the mixture will consolidate and assume a near-net shape relative to any impressed shape when the transition liquid is extracted from the mixture.

In additional embodiments, the mixtures are stored external to one or more molds, tools or fixtures, and are selectively introduced, stabilized and made fluent again in the tools. Formulas of the mixtures or solid bodies and liquids of the mixtures may be stored separately, and may be mixed or separated as required for effective operation of separate elements of a forming or tooling system.

In yet other embodiments, flexible elements containing state-change mixtures are used to capture exterior or interior contours of a shape and to transfer the contours to other state-change elements. Through such "templating" operations a negative of a shape or surface may be produced and then a shape or surface identical to the first may be produced by forming the surface of a mixture against the transfer template. Individual elements might also be used to transfer portions of one shape to another shape and so create variations that combine the contours of two or more shapes into a single shape.

In still other embodiments, several elastic, extensible elements filled with state-change mixtures slide freely upon one another and relative to the contained mixtures in order to conform to highly contoured shapes. These embodiments would be used when the elastic stretch of a single membrane element is not sufficient to capture details of a shape.

Further embodiments include methods of displacing fluent mixtures within variable-volume flat elastic envelopes by pressing the envelopes against shapes with exterior air or liquid pressures, or pressing with physical elements such as bundles of rods or fingers that slide relative to one another. The pressing force pressurizes the liquid carrier medium and causes the envelopes to extend and conform to the shapes as the contained fluent mixtures flow within the envelopes under the uniformly distributed pressure forces within the liquid. Embodiments also contemplate the creation of hollow voids within a mixture-containing envelope, with the impressed shape causing the collapse of the voids so that the mixture need not be pumped into and out of a chamber to permit capture of a shape.

Yet other embodiments include methods for creating a sculptable condition in specific state-change mixtures through placing the mixtures in a quasi-stable state. The solid bodies are held in contact by extraction of a portion of the transition liquid, yet have sufficient lubricity or low contact friction to be displaced relative to one another by externally imposed forces. The bodies can be displaced into voids created within a mass of the quasi-consolidated mixture, or can be progressively displaced along the surface of the mixture from one region of the mass to another. In some embodiments, properties of flow of the mixture and the resistance to deformation of the abutted bodies are predetermined so as to be a function of the imposed external forces, and so to be subject to variable control that allows intermediate quasi-stable, sculptable or displaceable conditions within or on the surface of the bulk mixture.

State-change mixtures may also use solid bodies along with a state-changeable liquid carrier medium. The method for changing the mixture from fluent to stable and back again is, as described above, through transfer of a small amount of excess liquid; however, the mixture can be further solidified by changing the state of the carrier medium from liquid to solid.

In yet another embodiment, a state-change mixture is consolidated within a mold chamber and the liquid carrier or a second liquid component is circulated while held to a pressure below ambient. Through heating and cooling of the circulating liquid, the mold itself can be heated or cooled.

Still another embodiment of the state-change mixture has solid bodies that are hollow and very light, and a carrier medium comprising a liquid-gas froth of similar density. The froth is destroyed when extracted since the gas within it expands and separates from the liquid component; then the froth is reconstituted from the liquid and gas and reintroduced into the body mass to recreate a fluent mixture. The liquid component of the froth may be a solvatable (solvent-releasable) adhesive that can be dried to hold the consolidated bodies together and then re-dissolved by the frothed carrier medium. Very light bodies can also surrounded by a denser liquid, with the mixture likewise becoming fluent and then stabilized with transfer of a small quantity of transition liquid; however, the tendency of the bodies to adhere together under contact pressure is preferably countered, or liquid-like transfer of the mixture, especially through small lines or passages, becomes difficult if not impossible.

In additional flat envelope embodiments internal and external elements improve their functioning as lightweight tooling and templates. Included are methods to support these mixture-containing envelope structures, both internally with flexible reinforcements and externally with tubular 'foot' structures that also contain state-change mixtures. The flat envelopes may also be backed or supported by liquids or dry media with the ability to capture precise impressions of a shape with the ability to be switched from a liquid-like state to a firm state, or even to a fully hardened state that resembles concrete yet can be returned to a formable condition.

The state change from liquid-like to solid-like properties within the mixtures is effected by the transfer of a small amount of excess carrier medium, the transition liquid, into and out of the mixtures. When the transition liquid is present, preferably in just-sufficient quantity to create the degree of support and clearance that provides for at least two slip-planes, the solid bodies have a degree of mobility similar to that of the liquid medium of the mixture. The slip-plane condition of mobility can be generated through very small liquid pressure differentials or through externally imposed forces that displace the carrier liquid and the supported bodies along with the liquid. Ordered bulk masses of the bodies can shift relative to other ordered masses at any point within a continuous volume of the mixture, and the location of the slip-planes can fluidly shift under any slight differential force transferred from one body to another. It is preferred to prevent frictional contact between bodies during such force transfer by having the liquid medium of the mixture furnish a viscous or 'streaming' resistance to contact, and also for the medium to furnish a degree of body-surface lubrication so that light body contacts do not create friction between bodies.

Lubricity under high contact forces, as is required for many lubricating media, is not necessary within the mixtures since the bodies are in effect free-floating during flow, with any imposed liquid pressure forces being uniformly distributed against the surface of each body. For example a nearly ideal aqueous liquid medium can be formed by dissolving a small quantity of a soluble long-chain polymer such as polyethylene oxide into water. The medium carries solid bodies of a similar density without turbulence and friction-producing contact, allows the bodies to make non-lubricated surface contact when the medium is extracted, and causes the bodies to readily separate when the transition liquid is reintroduced.

When the transition liquid is extracted so that the solid bodies are in a stable configuration with ordered, packed and consolidated contact, the degree of resistance to externally imposed forces depends on such tailorable, engineered physical properties as body shape, body elasticity and compressibility, body surface properties of roughness, smoothness or natural molecular adhesion, residual adhesiveness or lubricity of the liquid medium on the contacting surfaces, surface tension of the medium, and variations of liquid medium or body properties with changes of temperature or pressure; alteration of the resistance properties through replacement of the first liquid with a second liquid medium, rinsing of the bodies and the first medium with a second or sequential liquid media, vapors or gaseous fluids; and any other engineered variations in the bodies and first liquid medium, and in other sequential introductions of various fluids into the mixtures or through the consolidated bodies. Any adhesive or clinging contact between the bodies is preferably relieved through polar molecular action of the first liquid medium, or through an intermediary treatment with other liquids or fluids prior to reintroduction of the first liquid medium.

The container works with quickly reversible state-change mixtures which can be rapidly shifted from a near-liquid or fluent state to a stable force-resisting state through slightly altering the liquid-solid proportions, and the system further provides methods and apparatus for utilizing the mixtures. Embodiments are characterized by one or more of the following advantages: the ability to pressurize a mixture and drive it against a complex surface as if it were a liquid; the ability to create a "near-net" or extremely accurate representation of a shape due to the negligible volumetric change which accompanies a state change; the ability to effect the state-change with a very small volume of single-constituent transfer and with consequently small actuation devices, with a low-energy mechanical actuation, and without requiring a vacuum pump, thermal, chemical or electrical energy to be applied to the mixture; the ability to greatly alter the volume of any elastic or otherwise dimensionally changeable container, envelope or chamber through the free-flowing transfer of the nearly solid mixtures from one container to another; and the ability to tailor the mixtures to satisfy a wide variety of physical specifications in either the flowable or the stable state.

The mixtures can be employed in reformable molds or other shaping tools, and in reusable templates which capture the dimensions of impressed shapes for transfer to a mold. The mixtures can also be used in any product or shape which benefits from the incorporation of arbitrarily reformability or precise reconfigurability. The mixtures further provide useful properties for but are not limited to application in a wide range of shock-absorbing, leveling, protective and supportive apparatus.

It can be appreciated that there are numerous variations of containers and varied combinations of containers which can be employed either to form a surface which is complementary to the exterior surface of a master shape in part or in whole, or to form a surface or surfaces complementary to the interior contours of a hollow master shape or master cavity. For instance more than one container of the first type (rigid frame) or second type (flexible-edge) can be employed to form a continuous surface complementary to a master shape's surface, with the elastomeric membranes of the containers either overlapping or being abutted together. Containers of the second type may also have a membrane and particle configuration that allows two or more of the containers to be "tiled" together to form a continuous surface of particle-backed membranes. Likewise two or more containers of the third type can be employed together to form a shape complementary to the interior of a master cavity. More details on the reformable manufacturing are disclosed in commonly owned patents to Jacobson et al including U.S. Pat. No. 6,398,992 and Pub. No. 20050035477 and 20070187855, the contents of which are incorporated by reference.

The footwear can be custom produced at the request of a customer, who can specify the nature of the customization for one or more pairs of footwear. Each shoe of a pair of the footwear may have a different design, message or message portion designed into it and rendered using the bed of pins described below to make the custom shoe design messages or shapes, and then the bottom sole can be fabricated using the reformable bed described below. Once the negative is fixed in the reformable bed, suitable materials for the bottom sole can be deposited and cured and can include rubber, plastic, or foam. Further customization can be done by a Computerized Numerical Control (CNC) where component design can be integrated with computer-aided design (CAD) and computer-aided manufacturing (CAM) programs. The device can be programmed to use a number of different tools-drills, saws, and so on. Alternatively a number of different machines can be used with an external controller and human or robotic operators that move the component from machine to machine. Regardless, a series of steps needed to produce a part can produce a part that closely matches the original CAD design in a highly automated fashion. In accordance with aspects of the subject matter disclosed herein through the use of reformable bed and a suitably programmed CNC tools, customized footwear with custom cut sole designs, can cost effectively be created in small quantities and yet scalable for mass-customization.

Composite Sole/Insole

The insole/sole can be a composite material. A composite material (also called a composition material or shortened to composite) is a material made from two or more constituent materials with significantly different physical or chemical properties that, when combined, produce a material with characteristics different from the individual components. The individual components remain separate and distinct within the finished structure. The new material may be preferred for many reasons: common examples include materials which are stronger, lighter, or less expensive when compared to traditional materials.

Figure 1N:
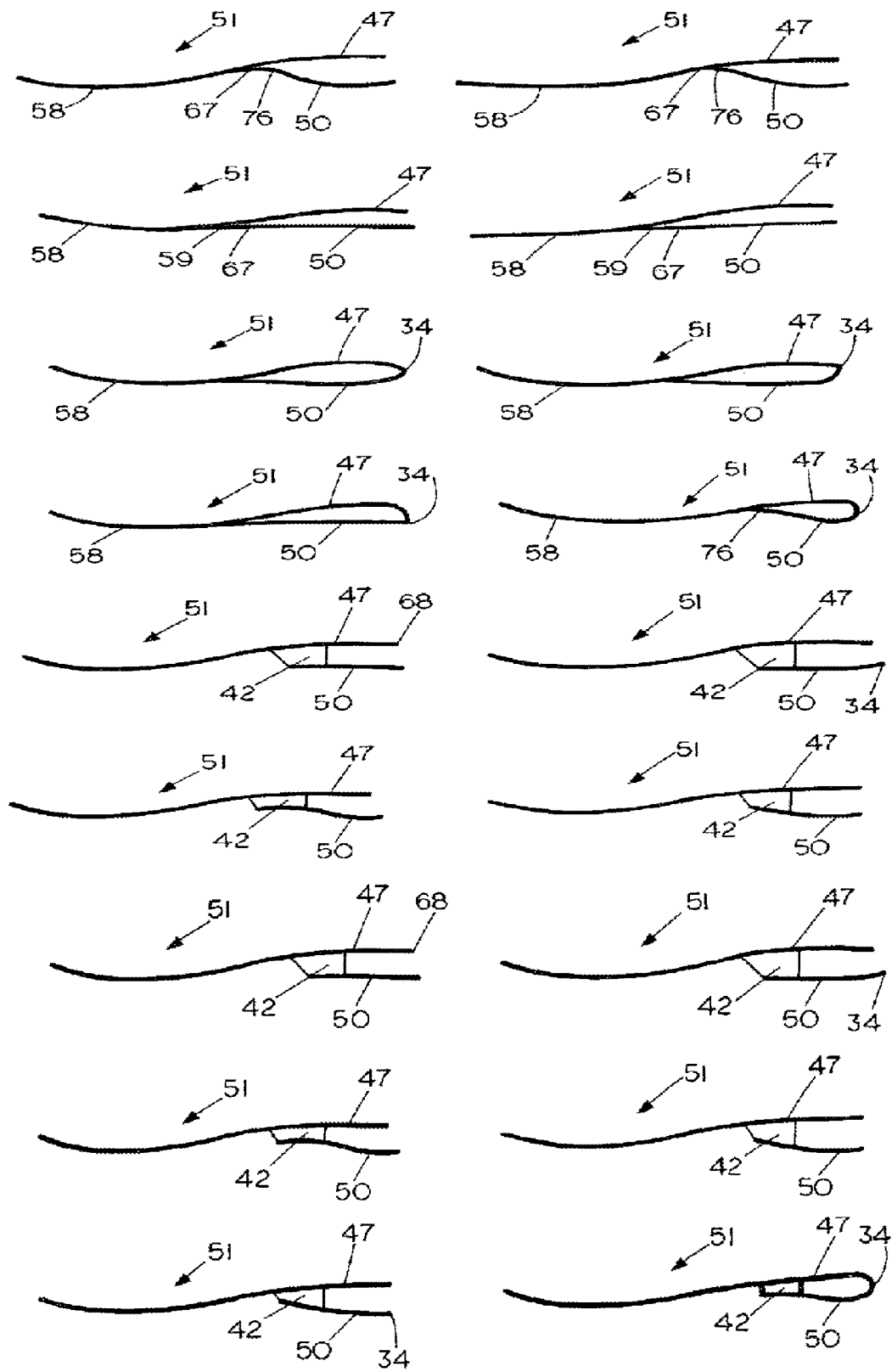
FIG. 1N shows exemplary composite insoles with shock absorbing springs at the bottom.

FIG. 1N shows various medial side views of a spring element that is formed by using the composite material for strength. The spring element can be a leaf spring formed of a composite material which is aerospace grade to provide resilience and long lasting spring. In one embodiment, the above sand printing system provides lightweight, low thermal-capacity reformable tooling for high-performance composite processing evaluation, parts prototyping, trial production and full-rate production of polymer matrix composites (PMCs) footwear components. For example, reinforcement can be glass fiber, carbon fiber, Kevlar fiber, natural fiber, ceramic fiber, particulate of nano materials. The resin can be polymer, metal, or ceramic.

Optimized tooling would provide a ramp-up rate consistent with the heatup rate of the composite material, while providing the strength to withstand the process temperatures and pressures. Going down the first row, spring element 51 consisting has a superior spring element 47 including toe spring in the forefoot area 58 and an inferior spring element 50 including a compound curved shape forming a concavity 76 in the midfoot area 67. Next is a spring element 51 having a superior spring element 47 that is relatively flat in the forefoot area 58 and an inferior spring element 50 including a compound curved shape forming a concavity 76 in the midfoot area 67. In the next row, spring element 51 has a flexural axis 59 in the forefoot area 58 consisting of a superior spring element 47 including toe spring and an inferior spring element 50 including a relatively flat shape. Next in the row is a spring element 51 having a flexural axis 59 in the forefoot area 58 consisting of a superior spring element 47 having a relatively flat shape and also an inferior spring element 50 including a relatively flat shape. In the third row, spring element 51 has a flexural axis 59 in the forefoot area 67 consisting of a superior spring element 47 made in continuity with an inferior spring element 50 forming an elliptical shape on the posterior side 34 and next to it is a spring element 51 having a flexural axis 59 in the midfoot area 67 consisting of a superior spring element 47 formed in continuity with an inferior spring element 50 forming an upwardly rounded shape on the posterior side 34. In the next row is a spring element 51 having a flexural axis 59 in the midfoot area 67 consisting of a superior spring element 47 formed in continuity with an inferior spring element 50 forming a downwardly rounded shape on the posterior side 34 and next to it is a spring element 51 having a flexural axis 59 and a concavity 76 in the midfoot area 67 consisting of a superior spring element 47 formed in continuity with an inferior spring element 50 forming an elliptical shape on the posterior side 34. In the next row is a spring element 51 consisting of a superior spring element 47, a posterior spacer 42, and an inferior spring element 50 having a relatively flat shape. As shown, a posterior spacer 42 can provide a substantial elevation in the rearfoot area 68 and next to this is spring element 51 consisting of a superior spring element 47, a posterior spacer 42, and an inferior spring element 50 having an upwardly curved shape at the posterior side 34. As shown, a posterior spacer 42 can provide a substantial elevation in the rearfoot area 68. In the next row is a side view of a spring element 51 consisting of a superior spring element 47, a posterior spacer 42, and an inferior spring element 50 having a complex curved shape at the posterior side 34. As shown, a posterior spacer 42 can provide a substantial elevation in the rearfoot area 68. To the right of that is a spring element 51 consisting of a superior spring element 47, a posterior spacer 42, and an inferior spring element 50 having an arcuate shape. As shown, a posterior spacer 42 can provide a substantial elevation in the rearfoot area 68. In the next row is a spring element 51 consisting of a superior spring element 47, a posterior spacer 42, and an inferior spring element 50 that is orientated downward along the posterior spacer 42, but which is relatively flat near the posterior side 34. As shown, a posterior spacer 42 can provide a substantial elevation in the rearfoot area 68. To the right is spring element 51 consisting of a superior spring element 47 made in continuity with an inferior spring element 50 forming an elliptical shape on the posterior side 34. As shown, the anterior portion of the inferior spring element 50 is affixed to a posterior spacer 42 which can provide substantial elevation in the rearfoot area 68. Alternately, an inferior spring element 50 can be made as a separate part, and can then be affixed to a posterior spacer 42 and/or superior spring element 47 near the anterior end of the inferior spring element 50, and also be affixed to the superior spring element 47 near the posterior end of the inferior spring element 50.

Alternatively, the system can form a multi-polyurethane insole for shoes by curing different elasticity polyurethane materials sequentially above each other in the reformable mold formed above including: a low elasticity polyurethane foam disposed on the top side of the insole; a high elasticity polyurethane foam and a mid elasticity polyurethane foam sequentially laminated at the inside of a generally oval concaved portion formed on the bottom surface of the insole abutting against a wearer's heel portion; and a foot arch base formed integrally with the insole 1 in such a manner as to be protruded from the middle portion of the insole. When the multi-elastic insole is disposed on the bottom surface of the shoe, the wearer's weight is much collected on the oval concaved portion formed on the bottom surface of the insole abutting against the wearer's heel portion on the low elasticity polyurethane foam formed on the top side of the insole, and then, the wearer's body pressure (foot pressure)

is distributed by means of the low elasticity polyurethane foam. Next, the minute movements of the wearer's muscles are caused by means of the high elasticity polyurethane foam formed at the inside of the oval concaved portion 3, and the impacts are finally absorbed by means of the mid elasticity polyurethane foam 4 disposed beneath the high elasticity polyurethane foam at the inside of the oval concaved portion 3, so that the increasing rate of the foot pressure can be reduced. A foot arch base is formed on the top portion of the multi-elastic insole 1 serves to support the load of the wearer's foot generated by the foot pressure, thereby greatly reducing the fatigue of the wearer's foot. When the shoes having the structure of a composite or a multi-elastic insole are worn, the high, mid and low elasticity polyurethane foams are sequentially laminated on the bottom surface of the insole abutting against a wearer's heel portion, so that the impacts generated from the wearer's foot sole while working for long hours at a state of standing up on a hard floor are all absorbed, thereby making the wearer feel comfortable, which reduces the wearer's leg and foot fatigue and prevents the increasing rate of the foot pressure.

In addition to the multi-elastic material and/or composite material discussed above, the sole and the cushion can be made of rubber or can be made of a thermoplastic resin. Preferable materials are those which are easily thermoformable into desired flexible configurations. Materials which can be thermoset after molding and retain the flexible characteristics for the sole components of the present system are included within the scope of preferred thermoformable materials. Thermoset resins solidify or set irreversibly when heated due to crosslinking between the polymer chains Crosslinking can be achieved by using nucleating agents, mold temperatures above the materials forming temperature, radiation, etc. A thermoset resin once set or cured cannot be softened again by heating. Thermoset resins are generally characterized by high thermal stability, high dimensional stability and high rigidity and hardness and include resins such as polyesters and urethanes.

Thermoplastic resins can be either crystalline or amorphous and can be repeatedly softened by heating. Amorphous thermoplastics include acrylonitrile-butadienestyrene (ABS) copolymer, styrene, cellulosics and polycarbonates. Crystalline thermoplastics include nylons, polyethylene, polypropylene and polyurethane. Examples of particularly preferred materials for use in the present system include thermoplastic polyurethanes, nylons, polyesters, polyethylenes, polyamides and the like.

In accordance with another feature of the present system, the cushioning are sealed cushions having different resistances to compression, for example, by being filled with air, or other gas, or liquid at different pressures, e.g., below, at, or above atmospheric pressure, or by controlling the number, size and/or configuration of the indentations. The indentations 126 make that part of the cushion stiffer in compression than another part of the cushion without the indentations. For example, a difference in stiffness for compression between the medial side of the shoe and the lateral side of the shoe can be achieved. Or, a smaller hemispherical radius may be used for the indentations on one side of the shoe. These variations may be used to provide effective pronation or supination control through differences in compression between the medial and lateral sides of the shoe.

Thus, the stiffness or softness of each cushioning member is controllable and selectable at different areas of the heel. This feature enables the shoe to be designed with adjustable cushioning against heel impacts during use of the footwear.

The footwear can be custom produced at the request of a customer, who can specify the nature of the customization for one or more pairs of footwear. Each shoe of a pair of the footwear may have a different design, message or message portion designed into it and rendered using the bed of pins described below to make the custom shoe design messages or shapes, and then the bottom sole can be fabricated using the reformable bed described below. Once the negative is fixed in the reformable bed, suitable materials for the bottom sole can be deposited and cured and can include rubber, plastic, or foam. Further customization can be done by a Computerized Numerical Control (CNC) where component design can be integrated with computer-aided design (CAD) and computer-aided manufacturing (CAM) programs. The device can be programmed to use a number of different tools-drills, saws, and so on. Alternatively a number of different machines can be used with an external controller and human or robotic operators that move the component from machine to machine. Regardless, a series of steps needed to produce a part can produce a part that closely matches the original CAD design in a highly automated fashion. In accordance with aspects of the subject matter disclosed herein through the use of reformable bed and a suitably programmed CNC tools, customized footwear with custom cut sole designs, can cost effectively be created in small quantities and yet scalable for mass-customization.

The sole and the cushion can be made of rubber or can be made of a thermoplastic resin. Preferable materials are those which are easily thermoformable into desired flexible configurations. Materials which can be thermoset after molding and retain the flexible characteristics for the sole components of the present system are included within the scope of preferred thermoformable materials. Thermoset resins solidify or set irreversibly when heated due to crosslinking between the polymer chains. Crosslinking can be achieved by using nucleating agents, mold temperatures above the materials forming temperature, radiation, etc. A thermoset resin once set or cured cannot be softened again by heating. Thermoset resins are generally characterized by high thermal stability, high dimensional stability and high rigidity and hardness and include resins such as polyesters and urethanes.

Thermoplastic resins can be either crystalline or amorphous and can be repeatedly softened by heating. Amorphous thermoplastics include acrylonitrile-butadienestyrene (ABS) copolymer, styrene, cellulosics and polycarbonates. Crystalline thermoplastics include nylons, polyethylene, polypropylene and polyurethane. Examples of particularly preferred materials for use in the present system include thermoplastic polyurethanes, nylons, polyesters, polyethylenes, polyamides and the like.

In accordance with another feature of the present system, the cushioning are sealed cushions having different resistances to compression, for example, by being filled with air, or other gas, or liquid at different pressures, e.g., below, at, or above atmospheric pressure, or by controlling the number, size and/or configuration of the indentations. The indentations 126 make that part of the cushion stiffer in compression than another part of the cushion without the indentations. For example, a difference in stiffness for compression between the medial side of the shoe and the lateral side of the shoe can be achieved. Or, a smaller hemispherical radius may be used for the indentations on one side of the shoe. These variations may be used to provide effective pronation or supination control through differences in compression between the medial and lateral sides of the shoe.

Thus, the stiffness or softness of each cushioning member is controllable and selectable at different areas of the heel. This feature enables the shoe to be designed with adjustable cushioning against heel impacts during use of the footwear.

In the context of shoe manufacturing, a computing device may be used to determine operations of various shoe-manufacturing tools. For example, a computing device may be used to control a part-pickup tool or a conveyor that transfers shoe parts from one location to another. In addition, a computing device may be used to control a part-attachment device that attaches (e.g., welds, adheres, stitches, etc.) one shoe part to another shoe part.

A shoe can be made from the sole or insole. An upper is fixed to the insole by virtue of a hot-melting adhesive which is injected at the time of assembly in the region between the lower part of the assembly insole and a folded upper so that it is possible to assemble the upper part of the shoe with a single operation. Then, according to known methods, the folded upper is glued onto the lower part of the insole and is milled so as to obtain a flat surface on which the sole is finally glued in order to obtain the finished shoe. In the rear part, the insole generally includes, below a supporting base, a metal shank and a reinforcement member which is arranged below the metal shank. The shank is generally fixed to the reinforcement member.

The insole can have a supporting base which includes, on the lower side, a hot-melting adhesive so that said upper can adhere to said insole by heating. Preferably, the insole bears an amount of adhesive between 50 and 300 g/m2 and preferably between 50 and 180 g/m2. Preferably, the adhesive has a melting point between 40 and 180 DEG C., preferably between 45 and 120 DEG C., when measured with the DSC method, with a gradient of 10 DEG C./min. Preferably, the adhesive includes a polymer which is chosen among: polyesters, copolyesters, polyamides, copolyamides, polyolefins, polyurethanes, ethyl vinyl acetates, acrylic resins, polyvinyl acetates, vinyl polymers. More preferably, the adhesive is chosen among: polyesters, copolyesters, polyurethanes, ethyl vinyl acetates, polyamides and copolyamides. The adhesive is formed by a mix of polyurethane and polycaprolactone. Preferably, the adhesive is included in the lower part of the supporting base by depositing adhesive powder. However, in the context of an extensive industrial production, it is feasible to use an adhesive in film form arranged above the lower part of the supporting base. The supporting base can be formed, for example, by an impregnated fabric, by a fabric, by a non-woven fabric, by an impregnated non-woven fabric, by an extruded component, by a coextruded component, by agglomerated fibers or by reclaimed leather. In the case of a coextruded component, the supporting base can be coextruded together with an adhesive film, so as to automatically assemble the two above described parts. The reinforcement can be formed by agglomerated fibers, for example cellulose fibers impregnated with a latex. The supporting base can be provided with microperforations in order to allow the transpiration of moisture. Thus, it is not necessary to apply any adhesive during the assembly of the upper, considerably simplifying this assembly step, reducing the costs and the maintenance burdens. In particular, the complete absence of any device for transferring a liquid adhesive at high temperature clearly drastically simplifies the entire assembly operation. All the downtimes that were dedicated to cleaning the plant, the nozzles et cetera are furthermore clearly eliminated entirely.

It has furthermore been noted that despite using a highly automated method it is possible to obtain shoes with a flexibility that could be achieved only with old manual assembly methods but was absolutely not within the capabilities of currently active modern plants. In particular, it is possible to obtain much more flexible shoes, with obvious advantages.

Surprisingly, it is possible to use the same machines that were used for known methods without having to perform particular modifications. This is a great advantage from the industrial point of view, since the important advantages stated above can be provided immediately without having to sustain high investment costs to modify the machines required to assemble the shoes.

Shoe Recommendation

The foot dimensions can be used to match/best-fit the user to a particular shoe or sole's inside dimensions. In one embodiment, the process can then selects footwear or a shoe with interior best matching the deformable/morphable foot template key sections and girths of the footwear: (1A) Toe Section (2A) Metatarsals Section (3A) Midfoot Section (4A) Heel Section (5A) Profile of the foot (6A) plantar contour. The best fit shoe is shipped to the user. In one embodiment Data Collection Create 3D model of user's feet Identify shoe manufacturers that best fit the user's fit Set the best fit shoe's inside dimension with the 3D model of feet plus a predetermined gap At point of purchase:

Run big data analysis correlating different manufacturer's sizes and create a correspondence between shoes from one manufacturer to other manufacturers Recommend best fit shoe models from the big data analysis Another embodiment includes the following:

capturing 3D model of user's feet;

identify the subject's current best fitting shoe products;

set each best fitting shoe product's inside dimension with dimensions from the 3D model plus a predetermined gap;

correlating different manufacturer's shoe sizes and creating correspondences among different manufacturer shoe products; and recommending a new shoe for the subject by looking up the correspondences among different manufacturer shoe products.

As part of or to assist with the size recommendation process, during analysis the computing device may also determine whether a user-selected item or shoe runs true to size. The system may make this determination before or after the user selects a product by comparing the stored parameter measurements for the user-selected item to standard information related to standard sizes. If one or more of the measured parameters differs by more than a threshold amount from the value(s) of its or their corresponding reference (standard) parameters, then the system may determine that the model of item does not run true to size. For example, for footwear, the system may compare internal measurements such as length and width for the user-selected item (e.g., a size 12 miming shoe) to standard internal measurements for an industry standard (i.e., a reference model) running shoe. To determine the industry standard for a given parameter (i.e., maximum length or width of the overall shoe interior, or of a portion such as the toe box or heel), the computing device may compute an overall average for the parameter for all models that are stored in the data set in that particular size (e.g., overall averages of all internal measurements of all size 12 shoes). Alternatively, the industry standard size may be stored in the data set as provided by a manufacturer, a group of manufacturers, a supplier or group of suppliers, a retailer or a group or retailers, or other similar groups. The system also may consider tactile measurements such as stretch or deformation and use the size corresponding to maximum, minimum, or some intermediate level of stretch or deformation as the shoe's internal measurement in the comparison. During determination of whether an item runs true to size, the system may also consider data that reflects how an item fits as opposed to, or in addition to, determining whether the item is true to standard size. For example, a high heel shoe may include one or more straps that cross the top or arch of a wearer's foot and attach at various points on the sides of the shoe. When worn, one or more of the straps can cause the shoe to fit differently on the wearer's foot, thereby altering the fit and comfort of the shoe. Thus, the data set for that footwear model may include positive value (e.g., "yes," "true," or "1" for a parameter titled "horizontal straps"). The system may also consider such a feature, including various structural and decorative features integrated onto an item, that results in possible deviation from a user's selected size of that item when determining whether the user-selected item runs true to size. Additionally, the system can prompt the user for secondary sizing information and receive the secondary sizing information from the user via a user interface. Secondary sizing information may be the size that the user is most likely to wear if their primary size does not fit properly, or an indication of whether the user is most likely to pick a larger or smaller size if their primary size does not fit properly. The computing device may use the secondary sizing information to provide a more accurate size recommendation for the user.

The system may include providing a sizing recommendation for wearable items such as footwear based upon personalized sizing information received from a user. The process accesses the wearable item data set can include various measurements and parameters related to each of the wearable items. The computing device may receive sizing information related to a specific user. For example, the sizing information may include a primary footwear size and a secondary footwear size as has been previously discussed. Based upon the received sizing information, the computing device may determine a personal reference size specific to that user. For example, the user may be prompted to input their primary footwear size, as well as their secondary footwear sizing information. The user may input that their primary footwear size is a 12, and that their secondary footwear sizing information is that they typically wear a size smaller than a 12 when not wearing their primary size. Based upon this information, the computing device may calculate the personal reference size to be an adjusted size that is smaller than size 12. The adjusted size may be a reference fraction between the user's primary size and secondary size, such as halfway between or ⅕ of a size between. For example, for the particular user discussed above, the personal reference size may be similar to a size 11.8, or slightly smaller than the user's primary size. Conversely, if the user indicated that they typically wear larger than a 12 for their secondary sizing information, the computing device may determine 406 that the user's personal reference size is similar to a size 12, or slightly larger than their primary size. The personal reference size need not be determined by measuring the user's actual foot (or other body part), but rather may be based on internal dimensions of hypothetical (modeled) or actual reference footwear items based on data previously provided by the user, or the user's previous purchases. The computing device can determine the personal reference size by establishing a set of internal wearable item measurements for a reference footwear model and establishing the reference size to be an extrapolated (or interpolated) size that corresponds to the reference model. To continue the above example, the computing device may determine that a user has a personal reference size of about 11.8. The computing device may establish a graph or other similar representation of all footwear that have sizing information stored in the data set, plotting each size against each internal measurement for each individual piece of footwear. The computing device may then fit a best fit line into the data, providing a reference for each measurement as it compares to each footwear size. The computing device can then locate the user's personal reference size, e.g., 11.8, on the graph for each measurement to determine a set of personalized internal measurements for that user. Based upon the user's personal reference, the computing device may identify a recommended size for a user-selected item, and it may provide the recommended size to the user based on how close the user's reference size runs to an actual size, with an adjustment of the model does not run true to size. To continue the above example, if the computing device determines that a user's personal reference are similar to a size 11.8 and the shoe runs true to size, the computing device may identify a size 12 for the shoe since that shoe size the available size that is closest to the user's reference size. Alternatively, for a shoe that runs larger than true to size, the computing device may identify 408 the first available size that is smaller than the user's reference size. In this case, the identified size would be 11.5. Optionally, the system may also consider stretch or deformation, and add or subtract an expected stretch or deformation amount from the user-selected item measurements when selecting the size of that time that is appropriate for the user.

3D Model of Body and Clothing Recommendation

FIG. 2 shows another exemplary process for creating a 3D model of the body. The process can place the body adjacent an object with known dimensions (40). The body can be the upper body of a person or the entire body of the person. The process then takes multiple images or videos of the body and a reference object (42), as done above. Next, photogrammetric techniques are performed to create a 3D model of the body (44) with dimensions based on the reference object. The process optionally selects a standard body template and Morph/Warps the standard body template to match 3D body model (46). Next, the process selects the best fitting wearable item or apparel (48). The present systems include determining and providing sizing information to a user for a specific apparel item in response to a user selection of the apparel item from a retailer, for example, an online retailer.

As used herein, "wearable item" or "apparel" refers to any item or collection of items that are designed, sized and/or configured to be worn by a person. Examples of wearable items or apparel include footwear, outerwear (including, but not limited to coats, jackets, ponchos, capes, robes, cloaks, gloves, and other related outerwear), clothing (including, but not limited to, socks, pants, shorts, skirts, dresses, shirts, gowns, sweaters, hosiery, suits, underwear, lingerie, saris, wraps, swimsuits, neckwear, belts, and other related clothing), headgear (including, but not limited to, hats, helmets, glasses, sunglasses, goggles, earmuffs, scarves, and other related headgear), sporting accessories (including, but not limited to, pads, shin-guards, mouthpieces, protective sleeves, sports-specific gloves, and other related sporting accessories) and other related wearable items. "Apparel model" or "wearable item model" refers to a specific type or version of apparel offered by a manufacturer, typically having a name, model and item number or code. For example, a footwear model refers to a specific model of footwear offered by a manufacturer. "Apparel representation" refers to a computer-readable representation of an apparel model stored in a computer readable medium. An apparel representation may be a two dimensional or a three dimensional representation. For example, a footwear representation may be a 3D representation of a specific footwear model.

Using the deformable body models, the system can handle informal images of the body, for example, when standard digital camera images (e.g. cell phone cameras) are used as input and when only one, or a small number, of images of the person are available. Additionally these images may be acquired outside a controlled environment, making the camera calibration parameters (internal properties and position and orientation in the world) unknown.

To recover body shape from standard sensors in less constrained environments and under clothing, the deformable model such as a parametric 3D model of the human body is employed. The term "body shape" means a pose independent representation that characterizes the fixed skeletal structure (e.g. length of the bones) and the distribution of soft tissue (muscle and fat). The phrase "parametric model" refers any 3D body model where the shape and pose of the body are determined by a few parameters. A graphics model is used that is represented as a triangulated mesh (other types of explicit meshes are possible such as quadrilateral meshes as are implicit surface models such as NURBS). The deformable body model allows a wide range of body shapes and sizes can be expressed by a small number of parameters. The deformable model captures the statistical variability across a human population with a smaller number of parameters (e.g. fewer than 100). To represent a wide variety of human shapes with a low-dimensional model, statistical learning is used to model the variability of body shape across a population (or subpopulation). With a low-dimensional model, only a few parameters need to be estimated to represent body shape. This simplifies the estimation problem and means that accurate measurements can be obtained even with noisy, limited or ambiguous sensor measurements. Also, because a parametric model is being fitted, the model can cope with missing data. While traditional scanners often produce 3D meshes with holes, the deformable models can reconstruct a body shape without holes and without a need to densely measure locations on the body to fit the 3D model. Only a relatively small number of fairly weak measurements are needed to fit the model. The deformable body model also factors changes in body shape due to identity and changes due to pose. This means that changes in the articulated pose of the model do not significantly affect the intrinsic shape of the body. This factoring allows the combining of information about a person's body shape from images or sensor measurements of them in several articulated poses. This concept is used to robustly estimate a consistent body shape from a small number of images or under clothing.

In one embodiment, a method and system are described that enable the recovery of body shape even when a person is wearing clothing. To estimate body shape under clothing, image classifiers are employed to detect regions corresponding to skin, hair or clothing. In skin regions, it is recognized that the actual body is being observed but in other regions it is recognized that the body is obscured. In the obscured regions, the fitting procedure is modified to take into account that clothing or hair makes the body appear larger. The process allows for fitting the body shape to partial depth information (e.g. from a time-of-flight sensor) that is robust to clothing. Unlike a laser range scan, most range sensors provide information about depth on only one side of the object. Information can be gained about other views if the person moves and multiple range images are captured. In this case one must deal with changes in articulated pose between captures. The method estimates a single body model consistent with all views. The disclosed method further uses image intensity or color information to locate putative clothed regions in the range scan and augments the matching function in these regions to be robust to clothing.

In many applications it is useful to employ just one or a small number of images or other sensor measurements in estimating body shape. Furthermore with hand-held digital camera images, information about the camera's location in the world is typically unknown (i.e. the camera is uncalibrated). In such situations, many body shapes may explain the same data. To deal with this, a method is described for constrained optimization of body shape where the recovered model is constrained to have certain known properties such as a specific height, weight, etc. A new method is defined for directly estimating camera calibration along with body shape and pose parameters. When the environment can be controlled however, other approaches to solving for camera calibration are possible. Additionally, a method and apparatus are described that uses "multi-chromatic keying" to enable both camera calibration and segmentation of an object (person) from the background.

Each body model recovered from measurements is mapped in full correspondence with every other body model. This means that a vertex on the right shoulder in one person corresponds to the same vertex on another person's shoulder. This is unlike traditional laser or structured light scans where the mesh topology for every person is different. This formulation allows body shapes to be matched to each other to determine how similar they are; the method makes use of this in several ways. Additionally, it allows several methods to extract standard tailoring measurements, clothing sizes, gender and other information from body scans. Unlike traditional methods for measuring body meshes, the presently disclosed methods use a database of body shapes with known attributes (such as height, waist size, preferred clothing sizes, etc) to learn a mapping from body shape to attributes. The presently disclosed method describes both parametric and non-parametric methods for estimating attributes from body shape.

Finally, a means for body shape matching takes a body produced from some measurements (tailoring measures, images, range sensor data) and returns one or more "scores" indicating how similar it is in shape to another body or database of bodies. This matching means is used to rank body shape similarity to, for example, reorder a display of attributes associated with a database of bodies. Such attributes might be items for sale, information about preferred clothing sizes, images, textual information or advertisements. The display of these attributes presented to a user may be ordered so that the presented items are those corresponding to people with bodies most similar to theirs. The matching and ranking means can be used to make selective recommendations based on similar body shapes. The attributes (e.g. clothing size preference) of people with similar body shapes can be aggregated to recommend attributes to a user in a form of body-shape-sensitive collaborative filtering.

To create a codebook of deformable body models, a database of body scan information is obtained or generated. One suitable database of body scan information is known as the "Civilian American and European Surface Anthropometry Resource" (CAESAR) and is commercially available from SAE International, Warrendale, Pa. The bodies are aligned and then statistical learning methods are applied within the statistical learning system to learn a low-dimensional parametric body model that captures the variability in shape across people and poses. One embodiment employs the SCAPE representation for the parametric model taught by Anguelov et al. (2005).

The system then automatically estimate the gender of a person based on their body scan. Two approaches for the estimation of the gender of a person are described. The first uses a gender-neutral model of body shape that includes men and women. Using a large database of body shapes, the shape coefficients for men and women, when embedded in a low dimensional gender-neutral subspace, become separated in very distinctive clusters. This allows the training of gender classifiers to predict gender for newly scanned individuals based on shape parameters. A second approach fits two gender-specific models to the sensor measurements: one for men and one for women. The model producing the lowest value of the cost function is selected as the most likely gender. In one embodiment, the process produces standard biometric or tailoring measurements (e.g. inseam, waist size, etc.), pre-defined sizes (e.g. shirt size, dress size, etc.) or shape categories (e.g. "athletic", "pear shaped", "sloped shoulders", etc.). The estimation of these attributes exploits a database that contains body shapes and associated attributes and is performed using either a parametric or a non-parametric estimation technique. The gender and/or the biometric or tailoring measurements are used to select a best fitting deformable body model.

Once the best fitting deformable body model is selected using the body codebook models, the system can match various points on the body to the deformable model. The fitting can be performed with people wearing minimal clothing (e.g. underwear or tights) or wearing standard street clothing. In either case, multiple body poses may be combined to improve the shape estimate. This exploits the fact that human body shape (e.g. limb lengths, weight, etc.) is constant even though the pose of the body may change. In the case of a clothed subject, a clothing-insensitive (that is, robust to the presence of clothing) cost function is used as regions corresponding to the body in the frames (images or depth data) are generally larger for people in clothes and makes the shape fitting sensitive to this fact. Combining measurements from multiple poses is particularly useful for clothed people because, in each pose, the clothing fits the body differently, providing different constraints on the underlying shape. Additionally, the optional skin detection component within the calibration and data pre-processing system is used to modify the cost function in non-skin regions. In these regions the body shape does not have to match the image measurements exactly. The clothing-insensitive fitting method provides a way of inferring what people look like under clothing. The method applies to standard camera images and/or range data. The advantage of this is that people need not remove all their clothes to obtain a reasonable body model. Of course, the removal of bulky outer garments such as sweaters will lead to increased accuracy. The output of this process is a fitted body model that is represented by a small number of shape and pose parameters. The fitted model is provided as input to the display and clothing recommender or an apparel fabrication system.

In addition to body shape, the match score may take into account information about products such as clothing. A distance is defined between products. This may be implemented as a lookup table. Let pi be a vector of clothing descriptors such as [Brand, Gender, Clothing_Type, Style, Size]; for example [Gap, Women, Jeans, Relaxed, 8]. The product distance function returns the distance between any two such descriptor vectors. An exact match of brand, clothing type, style and size could be assigned a distance of zero. A match that only includes brand, clothing type and size can be assigned a higher value. Differences in size produce proportionally higher distances.

In a typical scenario, a user wishes to know if a particular garment with properties will fit them. A potentially similar body may have many product vectors associated with it. A product distance between user and test bodies is determined where the closest matching (minimum distance) product vector is found and this distance is returned as the overall match. A general product distance between two bodies can be computed as to find the two most similar product vectors for the two bodies and return their distance.

Additionally, stored in the database with information about products is optional user-supplied ratings. The ratings can be used to augment the product match score; for example by adding a constant to it. A high rating could add zero while a low rating could add a large constant. In this way, both similarity of the item and its rating are combined.

When a body model is created, it may be stored in a secure database with a unique identifier associated with a user. Specifically, the shape coefficients are stored along with the version of the shape basis used (including the date of creation and whether it was created for a sub-population). This allows the body to be reconstructed, matched or measured independent of when it was scanned. If a pair of bodies are created with two different shape bases, it is straightforward (given vertex correspondence) to convert one or both of them into a common basis for comparison or measurement (Section 10). Additionally, ancillary data that the user enters may be stored such as their age, ethnicity, clothing sizes, clothing preferences, etc.

A user may access their body model in one of several standard ways such as by logging onto a website over a computer network using a unique identifier and password. The body model information may also be stored on a physical device such as a phone, key fob, smart card, etc. This portable version allows the user to provide their information to a retailer for example using an appropriate transmission device (e.g. card reader).

The body identifier may be provided by the user to retailers, on-line stores, or made available to friends and relatives with or without privacy protection. In providing access to their body model, the user may provide limited rights using standard digital property rights management methods. For example, they may provide access to a friend or family member who can then provide their information to a clothing retailer, but that person could be prohibited from viewing the body model graphically. As another example, a user could provide access to display the body to video game software to enable the use of the model as a video game avatar, but restrict the further transmission of the model or its derived measurements.

When a person purchases clothing from a retailer (e.g. over the Internet) using their body model, the size and brand information may be (optionally) stored with their body model. This information may be entered manually by the user with a graphical interface or automatically by software that collects the retail purchase information. Optionally the user can provide one or more ratings of the item related to its fit or other properties and these may be stored in the database in association with the clothing entry.

If a person has multiple body scans obtained on different dates, they may all be maintained in the database. The most recent model can be used by default for matching and measurement. When ancillary data is stored, it is associated with the most current scan at that time. Additionally, storing multiple body models enables several applications. For example, body measurements can be extracted and plotted as a function of time. The shape of the body can also be animated as a movie or displayed so as to show the changes in body shape over time. One method provides a graphical color coding of the body model to illustrate changes in body shape (e.g. due to weight loss). Since all model vertices are in correspondence, it is easy to measure the Euclidean distance between vertices of different models. This distance can be assigned a color from a range of colors that signify the type of change (e.g. increase or decrease in size as measured by vertex displacement along its surface normal). Color can alternatively be mapped to other shape attributes (such as curvature) computed from the mesh. The colors are then used to texture map the body model for display on a graphical device.

Collaborative filtering or recommendation uses information about many people to predict information about an individual who may share attributes in common with others. A common example is movie ratings. If many people who liked movie X also liked movie Y, an individual who liked X but has not seen Y may reasonably be expected to like Y.

A new form of collaborative filtering based on 3D body shape is presently disclosed. People with similarly shaped bodies may be expected to be interested in similar products such as clothing or weight loss products. Specifically if many people with similar body shapes to X buy pants of size Y, then an individual X may also be expected to fit size Y. Thus, a body shape model is used as described to match people based on body shape (Section 9 and 10*d*).

Several embodiments of this method of body shape matching are possible:

1. Size recommendation. If a user is shopping for clothing of a particular type, the system identifies N people with similar body shapes (Section 9 and 10*d*) for whom ancillary data related to this (or similar) item is stored in the database (e.g. use the product distance function). A function is used (e.g. a weighed combination based on body shape distance) to predict the best size (Section 10*d*). Body shape as well as similarity in clothing preference may be used in the matching (Section 9).

2. Community ratings. Instead of being presented with a specific size, the user is presented with a list of ratings for the product by people of similar size. The degree of similarity is shown along with optional entries such as the rating, comments, photos, etc. The degree of similarity can be expressed on a point scale or percentage scale by taking the body shape distance measure (Section 9) and normalizing it to a new range (e.g. 1-100 where 100 is an exact match and 1 is the match to a very different body shape).

3. Community blogs. People with similar body shapes may be trying to lose weight or increase their fitness. Shape-based matching is used to find people with similar body shapes. Groups of people with similar shapes (an possibly preferences) define a "community". Users can post information (e.g. in a blog format) about themselves and find postings by other members of the community who of similar shape (or who have undergone as similar change in shape). The key concept is that community is defined based on body shape-related properties.

A seller of a particular garment can associate a body shape, or fit model with a garment where that body is known to fit that garment. For example an individual wants to sell an item of clothing that fits them through an on-line auction. They list the item along with a unique identifier that can be used to match any other body model to theirs. A buyer looking for clothing provides their unique body identifier and the matching component compares the 3D body shapes and ancillary data (including optional ratings of clothing fit) retrieved from a database to determine the match score. Given a plurality of other matches from other fit models a display and ranking software component sorts the items for sale based on the match score (how similar their body is to the seller's). This method for sizing clothing applies to any retail application where a fit model for each clothing size is scanned and the associated body identifier is used to determine whether a new individual will fit that size. A score of the quality of fit (based on the body match score) can be presented or a threshold on the match score can be used to identify one (or a small number of) size(s) (i.e. fit models) that will fit the user's body. This method is analogous to having a friend or personal shopper who is the buyer's size and shape and who tries on clothing for them to see if it fits before recommending it.

More generally, there may be a large database of people who have tried on the same (or similar) garment and each of them can be viewed as a fit model; every person in the database can be a fit model for any product associated with them. The match distance (Section 9) between bodies incorporates shape and other attributes. Attributes can include one or more ratings of the product (for fit, style, value, etc.). The total match score can then include a term for the fit rating indicating whether the garment fits the fit model. Alternatively, the match can be performed on body shape and an aggregate fit rating for the matched bodies computed (Section 10*d*). If the matched bodies have associated reviews for the product stored in the database, these reviews may be optionally displayed to the user such that they are optionally ranked by match score.

In an alternative embodiment, the match similarity is computed only based on product information (brand, style, size) using the ancillary or product distance function (Section 9). A user selects a particular garment and a list of matches (IDs) is generated from the database where each ID corresponds to a person who has purchased and/or rated the product. The body shapes of the matching IDs are compared to the user's body shape by computing the body shape match score. An aggregate of all these scores is computed; for example by computing the mean score. This score is presented to the user (e.g. on a 100-point scale) to indicate how well the garment may fit them.

Automatically Obtaining Fit for Clothing Presented on a Web Page can be done. Using the techniques above for matching a user's body to a database of other bodies that have tried on similar garments, the system includes determining relevant clothing brand, style and size information from a website. When the user clicks a button to obtain their size for a given garment, the size determining process obtains their unique body identifier. The unique identifier for the user's body model may be stored on their computer hard disk or memory, for example, in the form of a "cookie". Alternatively, if no cookie is present, the user is asked to provide authenticating information such as a username and password. Once identified, the body shape of the user is known. The size determining process searches a database for people with similar bodies who have purchased or rated the clothing item as determined by the product determining process. The match score is computed and the N best matches are identified. The number of matches can vary but the default setting in one embodiment is 10. Ratings and comments stored with the N matches may be displayed.

Alternatively the size preferences of these N bodies may be combined to recommend a particular size for the determined product.

Measurements extracted from the body can be used as input to standard pattern generation software for custom clothing or to on-line forms for ordering custom (or semi-custom) clothing.

A shape-sensitive advertising component uses the body model in conjunction with on-line (or cell phone) web browsing and shopping. Based on a person's body shape, advertising (e.g. banner ads in a web browser) may vary. For example, advertisers can select a range of body shapes that fit their product demographics (e.g. heavy men or short women). The body-shape matching component matches advertiser specifications with body shapes and presents shape-targeted advertisements (e.g. for weight loss or plus-sized clothing). For example, an advertiser may specify a gender, height and weight range, a bust size, etc. Advertisers may also specify body shapes based on example 3D body models selected from an electronic presentation of different body shapes or by providing a fit model scan. These exemplar bodies are then used to produce a match score that determines how similar a user is to the exemplar specification.

Body shape information about a user may be stored on the user's computer; for example in the form of a "cookie" that provides a unique identifier to an ad manager software component. The ad manager software component retrieves information about the body from a body model database using the unique identifier. The ad manager software component can keep the identity of the user private and communicate general information about their body shape to a shape-sensitive ad exchange software component. This information may include body shape coefficients, the ID of a similar exemplar body, measurements such as height or weight, demographic information such as age and gender, and shape category information such as athletic or heavy build. It should be understood that standard ad targeting information can also be supplied such as IP address, geographic location and historical click/purchase information. The shape-sensitive ad exchange component matches the shape information about a user to a database of advertiser requests. If there are multiple matching advertisements, one or more of the matching advertisements is selected for display. The mechanism for selection can be randomized or can take into account how much an advertiser is willing to pay. The rate for each advertisement may vary depending on the overall quality of the match score (i.e. how close the user's measurements are to the target shape specified by the advertiser). A standard bartering or auction mechanism may be used for advertisers to compete for presentation to matched users. Statistics of purchases and advertising-related click histories for people of particular body shapes are collected and stored in a database. Matches to the body shapes of other shoppers or website users can also be used to target advertising based on the purchases of other people of similar shape. This is achieved by finding similar body shapes using the body shape matching component and accessing the stored shopping and clicking statistics for people of similar shape. If a person of a particular shape has clicked on an advertisement, an advertiser may pay more for presentation to a similarly shaped person. Any website can be enabled with this shape-sensitive advertising feature using cookies. Users can disable this feature by changing their browser preferences. This shape feature can be combined with other commonly acquired information about shopping and clicking behavior used for the presentation of personalized or targeted advertising.

The estimated body shape model can also be used to try on virtual clothing. There are several computer graphics methods, including commercial products, for simulating clothing draped on 3D bodies and these are not discussed here. The body model can be saved in any one of the common graphics model formats and imported into a standard clothing simulation software system.

Virtual try on is enabled by collecting a database of models of different shapes and sizes wearing a plurality of clothing items. When the user wants to see how they will look in a particular clothing item, the database of stored models is searched for the closest matching body shape for which an image (or graphic representation) of the model in that item exists. This image is then displayed to the user. In this way, each person visiting a retail clothing website may see the same merchandise but on different models (models that look most like them). This provides the equivalent of a personalized clothing catalog for the person's shape. This is a form of "example-based virtual clothing". Rather than rendering clothing using graphics, many images of models are stored and recalled as needed. The key concept is that this recall is based on similarity of body shape.

Virtual Make Up System

Figure 3A:
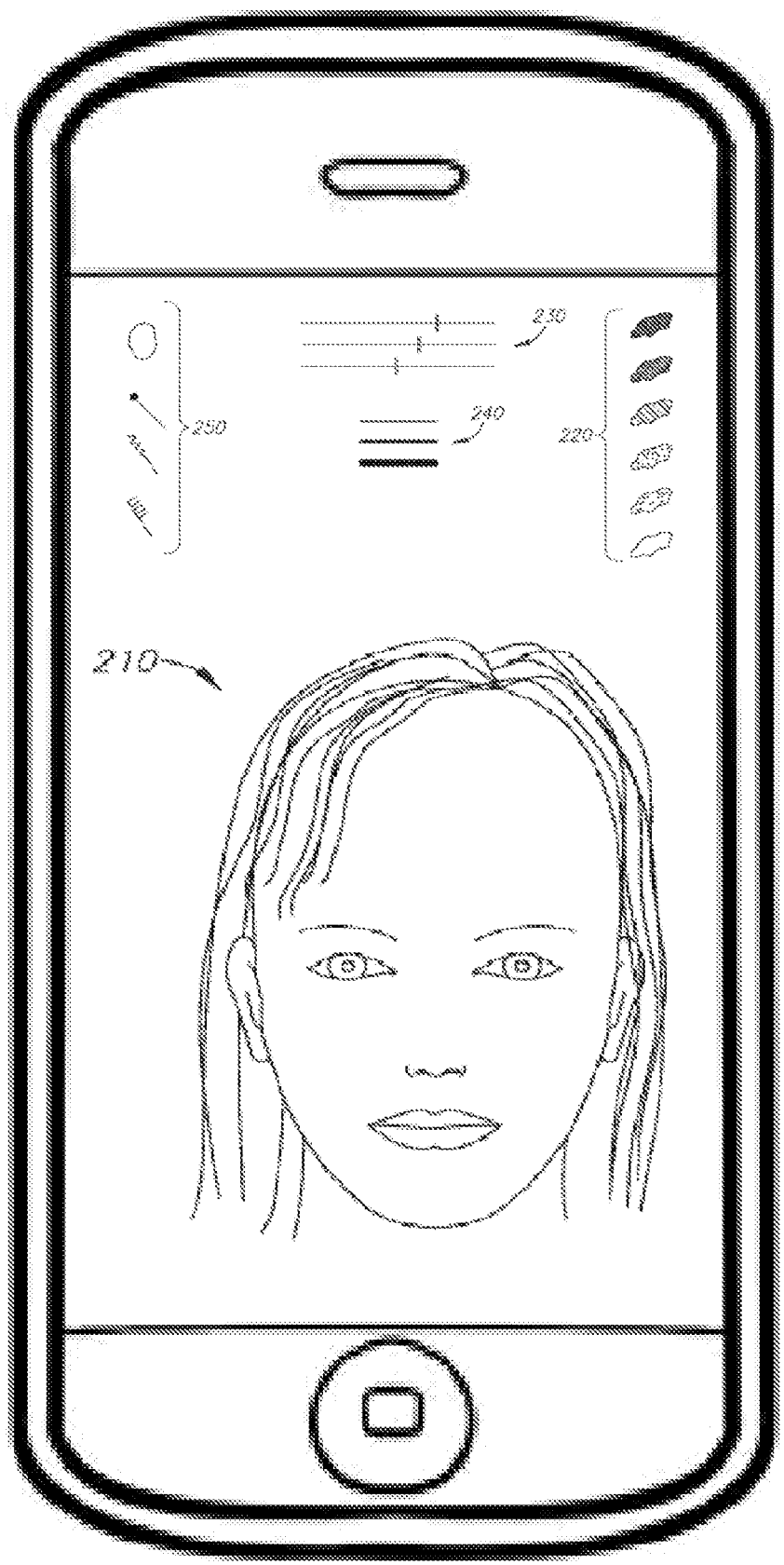

FIG. 3A shows a potential graphical user interface (GUI) with a head image 210 that is a 2D or 3D image of the user, different types of makeup styluses 250 that may be picked by touch and stylus, different widths 240 for the makeup pencil, different lighting conditions as set forth and controlled via rulers 230 and various types and shades of makeup as shown in pallet 220. In operation, the user apply the makeup of his or her choice to image 220 and try various lighting conditions and different shades until he or she is satisfied with the results.

The method of FIG. 3B includes the following:

Scan a bar code or insignia with a makeup product to retrieve color characteristics of the makeup product (220)

Analyze skin pigment from 2D or 3D model of user's face and/or head (222)

Receive a sequence of hand gestures and postures as well as the use of touch and stylus forming a virtual make-up session and apply the color of the makeup product to user skin tone (224)

Apply virtual make-up features to the 2D or 3D model, to yield a 3D make-up model, based on said received hand gestures and postures (226)

Prior to taking pictures of the user, the system reminds the user to that his/her skin is clean and free of any product, such as foundation, powder, or lotion. A sampled portion from an image can be used in detecting skin tone. Images of faces can include skin tone elements (e.g., skin of a face) and non-skin tone elements (e.g., hair, hats, sunglasses, clothing, foliage, etc.). Using a portion of an image for skin tone detection can improve the detection accuracy by maximizing skin tone elements while minimizing non-skin tone elements. The skin tone detection process can extract a portion from the face image. The skin tone detection can evaluate pixels from the extracted portion to determine whether the pixels correspond to skin tone colors. A pixel can be converted to one or more color spaces and analyzed to determine whether the pixel corresponds to a skin tone. The skin tone detection process can maintain information about the overall portion based on the evaluation of the individual pixels. For example, the skin tone detection process can count the number of pixels in the portion and the number of pixels corresponding to a skin tone. Based on the information, the skin tone detection process can determine whether the pixels overall correspond to skin tone colors. For example, the skin tone detection processor can compare the number of skin tone pixels to the total number of pixels to make the determination.

The skin tone is determined by the amount of melanin, or pigment, in the user's skin and does not change from sun exposure or skin conditions. The skin tone will be one of the following: cool, warm, or neutral. The process captures the color of the veins on the inside of the wrist in natural light. If the veins appear blue or purple, the user has a cool skin tone. If the user's veins appear green, the user has a warm skin tone. If the user can't tell if the user's veins are green or blue, the user may have a neutral skin tone. If the user has an olive complexion, the user likely falls into this category.

If the user tans easily and rarely burn, the user has more melanin and the user likely have a warm or neutral skin tone. If the user's skin burns and doesn't tan, the user have less melanin and therefore a cooler skin tone. Some women with very dark, ebony skin may not burn easily but still have a cool skin tone. To Determine Skin Tone Step, a camera can take a picture of a white piece of paper up to the user's face and determine how the user's skin looks in contrast to the white paper. It may appear to have a yellow cast, a blue-red or rosy cast, or it may not appear to be either, but a gray color instead. If the user's skin appears yellowish or sallow beside the white paper, the user has a warm skin tone. If the user's skin appears pink, rosy, or bluish-red, then the user have a cool skin tone. If the user's skin appears gray, the user's skin probably has an olive complexion with a neutral undertone. The green from the user's complexion and the yellowish undertone combines to create this effect. The system can recommend that the user experiment with neutral and warm tones, since the user fall somewhere in between. If the user can't determine any cast of yellow, olive, or pink, the user have a neutral skin tone. Neutral tones can look good in foundations and colors on both ends of the cool/warm spectrum.

In another test, the camera takes a picture with gold and silver foil or jewelry to find the user's skin tone. For example, an image of a sheet of gold foil can be taken in front of the user's face so that it reflects light back on the user's skin. The system determines whether it makes the user's face look grayish or washed out, or if it enhances the user's skin. This is repeated with a sheet of silver foil and if the gold foil looks best, the user has a warm skin tone. And if the reflection from the silver foil makes the user's skin glow, the user has a cool skin tone. If no difference (both silver and gold are flattering), then the user likely have a neutral skin tone. Alternatively, if the user doesn't have gold or silver foil, try laying gold and silver jewelry on the user's wrist, and notice which one is more flattering.

Another embodiment analyzes images of skin behind the user's ear. If the user have acne, rosacea, or another condition that might mask the user's skin tone, the user can take pictures of the skin directly behind the shell of the user's ear, as this area is less likely to be affected. The camera can examine the skin right in the little crease behind the user's ear. If the user's skin is yellowish, then the user's skin tone is warm. If the user's skin is pink or rosy, then the user's skin tone is cool.

Next, the system uses the user's Skin Tone to Choose Colors. The system examines the user's skin in neutral light to find the user's complexion. The user's complexion refers to the surface shade of the user's skin, such as fair, medium, olive, tan, or dark and is not necessarily fixed. So the user's complexion may be lighter in the winter and darker during the summer. By looking at the skin near the user's jawline, the user should be able to determine the user's coloring.

If the user's skin can be described as very white, pale or translucent, the user is fair skinned. The user may have freckles or a little redness to the user's complexion. The user's skin is very sensitive to the sun and burns easily. The user may have cool or warm undertones.

If the user has pale skin that burns in the sun but then deepens into a tan, the user has light skin. The user may have a little red coloring and the user's skin may be mildly sensitive and may have cool or warm undertones.

If the user tan very easily and rarely burn, the user has a medium skin tone. The user likely has warm or golden undertones. If the user's skin is olive or tan year-round (even in the winter), the user's complexion is likely tan. The user almost never gets sunburn and the user's undertone is probably neutral or warm.

If the user has warm, brown skin and black or dark brown hair, the user has a warm complexion. The user's skin darkens very quickly in the sun and the user rarely burn. The user's undertones are almost always warm. Women of Indian or African descent often fall into this category.

If the user has very dark, even ebony skin and black or dark brown hair, the user has a deep complexion. The user may have a warm or cool skin tone and the user's skin hardly ever burns.

The user's skin tone is used to choose the right colors for the user's clothing. Matching the user's skin tone with a flattering color can help the user look the user's best. For example, warm undertones should try neutrals, like beige, cream, orangey-coral, mustard, off-white, yellow, orange, brown, warm red, and yellow-greens. Cool undertones should try blue-red, blue, purple, pink, green, plumb, navy, magenta, and blue-green. Neutral undertones can draw from both groups. Most shades will flatter the user's skin.

Consider the user's skin tone and complexion, the system then recommends the user's new lipstick. If the user has fair or light skin, try light pink or coral, nude, beige, or dusty red. If the user has cool undertones, look for raspberry or mocha or nudes, especially. Warm undertones may want to try red with blue undertones (this will make the user's teeth look very white, too), coral, pale pink or peachy nudes. If the user has tan or medium skin, go for cherry red, rose, mauve, or berry. Deep pinks or corals will look good, too. If the user has warm undertones, focus on tangerine, orange-red, copper, or bronze. If the user has cool undertones, look for wine colored shades or cranberry. If the user have a dark or deep complexion, look for browns, purples, caramel, plumb, or wine colored lipsticks. If the user has warm undertones, try copper, bronze, or even a blue-based red. If the user has cool undertones, look for metallic shades in ruby red or a deep wine shade.

FIGS. 4A-4H illustrate representations of representing eight of the classic facial configurations and, as well, the "perfect" or "ideal" facial configuration of the make-up virtual face/head according to the invention, the said make-up virtual body, face or head facial configuration being capable of formed selectively to any appear as selected ones of the classic facial configurations solely by means of artistic application only of cosmetic compositions to the selected ones of the companion masks; FIG. 4A illustrating the round facial configuration, FIG. 4B illustrating the square facial configuration, FIG. 4C illustrating the pear-shaped facial configuration, FIG. 4D illustrating the heart shaped facial configuration, FIG. 4E illustrating the triangular shaped facial configuration, FIG. 4F illustrating the oblong facial configuration, FIG. 4G illustrating the diamond shaped facial configuration, FIG. 4H illustrating the inverted-triangular facial configuration; FIG. 4I illustrating the "perfect" or "ideal" oval facial configuration of the make-up virtual body, face or head head according to the invention;

FIGS. 5A-5E illustrate the various commonly encountered eye-formations on which the user can virtually apply eye wakeups; FIG. 5A illustrates the typical oriental eye formation with FIG. 5A showing the method of applying eye shadow to such eye formation of FIG. 5A; FIG. 5B illustrates the typical mature eye formation with FIG. 5B' showing the method of applying eye shadow to such eye formation of FIG. 5B; FIG. 5C illustrates the typical deep set eye formation with FIG. 5C' showing the method of applying eye shadow to such eye formation of FIG. 5C; FIG. 5D illustrates the typical close-set eye formation with FIG. 5' showing the method of applying eye shadow to such eye formation of FIG. 5D; FIG. 5E illustrates the basic bulging eye formation with FIG. 5E' showing the application of eye shadow to the eye formation of FIG. 5E.

Directing attention to FIGS. 5A to 5E, five sets of commonly encountered eye formations are automatically detected by the computer and eye makeup is recommended. Upon acceptance of an eye make up pattern and a particular product, the product's color and texture information is retrieved and rendered accurately with the user's skin tone. FIGS. 5A-5E are illustrated along with relatively matching illustrations FIGS. 5A'-5E'; showing one eye, the right eye as viewed, of the eye formations respectively of said eye formations 5A-5E to illustrate the manner taught to the student or trainee how to utilize the three conventional types of eye-shadow in treating the respective eye to accentuate those shapes. There are five different eyeshapes illustrated, namely, the oriental shape shown in FIG. 5A, the natural mature wide set eye formation shown in FIG. 5B, the deep set eye formation shown in FIG. 5C, the closed set eye formation shown in FIG. 5D and the basic bulging eye formation shown in FIG. 5E. The eye formation carried by the companion mask members can be utilized to teach and practice the use of different shading compositions selected and employed to illustrate the application of eye shadow to alter or to reinforce the use of an eye shadow composition to selectively emphasize the training and practice of applying eye shadow cosmetic make-up of the three conventional shades respectively to the masks, to enable the trainee to treat the various different eye formations encountered. These types of eye shadow comprise the range, light eye shadow 76, medium dark eye shadow 78 and very dark eye shadow 80.

FIGS. 5A'-5E' illustrate the method of applying three different shades of eye shadow to the eye formations of FIGS. 15A-15E, only one eye, the right eye as viewed, being shown in said FIGS. 15A'-15E'.

FIG. 5E' presents the oriental eye formation of FIG. 5A for which the light eye shadow 76 is applied at a location across the upper eye lid extending close to the bridge 41 of the nose 42. Then, the very dark eye shadow 78 is applied along a line extending across the eye lid extending along the eye lid in a line following the eye socket. The remainder of the eye lid receives an application of medium dark eye shadow 80 thereacross.

FIG. 5B' presents of the natural mature natural wide-set eye formation for which the light eye shadow 76 is applied to the eye lid along the area adjacent to the eye brow with dark eye shadow 78 being applied to right corner of the illustrated eye lid while the medium density eye shadow 80 is applied to the remainder of the eye lid of the companion mask 14A to result in the treatment applied to the companion mask 12 to give training to the trainee so as to result in the mature appearance.

In FIG. 5C', the deep-set eye formation of FIG. 5C, is shown as the desired result of application of the shades of eye shadow to the eye formation of the companion virtual body, face or head mask to result in the deep-set appearance. Instead of using a substantial coverage of the eye lid, the medium density eye shadow 80 is applied to the upper right corner of the eye lid along the area thereof closely adjacent the right inner portion of the eye lid including a portion near the bridge 41 of the nose 42. Dark eye shadow 78 is applied to the right corner of the eye lid and along the area at the bridge 41 of the nose 42. The remainder of the eye lid is treated with light eye shadow 76.

FIG. 5D' illustrates the close-set eye formation of FIG. 5D on which medium eye shadow 80 is applied at the upper portion of the eye formation 15D', the light shadow 76 and the dark density eye shadow 78 is applied upon the inner half of the eye lid to reach the right corner of said eye lid closely adjacent the bridge 41 of the nose 42. The remaining half of the eye lid receives the light shadow to the left area of the eye lid to result in the close set eye formation.

FIG. 5E illustrates the basic bulging eye formation which receives the application of light eye shadow 76 along the upper area of the eye socket to the upper right hand corner of the right hand portion of the eye lid extending to the right side of the bridge of the nose. The dark eye shadow 78 is applied below the area occupied by the light eye shadow 76 and extends from the left corner of the bridge of the nose below the light eye shadow partially along the left eye socket from the bridge of the nose. The remainder of the eye lid receives coverage of a medium density shadow 80.

Figure 6A:
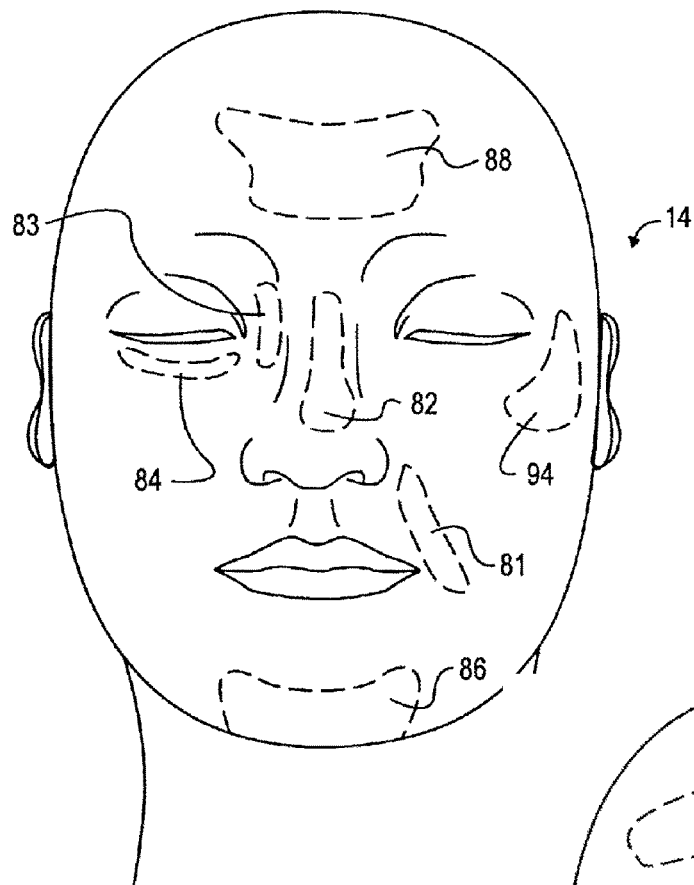
FIG. 6A-6B illustrate computer applications of selected cosmetic compositions such as dark foundation, eye disguise or highlighter applied to the virtual face.

FIG. 6A illustrates a virtual application of cosmetic preparations such as light foundation creme, eye disguise and/or highlighter to the face image or 3D model so as to effect an improvement of the facial appearance, reducing the effect of various encountered areas on the facial configuration which are improved. The face model or image 14 is illustrated having various areas of improvement to which the application of light foundation creme, eye disguise, highlighter, concealer or blush will result in a change in the light reflection angle so as to change the visible impression to the viewer. In this way, an illusion is created reducing the viewer's recognition of the undesired feature. Application of shadow at the cheek areas 81 of the mask as shown in FIG. 6A will cause the viewer to see the visage or facial configuration as thinner than its physical reality. Likewise, a thick or wide nose can be made to appear thinner to the viewer by application of a light reflective foundation creme to the sides of the nose bridge at area 82 of the mask as shown in FIG. 6A. The visual effect of deep-set eyes can be disguised by application of light foundation or eye disguise to the area 83 at the bridge of the nose between the inner right hand corner of the right eye as shown in FIG. 6A to the degree that the reflection of light is changed. The appearance of dark circles under the eyes can be ameliorated by applying concealer instead of highlighter at area 84 of the mask as shown in FIG. 6A. Light foundation can be applied at area 86 of the companion mask 16 as shown in FIG. 6A which application changes the reflection of light thereat to reduce the visible appearance of a receding chin. The appearance of a low forehead can be modified by application of light foundation creme at area 88 of the companion mask 14 as shown in FIG. 6A. Area 94 of the companion mask 14 illustrated in FIG. 6A is receptive of application of light foundation creme to reduce the visual effect of a long face.

Figure 6B:
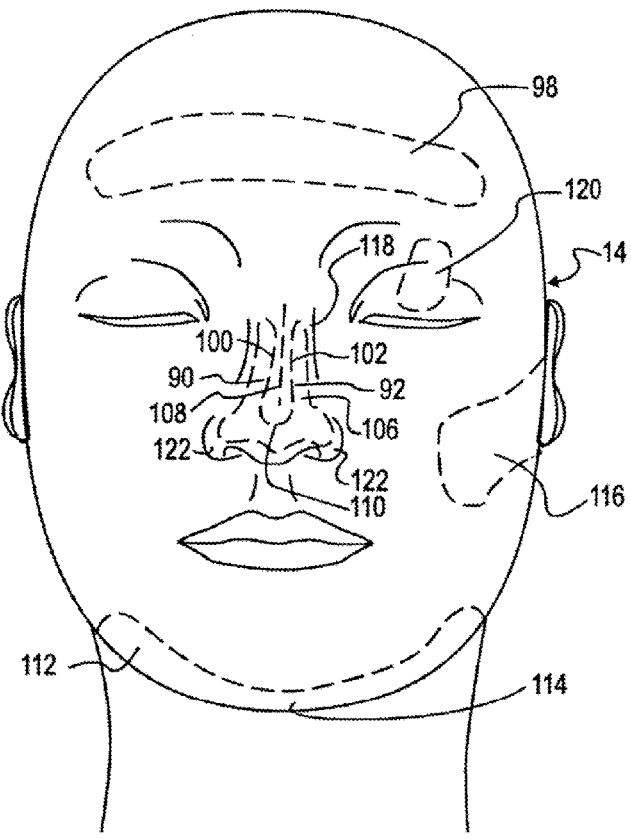

FIG. 6B illustrates the areas of the mounted mask to which dark foundation or eye disguise can be applied to conceal or reduce the appearance of certain perhaps objectionable characteristics of the facial configuration. The appearance of a long nose can be disguised by application of dark foundation or shadow along both sides of the nose at areas 90 and 92 of the facial configuration of the mask 14 as shown in FIG. 6B. The appearance of a protruding forehead can be disguised by applying dark foundation to the area 98 of the mask 14 as shown in FIG. 6B. If the undesired appearance of a large nose is to be reduced, application of dark foundation at area 100 of the companion mask shown in FIG. 6B effects contouring the center of the nose. The trainee can be taught and can practice the techniques to disguise or conceal the appearance of a wide nose by contouring along both sides of the nose at areas 90 and 91 of the companion mask 14 shown in FIG. 6B. A hooked nose can be disguised by contouring the protruding bone by contouring the area 102 of the protruding bone of the companion mask 14 shown in FIG. 6B. A crooked nose can be made to appear straight by contouring the crooked side along area 106 with dark foundation and highlighting the center line 108, stopping at the bulb 110 at the end of the nose of the companion mask 14 as shown in FIG. 6B. The appearance of a double chin can be corrected by contouring the entire length of the chin at area 112 of the companion mask 14 with dark foundation or eye disguise while the appearance of a long chin can be improved by applying dark foundation by contouring the area 114 at the center only of the chin of the companion mask 14 as shown in FIG. 6B. Likewise, a square prominent chin can be reduced in appearance in the same manner as the double chin is minimized. The appearance of large jaws can be reduced by applying can be concealed by application of dark foundation or eye disguise along area 116 at the upper cheek of the companion mask in the vicinity between the right eye and the lower portion of the ear in FIG. 6B. A wide nose requires application of dark foundation creme or eye disguise contouring both sides of the nose at areas 118 as shown in FIG. 6B. The appearance of heavily lidded eyes can be ameliorated by application of dark foundation or eye disguise at area 120 of the companion mask shown in FIG. 6B. Area 122 of the companion mask 14 illustrated in FIG. 6A is receptive of application of light foundation creme to reduce the visual effect of a long face. A long nose requires application of dark foundation at areas 122 as shown in FIG. 6B contouring the base of the nose and the tip thereof as carried by the companion mask 14.

The above discussion is intended to illustrate the operation of the masks 14 of the make-up virtual body, face or head masks of the invention as intended for use by trainees or students of cosmetology in the course of their studies in beauty schools and the like. As mentioned earlier, the trainee or student user of the make-up virtual body, face or head kit has, in a portable carrier, the full complement of make-up virtual body, face or head, masks of selective different color, materials and tools, providing portability enabling the trainee or student to learn and practice both in the school and at home or other location outside the school area. Not only do the trainee or student have access to the required tools anywhere, but also, with the soft-skin make-up virtual body, face or head and plural soft-skin masks of the varied different ethnic colors to select, the soft-skin virtual body, face or head enables the trainee, student or other user of the kit to learn and practice the art of facial massage due to the softness and flexibility of the surface and texture of the material.

Figure 7A:
FIGS. 7A through 7I are representative illustrations of the various types of lip outlines of lip configurations for makeup on the virtual face or model of the user.
Figure 7B:
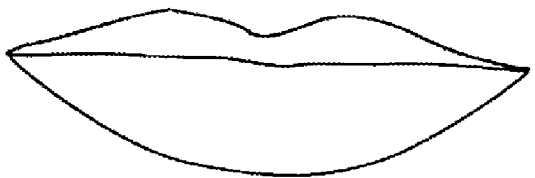
Figure 7C:
Figure 7D:
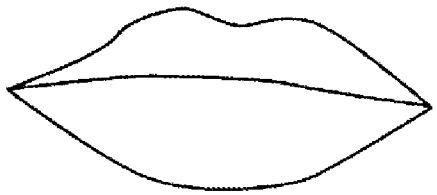
Figure 7E:
Figure 7F:
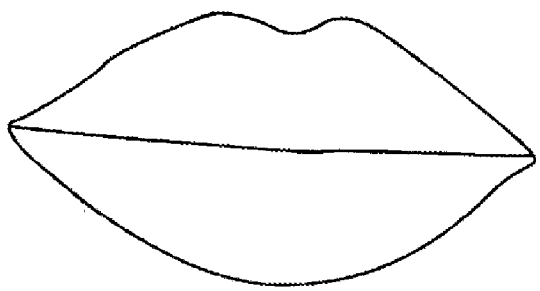
Figure 7G:
Figure 7H:
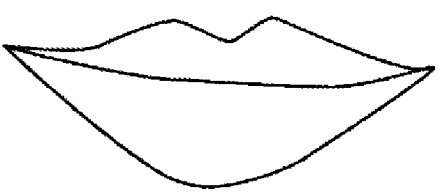
Figure 7I:
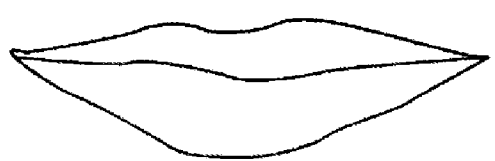

In FIGS. 7A-7I, there are shown plural representations of likely lip formations—than is lip line formations—representative of the lip lines to be applied by the art of permanent make-up, that is by tattoo technique. In the figures set forth, FIG. 7A illustrates a lip formation where both upper and lower lips are thin; FIG. 7B illustrates a lip line formation comprising a thin upper lip compared to a thick lower lip; FIG. 7C illustrates a lip line formation comprising a relatively thin upper lip line is combined with a thicker lower lip line. FIG. 7D illustrates a small line mouth with the lower lip line is thicker than the upper lip line. FIG. 7E illustrates a lip formation having an arrow bow configured upper lip line and the lower lip is thicker than the upper lip. However, the lip line of the pair shown in this FIGURE droops at its ends, particularly the lower lip line droops. FIG. 7F provides an outline of an eye formation wherein the lip outlines comprise a large full centered pair of lips with tight corners where as FIG. 7G illustrates lip outlines which illustrates a small full centered pair of upper and lower lip outlines. FIG. 7H illustrates lip outlines representing a small, uneven pair of upper and lower lips, the upper lip outline being arrow bowed and the lower lip outline being substantially thicker than the upper lip outline. FIG. 7I illustrates a lip line formation where the upper lip is thin and uneven as well as arrow bowed, the lower lip outline also is thicker than the lower lip outline but is not as sharply bowed as the lower lip outline shown in FIG. 7H.

Clothing Fitting System

A user can be a consumer of fashion items. Further, a user may include an expert such as a fashion professional, where this fashion professional includes a fashion designer, a personal shopper, a personal stylist, a journalist who reports on fashion, or some other suitable person. Matching is based, in part, upon an attribute of a fashion item. Attributes include color, fabric, cut, designer, size, time of creation, and other suitable attributes used in denoting a fashion. In one example embodiment, matching includes receiving input in the form of a particular fashion item, and based upon this fashion item suggesting an additional fashion item based upon matching attributes. Matching is facilitated through the use of a learning machine. In one example embodiment, the learning machine can determine the user's favorite actress or model and build a related association. Thus, the fashion style from trendy stars, models, and musicians followed by the user in social media (facebook, twitter) can be analyzed and similar items can be added to the virtual digital closet of the user. Similar clothing items worn by the actress or model can be retrieved and the clothing data can be superimposed on the 3D model of the user to show the user the expected appearance. In addition, experts such as magazine editors/writers can provide outfit ideas and the user can apply the outfit ideas to his/her wardrobe and hairstyling such as suggestions at http://www.glamour.com/fashion/outfit-ideas, among others. The user can adjust color or size or any other attributes of the clothing, and place an order. The order is sent to the fashion maker, who customizes the item accordingly and ships the product to the user.

Figure 8B:
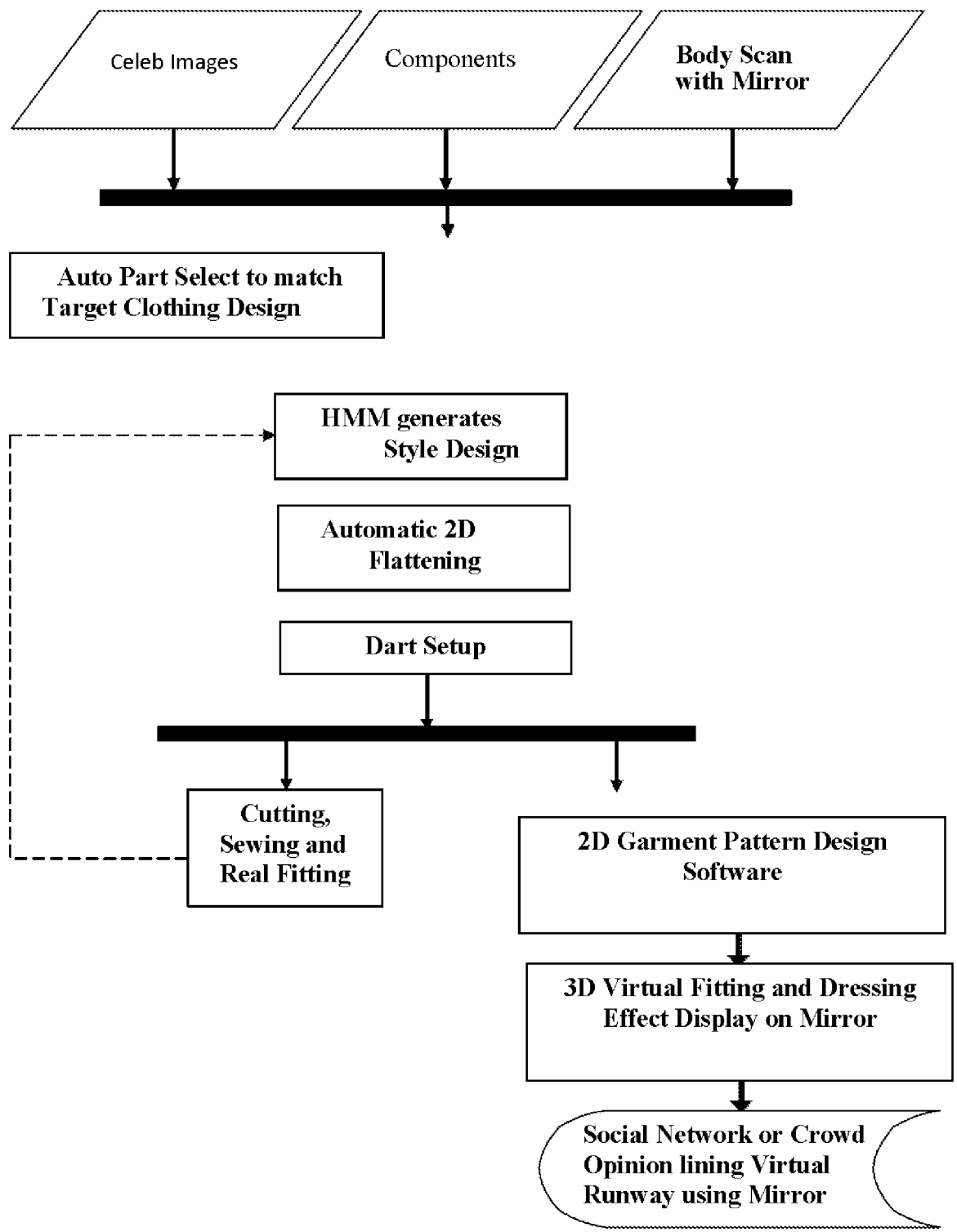
FIG. 8B shows an exemplary process for producing custom fashion clothing based on images or videos of a model or a celebrity that the user likes.

One exemplary process is as follows:
- Identify user's current fashion style. The fashion item can be hair styles, clothing, shoes, bras, dental wear (braces/aligners)
- Determine matching style sets based on one or matching attributes, current fashion style, fashion experts, or celebrity styles
- Present matching style sets and get user selection
- Identify vendor of the user selected style Render a 3D augmented reality imposed over the user 3D model for preview Accept user customization requests and re-render the 3D augmented reality view Send data to the vendor to ship fashion product to the user FIG. 8A shows an exemplary process to provide mass-customized clothing Capture 3D model of clothed body (310)

Digitally remove current dress (312)

Select new fashion styles from new trends (314)

Morph or project clothing onto the 3D model of body (316)

Allow user to iterative change fashion color, length until satisfied with new clothing (318)

Allow user to select from a library of jewelry and shoes to provide realistic simulation (320)

Order desired clothing with custom measurements (322)

In one embodiment, trendy clothing identified based on news or Internet buzz can be located. In this embodiment, the system performs a search of an inventory of fashion items based on the identified fashion preference of the user and then performs a similarity search of the fashion inventory and generates similarity search results (e.g., fashion items that are similar to an item previously worn by the user).

In some example embodiments, the similarity search is based on an image search of the style or the identification of similar clothing. In some instances, the similarity search is also based on one or more measurements of the user's body. For example, to perform a similarity search, the search module compares one or more visual features extracted from the fashion image and one or more visual features identified in an image depicting a fashion item included in the fashion inventory being searched. In some example embodiments, the similarity search is based on an attribute-value pair that characterizes a fashion item previously worn by a celebrity, model, star, user's friend, user's social network or even by the user. In some instances, the similarity search is also based on one or more measurements of the user's body. The performing of the similarity search may include selecting an attribute-value pair to be used as a query attribute-value pair and identifying one or more items in the fashion inventory that are characterized by the attribute-value pair. In some instances, the coordination search is also based on one or more measurements of the user's body. The performing of the coordination search may include identifying, based on a coordination rule, one or more items in the fashion inventory that can be worn together with the fashion item that corresponds to the query image. Similarly, the search module may perform a similarity search based on the first image and then may generate one or more similarity search results. The search module may perform a coordination search based on the second image and further generate one or more coordination search results.

As still yet another embodiment, a feature to perform similarity searching is a user's geographical location used as a criterion to match the user to other users as style may vary from one location to another location. To illustrate this type of feature by way of example only is the case where a user A is a business executive woman living in Country A1. She is travelling on a business trip to country B1. Country A1 could be a conservative country, where ethnic attire is normally worn even in business meetings. Country B1 could be a fashion conscious country. User A may want to wear fashionable clothing, that would look smart on her and be appropriate for business meetings in B1." In yet another example of using this type of feature of engine 110 is illustrated as follows, a user is a graduating 22 year old female, 5'3", 145 lbs, having a hourglass body shape, starting a new job as a project manager in New York. She does not know what kind of attire is appropriate and what style of clothing would look good on her. She creates an account on the system of the present invention, creates her profile, enter her attributes, instantly gets matched to other users of similar attributes and gets recommendation on what style of attire would look good on her. In another preferred embodiment, the system may her to purchase the item in her size.

Based on the above fashion recommendation, the system can fabricate mass-customized clothing for the user that is trendy. The process has a training phase and a run-time phase as follows:

Training

Collect library of fashion designs (Pinterest, Google image, facebook images)

Normalize the fashion designs to standard size

Break up the designs into sections and extract features of sections

Clusterize the features into a codebook of clothing design sections/elements

Train library and create probabilistic model (HMM) to represent a fashion design as a collection of sections Run-Time Generate 3D model of user Receive images of target fashion worn by celebrity or model for the user Normalize target fashion images to a standard size Extract features from the target fashion images Apply probabilistic model to features and create a 3D model of the target fashion model Do virtual fit to the user 3D model and optimize the 3D clothing model for crotch fitting and movement stress Flatten the 3D clothing model into 2D pattern Present to laser cutter to cut pattern Move cut pattern to computerized sewing system Perform QA as needed and ship mass-customized clothing to user In one embodiment, the system receives images of trendy clothing or clothing style from a celebrity that the user wishes to match. The images can be extracted from various news outlet or celebrity sites, for example from google images with search "celebrity fashion" or "tom cruise fashion", for example. For both training and run-time, the system generates features associated with portions of the fashion clothing. In one embodiment, a L-C-S-H process can be used, for low-level-characteristics-selection mask-high level. Low-level refers to the features that are calculated from the images of each article (e.g., 2D shape, 2D color, 2D texture, 2D edges, and 3D shape). Characteristics refer to the attributes that are found on generic articles of clothing (e.g., pockets, collars, hems). Selection mask refers to a vector that describes what characteristics are most useful for each category (e.g., collars and buttons are most useful for classifying shirts), used as a filter. High level refers to the categories to be classify (e.g., shirts, socks, dresses). In one embodiment, the unique characteristics to differentiate categories of clothing can be: Collar, Top brackets, Dark colored, Denim, Ankle hem, Front pockets, Graphic pictures, Colored, Plaid, Thigh hem, Back pockets, Graphic texts, White colored, Patterns, Inseam, Side pockets, Belt loops, V-neck, Round neck, Elastic band, Top buttons, Striped, Bicep hem, Front zipper, Shoulder hem, Wrist hem, or Shin hem, among others.

The L component of the approach uses the low-level features to estimate if the article does or does not have a particular characteristic. The low-level features that were used in this approach consist of color histogram (CH), histogram of line lengths (HLL), table point feature histogram (TPFH), boundary, scale-invariant feature transform (SIFT), and fast point feature histogram (FPFH). To combine the low-level features of all five instances into a single value or histogram, each value is determined by averaging each individual value along with its neighbors, in the case of the histogram.

For the part of the algorithm that converts from low-level to characteristics, low-level features are compared to the various characteristics. Since the characteristics were binary values, libSVM is used to solve the two-class problem. Each low-level feature determines if the characteristic is in class 1 or 2. Class 1 contains positive instances and class 2 contains negative instances.

For an article of clothing, a high definition RGB image and a raw depth map and background subtraction is done on the RGB image to yield an image of only the object. The background subtraction is performed using graph-based segmentation. Once the object is isolated within the image, multiple features are calculated from the RGB image and the 3D point cloud. These features capture 2D shape, 2D color, 2D texture, 2D edges, and 3D shape for both global and local regions of the object. One implementation uses Felzenswalb and Huttenlocher's graph-based segmentation algorithm which uses a variation of Kruskal's minimum spanning tree algorithm to iteratively cluster pixels in decreasing order of their similarity in appearance. An adaptive estimate of the internal similarity of the clusters is used to determine whether to continue clustering.

A color histogram CH is a representation of the distribution of the colors in a region of an image, derived by counting the number of pixels with a given set of color values. CH are chosen in this work because they are invariant to translation and rotation about the viewing axis, and for most objects they remain stable despite changes in viewing direction, scale, and 3D rotation. CH is used to distinguish, for example, between lights and darks, as well as denim.

A Table Point Feature Histogram (TPFH) feature consists of a 263-dimension array of float values that result from three 45-value subdivisions, that are calculated from extended fast point feature histograms (eFPFH), and 128-value subdivision for table angle information. This feature is a variant on the viewpoint feature histogram. The eFPFH values are calculated by taking the difference of the estimated normals of each point and the estimated normal of the objects centerpoint. The estimated normals of each point and the centerpoint are calculated by projecting them on the XY, YZ and XZ plane.

A boundary feature captures 2D shape information by storing the Euclidean distances from the centroid of each article to the boundary. First, the centroid of each binary image is calculated containing the object (after background subtraction). Then, starting at the angle of the major axis found by principle components analysis, 16 angles that range from 0 to 360 (i.e., 0 to 337.5) are calculated around the object. For each angle, the process measures the distance from the centroid to the furthest boundary pixel Other feature includes histogram of line lengths (HLL) to help distinguish between stripes, patterns, plaid, and so forth. For this, we use the object image as before (after background subtraction) and compute the Canny edges, then erode with a structuring element of ones to remove effects of the object boundary.

Next, local features can be computed. The SIFT, scale invariant feature transform, descriptor is used to gather useful 2D local texture information. The SIFT descriptor locates points on the article (after background subtraction) that provide local extremum when convolved with a Gaussian function. These points are then used to calculate a histogram of gradients (HoG) from the neighboring pixels. The descriptor consists of a 128-value feature vector that is scale and rotation invariant.

A FPFH, fast point feature histogram descriptor can be used to gather local 3D shape information. The FPFH descriptor utilizes the 3D point cloud and background subtraction for each article and segments the article from the background of the point cloud. For each 3D point, a simple point feature histogram (SPFH) is calculated by taking the difference of the normals between the current point and its neighboring points with a radius. Once all of the SPFHs are computed, the FPFH descriptor of each point is found by adding the SPFH of that point along with a weighted sum of the neighbors. Other features and descriptors can be used.

Once the features are computed, the global features are concatenated to create a histogram of values. For local features, SIFT and FPFH are calculated separately through bag-of-words to get two element histograms of codewords. Being concatenated, this yields predetermined values for the local features. Then being concatenated with global features yields additional values, which are then fed to the multiple one-versus-all SVMs.

With the codebook, one embodiment can train a probabilistic learning system such as Hidden Markov Model (HMM) to represent a fashion design as a constrained combination of various esthetic components or sections. HMM is a statistical Markov model in which the system being modeled is assumed to be a Markov process with unobserved (hidden) states. A HMM can be presented as the simplest dynamic Bayesian network. In simpler Markov models (like a Markov chain), the state is directly visible to the observer, and therefore the state transition probabilities are the only parameters. In a hidden Markov model, the state is not directly visible, but the output, dependent on the state, is visible. Each state has a probability distribution over the possible output tokens. Therefore the sequence of tokens generated by an HMM gives some information about the sequence of states. The adjective 'hidden' refers to the state sequence through which the model passes, not to the parameters of the model; the model is still referred to as a 'hidden' Markov model even if these parameters are known exactly. A hidden Markov model can be considered a generalization of a mixture model where the hidden variables (or latent variables), which control the mixture component to be selected for each observation, are related through a Markov process rather than independent of each other. Recently, hidden Markov models have been generalized to pairwise Markov models and triplet Markov models which allow consideration of more complex data structures and the modelling of nonstationary data. Other machine learning/classifiers can be used, as detailed below.

Once the system is set up, it can recognize and recreate clothing given an input image. For example, if a celebrity wears a fashionable clothing to attend a highly publicized event, images of the celebrity are publicized and the user may want to replicate the look. In this case, the system retrieves a 3D model of the user and receives images of target fashion worn by celebrity or model liked by the user. The system normalizes the target fashion images to a standard size and extracts features from the target fashion images as detailed above. The system applies the probabilistic model to features and creates a 3D model of the target fashion model using the HMM recognizer using the components/sections model. The system can then apply a virtual fit to the user 3D model and optimize the 3D clothing model for crotch fitting and movement stress.

In one embodiment, since the optimization problem is combinatorial and the number of combination items can vary (e.g., a pockets can be added or removed), it is difficult to define a closed-form solution. In fact, as in the real world, it is desirable to obtain multiple optimal solutions (outfits) from the various components instead of a single global optimum. The process generates candidate solutions by sampling a density function defined over the space of possible outfits. The density function is defined using idealized analytical formulations. Sampling is preferably performed using a Markov Chain Monte Carlo sampler. During the optimization dimensionality may change; i.e., the number of clothing components/sections may be altered during the optimization process, and a Reversible Jump MCMC (RJMCMC) framework supplements parameter-changing diffusion moves of Metropolis-Hastings (MH) with an additional set of dimension-altering jump moves, which allow the chain to move between subspaces of different dimension. To efficiently explore the solution space, a simulated annealing technique is applied in the optimization process with a Boltzmann-like objective function. A dimension matching strategy is adopted to allow reversible jumps across subspaces of different dimension or within the same subspace. The RJMCMC can be used to define the jump moves as adding/removing a clothing item to/from the outfit, which induce a dimension change, and diffusion moves as swapping items or modifying an item's colour, which involve no dimension change.

Various fitness criteria can be applied to evaluate how well the new design fits the user, such as comparing lengths and areas, analysis of space between clothing and the body, among others.

The final clothing model is flattened into 2D pattern. In one embodiment, each mesh element is deformed during the flattening from 3D to 2D plane. A pattern projection can be used that takes into consideration elastic and shear properties of the fabric.

One embodiment uses Design Concept Tex Tech (DCTT) software. The flattening operation involves two steps: first, the selection of the region part to be flattened, and second, the selection of flattening options appears in the "Flattening parameters" dialog box. The flattening tool provided by DCTT considers the geometric constraint of the shape, but no material properties. The process is comparable to the flattening of a network of springs whose stability is obtained through an even distribution of its internal energy. It is an iterative process which proceeds layer by layer beginning from the flattening start point. To control the flattening process, DCTT offers both automatic and numerical options, as can be seen in FIG. 3-6. The automatic control allows the flattening algorithm to run until balance is reached. This option is always selected for pattern flattening throughout this research work. To prepare the flattened pattern pieces for meaningful use in clothing manufacturing, an appropriate seam allowance is added around them. This is done in a "2D product" document using the "design parts" tool with the "create seamline part" option, which is available under the "parts" menu. Rendering of the virtual clothing items developed on the 3D templates is performed by keeping both the "3D Design" document (containing the 3D template and virtual clothing design) and the "2D pattern" document (containing the flattened pattern pieces open). On the active "2D Pattern" document, the "create rendering" tool with a "create virtual marker" option available under the "Pattern" menu is used to apply different graphical images of a particular pattern piece. After doing that, when the "realistic rendering" option in the "rendering" tab is activated, the graphic image applied on the pattern pieces is visualized in 3D.

In another embodiment, from the 3D model of the user, 2D non-contact anthropometric and automatic pattern generation system of men's shirts and pants can be done. The system needs the users to provide front and side photos of the target celebrity or model, and carry interaction design of shirts or pants' styles. Then the patterns can be automatically generated based on the user's physical measurement, the celeb photos and the style design. The two-dimensional anthropometric system is integrated with automatic pattern generation system. In one example, for men's trousers, an automatic pattern generation can apply predetermined rules on the 3D model of the user such as those by Hong Xu in Pattern Automatic Generation for Men's Trousers, ISSN: 2005-4297 IJCA 2014 SERSC.

The 2D pattern can be sent to a cutter such as a CNC or a laser cutter to cut patterns from a fabric that is selected by the user, and the system can move the fabric with the cut pattern on a conveyor to a computerized sewing system, where a robot can pick up the pattern and the sewing system can assemble the pieces into mass customized clothing. The machine fabrication can extend into computer controlled weaving, dying to create a highly mass-customized fashion wear for users, as shown in FIG. 8C.

In some embodiments, the user's purchase history, retained as part of their account information, may be used as training data for a Bayesian network component associated with the outfit suggestion component. For example, if the user has previously purchased high heel shoes and a jacket in the same purchase, the Bayesian network component may recognize that sports shoes and vests should both belong to the outfit.

The present 3D clothing design systems offer a number of benefits over 2D clothing design systems in use. Virtual prototyping using computer-based 3D clothing product-development techniques results in fewer physical prototypes and a shorter product-development phase. For decision-making on product selection and prior to the commencement of production, it is usual for at least two up to ten physical prototypes to be made when using existing traditional product-development systems and this incurs a high cost involvement and time consumption. Virtual prototyping and virtual try-on processes can significantly reduce the product-development time and cost. Virtual review and evaluation of fit with realistically simulated fabric behaviour can enable faster detection of errors and earlier corrections to design elements, material selection and assembly. At the same time, the virtual prototypes can be used as a marketing aid for online product presentation and internet-based retailing. The application of flattening technology provides the opportunity to combine clothing design and pattern creation in to a single step. Automatic flat pattern extraction from 3D designs offers a considerable reduction of the time and manpower involvement in the pattern cutting process. The instant 3D CAD system will form the nerve centre of at the centre of a textile information network.

Crowd Based Feedback for Manufacturers

The process includes collecting, aggregating and analyzing the feedback information, according to an embodiment. For example, the recommendation system may receive an inquiry for a user-selected wearable item and generate a recommended size for the wearable item for the user. More specifically, the recommendation system may access a database including a plurality of representative model of wearable items. The recommendation system may also access a user's profile to determine a size of a wearable item the user has indicated they have previously owned or worn. Based upon a comparison of the profile data and the representative models of the user-selected item, the recommendation system can generate and present the size recommendation to the user. The user can then opt to purchase the recommended item, and the recommendation system (or a purchasing computer or system associated with the recommendation system) can complete the transaction and update the user's profile to indicate that the user has purchased the item. After the user has purchased the item, the recommendation system may generate and/or send a message to the user to prompt the user to provide feedback regarding the recommended size for the purchase item. For example, an email or other similar electronic message may be send to the user after a period of time has elapsed from the purchase date. Alternatively or additionally, the user may be prompted to provide feedback information the next time that they access the recommendation system. The feedback may be an assessment of the fit and/or performance of the item as described above. Analysis of the feedback information may include analyzing the individual user's feedback for any anomalies or information that would indicate an error by either the user or the recommendation system. Similarly, the feedback information may be analyzed to determine that the user received the correct product. For example, if the user indicates that the overall length of the item they received is off by more than an acceptable amount, it may be determined that the user has received an improperly marked or manufactured item.

Additionally, the user feedback can be combined with additional user feedback related to the same item to provide a group analysis of both the recommendation system's output for that item (e.g., how accurate is the recommended size being output for that item) as well as to determine any trends related to the manufacturer of that item (e.g., nearly 30% of all users report that the item runs much smaller than the size would indicate). Such a group analysis can provide a larger scale view of both the recommendation system's recommendation as well as the manufacturing characteristics of the item. Based upon the analysis, the recommendation system can use the feedback information to improve the recommendation system. For example, if users are consistently indicating that a sizing recommendation for a particular shoe is wrong, and that the actual size of the shoe is smaller than recommended, the recommendation system may recognize that a high number of users are leaving negative feedback, and provide a report or an indication to an administrator or other similar personnel that the stored measurements for that particular item may need to be reviewed. Thus, the system may use the feedback to determine whether or not a particular footwear model runs true to size. The recommendation system can also use the feedback information to identify products that receive at least a threshold amount of positive feedback or negative feedback, as well as trends among products. For example, the recommendation system may identify a product where a high percentage (e.g., over 90%) of purchasers are providing positive reviews. The recommendation system may then be more likely to provide that item as a recommended item for purchase based upon the historically positive feedback. Additionally, user feedback can be used to evaluate new recommendation algorithms, and determine which, if any, aspects of the new recommendation should be maintained or eliminated. For example, the recommendation system may adjust the recommendation algorithm to place a higher or lower weight on certain fit aspects than others when generating a recommendation. However, if the feedback related to recommendations using the new algorithm are generally negative, the recommendation system may automatically tweak or otherwise alter the new algorithm to change which fit aspects are more highly weighted. Similarly, a system administrator or other software programmer working with the recommendation system may tweak or otherwise alter the new algorithm. Conversely, if the feedback related to recommendations using the new algorithm are generally positive, aspects from the new algorithm may be incorporated into existing algorithms as well. Similarly, the recommendation system can be used to provide suppliers or manufacturers of the items being reviewed with the feedback information. The recommendation system may monitor the feedback information to identify one or more trends in the information such as a collection of reviewers having the same or similar negative feedback regarding an item. If the number of reviewers exceeds a particular threshold as set by the manufacturer (e.g., 25%), the recommendation system may be configured to provide the manufacturer with a notice indicating the negative feedback. In addition to merely providing an indication of feedback, the notices to the manufacturer may include a recommendation that the manufacturer alter one or more physical components of the item, adjust an internal or external dimension of the item, change a material used in the manufacture of an item, or manufacture a new item that combines several liked features (or eliminated several disliked features) from one or more reviewed items. Additionally, feedback received from a particular user can be used to develop a customized product specifically for that user. The system may provide a user's individual feedback to a manufacturer, and the manufacturer may contact the user to inquire about create a customized product specifically for that user. For example, a user may indicate that nearly all fit aspects of a particular shoe are highly rated, but that the overall width of the toe box is too tight. The manufacturer of the shoe may receive the feedback, and contact the user with alternative footwear that may better suit their sizing requirements, or with the option to create a customized product. For example, professional athletes or other similar consumers with a high demand for proper fit, may use the recommendation system and feedback collection mechanism as described herein to work with a manufacturer to produce a properly fitting article of clothing.

Hairstyling Recommendation

In another embodiment, the system can analyze fashion trends based on the user's social network profile, the twitter follow profile, celebrity likes and followings, or expert advice from his/her fashion advisor or hairdresser or experts from magazines and a number of sources. As another alternative or addition, another feature that may be used by mirror to perform similarity searching may correspond to a user's height range to height range; weight-weight, body shape-body shape; age group appropriate as explained above; profession range-profession range; job position-job position; geographic location to geographic location and user profile attributes to celebrity profile attributes. For instance, the height and the width of a user's body figure, as well as a generalization or quantitative description of an overall head-shape (elongated or round shape) may provide another basis for identifying results. Additionally, a user may perform some actions on other user's images. For example: If the user likes the way clothing fits on another user, ii) likes the style of clothing, iii) likes clothing by brand, iv) type of clothing or for any other reason, the user can "like" the image, leave a "comment" on the image, or save the image in his/her digital closet.

The system first captures the user's head 3D model. For style recommendation, the hair color information, the apparel pattern information, the season information, the weather information, the indoor/outdoor information, and the time information may be included in the style characteristics. The recommendation unit may receive a style preference from the user or celebrity or experts as discussed above and search the recommendation style information matched with the received style preference, the face and the style characteristics. In addition, the style recognizer extracts style feature information from the images of the model/celebrity/favorite people that the user indicates directly or indirectly through social network likes and twitter-follow profiles, and recognizes style characteristics using the extracted style feature information. Next, the recommender may search recommendation style information matched with the face and style characteristics recognized in the face recognizer and the style recognizer in the recommendation style table in which the recommendation style information is templated according to face and style characteristics stored in the memory to provide the searched recommendation style information to the user.

The method includes selecting a suitable hair-style wherein the most suitable hair-style can be decided based on consideration of personality and facial features of each selector, along with adopting her preference and request, and at the same time to provide an image map for a hair-style where it can be easily defined what kind of an image the selected hair-style has. The system can analyze a contour of the selector's face and its image are defined for the hair-style brought by an inner line which constitutes a boundary line between a face and a hairline and an outer line which constitutes an outside of the hair style, and wherein it is analyzed whether the selected hair-style is suitable or not with respect to form and balance features and also analyzed whether the selected hair-style is suitable to the image. Analysis for the form and the balance of the hair-style is performed based on five elements; 1. balance between upper and lower parts of the face, 2. Silhouette, 3. Face line, 4. Balancing between head and face, and 5. Total balancing.

Further, analysis for an image of the hair-style is performed based on two elements; 1. An impression on the hair-style and 2. An image gap between face features and a hair-style. Further, with regard to the analysis for a form of the hair-style and its balance, the analysis is performed based on a comparison of a standard proportion between the hair and the face. Further, the system can apply predetermined standards such as those in U.S. Pat. No. 6,333,985 where the standard proportion between the hair and the face is devised as follows:

1. The placement of the eyes is in the center of the whole construction.
2. The proportion ratio between distance from the eyes to the top end of a hair style and distance from the eyes to a bottom end of a jaw is 1:1.
3. The proportion ratio between length of a forehead, distance from the bottom of the forehead to a nose tip and distance from the nose tip to the bottom end of the jaw is 1:1:1.
4. The proportion ratio between the length of the forehead and distance from the top of the forehead at the hairline to the top end of the hair style is 1:0.5.
5. The proportion ratio between length and breadth of the face including the head and hair is, 1.5:1.

Further, an image for "light" and "heavy" is prepared on a perpendicular axis up and down, while the image for "curve line" and "straight line" is prepared on a horizontal axis, and thus representative hair-styles in accordance with these expressed images are arranged.

Further, the image for "light" has some features considered to be youthful such as fluffy loose hair ends, bright in color, having hairs on the forehead, to appear dry, and short to medium size.

On the other hand, the image for "heavy" has features associated with to be calm and an adult image such as stable in the hair-ends, dark in color, no hair on the forehead, to appear wet, and medium to long hair length.

The "curve line" depicts a warm and sweet image, with some features of the hair style waved and curled, a rounded line, and abundant soft hair at the sides.

The "straight line" depicts a cool and clean image, with some features of the style straight, an angular line, and having a long and hard silhouette.

For the face recognizing process and the style recognizing process, the recommendation device detects a face region from a user image transmitted and extracts face feature information from the detected face region. Next, the recommendation device may recognize gender and age from the extracted face feature information or from the user's social network profile. In addition, the recommendation device may extract style feature information from a region of the user image except for the face region and recognize the user style characteristics from the extracted style feature information. The hair style information matched with the face characteristics is used to superimpose the hair onto the user's 3D head model.

Then, the recommendation unit searches the recommendation style information for the characteristics matched with the face and style characteristics recognized in the face recognition unit and the style recognition unit in the recommendation style table according to the characteristics. Here, at least one of the hair style information, makeup style information, and recommendation product information is included in the recommendation style information. The recommendation unit may receive a style preference from the user and search the recommendation style information matched with the received style preference and the characteristics. Further, in the case in which a plurality of recommendation style information is searched, the recommendation unit may prioritize the plurality of searched recommendation style information according to a matched ratio with the characteristics.

FIG. 9 shows an exemplary process to provide trendy new hair recommendations Capture 3D model of head (350)
Remove current hair (352)
Select hair styles from new trends (354)
Morph or project hair onto the 3D model of head (356)
Allow user to iterative change hair styling until satisfied with new hairdo (358)
Allow user to select from a library of wardrobes to provide realistic simulation (360)
Share desired hair style with professional to achieve desired hairdo (362)
Health Monitoring System The 3D camera tracks movements and a 3-D scanner analyzes the viewer's physique. Body recognition software analyzes the body shape to determine weight loss or gain. The smart mirror can provide clothing/jewelry/hair styling suggestions along with augmented reality view of the suggestions so that the user can visualize the impact of the clothing or jewelry or styling. Facial recognition software inspects the face shape to determine health. The smart mirror can provide make-up suggestions along with augmented reality view of the applied suggestions so that the user can visualize the impact of the makeup. The smart mirror can provide non-surgical body augmentation suggestions such as breast/buttock augmentations along with augmented reality view of the body enlargements or size reduction so that the user can visualize the impact of the body enhancement, along with clothing or jewelry or hair styling changes.

Built-in sensors in combination with mobile phone usage pattern and social network communications can detect signs of stress and other mental/emotional health states of the user. The mirrors could also be combined with other health-related apps to keep track of your calorie count, vital signs, fitness level and sleep quality. By extrapolating from the user's current behaviors, vitals and bone and muscle structure, the augmented-reality mirror can forecast the user's future health. The camera can measure breathing activity and/or heart rate of the user in front of the mirror or alternatively the system can bounce WiFi off the chest to detect breathing activity. The mirror highlights hard-to-see changes in the body, such as increased fatigue, minute metabolic imbalances and more. A DNA analyzer can receive swipes from tongue, ear, and saliva, bodily fluids to capture genetic data at a high frequency and such data can be correlated with the fitness wearable devices for signs of health problems. Additionally, the data can be analyzed at a metropolitan level for public health purposes.

FIG. 10 shows an exemplary process to recommend cosmetic enhancements for women, and the process can be applied to men to improve muscular physique appearance Capture 3D model of user (370)

Isolate breast or butt region (372)

Model shape and size of breast or butt increase due to implant (374)

Morph or project the shape/size of breast or butt increase onto the 3D model of user (376)

Allow user to iterative change breast/butt shapes/sizes until satisfied with new shape (378)

Allow user to select from a library of wardrobes to provide realistic simulation (380)

Send desired shape and provide feedback to plastic surgeon to implement desired shape and size (382)

Learning Machine

The system can identify new fashion styles by learning from the user's preferences and/or social network information. For example the system can learn that the user prefers certain celebrities or friends' style and apply this style to the user's fashion style. In some example embodiments, a system and method is shown for fashion matching that interprets a user's style or fashion and finds a match given a set of fashion items. A fashion is a style of dress, while a fashion item includes an article of clothing, jewelry, or anything that is used to denote a style of dress. In addition to the user's existing style and wardrobe, the mirror can add potentially interesting items or styles to the digital closet for the user by automatically retrieving style information from other social networking sites such as Facebook, Twitter, Pinterest, LinkedIn, Instagram and other such social sites for the purpose of more meaningful fashion and style match. Some examples are, the system may retrieve and store user habits, i.e., TV shows, radio programs, songs, record albums, particular artists and actors and movies the user likes as well as user preferences, geographical location, school, other network affiliation, age, likes, recent activity, images viewed, searches etc. and much more variety of information via social network APIs. To incentivize the user to upload more images of themselves thereby building a large database, the system may assign points to the user each time the user interacts with the system. Some examples of system interaction are: a user uploads their own image with a new outfit, the user uploads another user's image and labels it and links it with that user's profile name.

The system can be assisted with a number of learning machines, including neural networks, case-based reasoning, Bayesian networks (including hidden Markov models), or fuzzy systems. The Bayesian networks may include: machine learning algorithms including—supervised learning, unsupervised learning, semi-supervised learning, reinforcement learning, transduction, learning to learn algorithms, or some other suitable Bayesian network. The neural networks may include: Kohonen self-organizing network, recurrent networks, simple recurrent networks, Hopfield networks, stochastic neural networks, Boltzmann machines, modular neural networks, committee of machines, Associative Neural Network (ASNN), holographic associative memory, instantaneously trained networks, spiking neural networks, dynamic neural networks, cascading neural networks, neuro-fuzzy networks, or some other suitable neural network. Further, the neural networks may include: machine learning algorithms including—supervised learning, unsupervised learning, semi-supervised learning, reinforcement learning, transduction, learning to learn algorithms, or some other suitable learning methods.

The system may use knowledge-based components such as a knowledge-based repository (KB). The repository may include clinical information. For example, it may include that "eating salt-rich food causes blood pressure to increase." The information may be stored in a variety of formats based on the type of inference employing them. The knowledge-based repository may act as a repository for some or all of the referenced knowledge. For example, it can include reference values for certain consents and variables used for inference. Accordingly, one or more layers (e.g. a hierarchical pattern processing layer or Pattern Engine) may subscribe to information from the knowledge-based repository. For example, one or more of the services may query the knowledge-based repository when making an inference.

In one embodiment, the knowledge-based repository may aggregate relevant clinical and/or behavioral knowledge from one or more sources. In an embodiment, one or more clinical and/or behavioral experts may manually specify the required knowledge. In another embodiment, an ontology-based approach may be used. For example, the knowledge-based repository may leverage the semantic web using techniques, such as statistical relational learning (SRL). SRL may expand probabilistic reasoning to complex relational domains, such as the semantic web. The SRL may achieve this using a combination of representational formalisms (e.g., logic and/or frame based systems with probabilistic models). For example, the SRL may employ Bayesian logic or Markov logic. For example, if there are two objects—'Asian male' and 'smartness', they may be connected using the relationship 'asian males are smart'. This relationship may be given a weight (e.g., 0.3). This relationship may vary from time to time (populations trend over years/decades). By leveraging the knowledge in the semantic web (e.g., all references and discussions on the web where 'asian male' and 'smartness' are used and associated) the degree of relationship may be interpreted from the sentiment of such references (e.g., positive sentiment: TRUE; negative sentiment: FALSE). Such sentiments and the volume of discussions may then be transformed into weights. Accordingly, although the system originally assigned a weight of 0.3, based on information from semantic web about Asian males and smartness, may be revised to 0.9.

In an embodiment, Markov logic may be applied to the semantic web using two objects: first-order formulae and their weights. The formulae may be acquired based on the semantics of the semantic web languages. In one embodiment, the SRL may acquire the weights based on probability values specified in ontologies. In another embodiment, where the ontologies contain individuals, the individuals can be used to learn weights by generative learning. In some embodiments, the SRL may learn the weights by matching and analyzing a predefined corpora of relevant objects and/or textual resources. These techniques may be used to not only to obtain first-order waited formulae for clinical parameters, but also general information. This information may then be used when making inferences.

For example, if the first order logic is 'obesity causes hypertension, there are two objects involved: obesity and hypertension. If data on users with obesity and as to whether they were diagnosed with diabetes or not is available, then the weights for this relationship may be learnt from the data. This may be extended to non-clinical examples such as person's mood, beliefs etc.

The pattern recognizer may use the temporal dimension of data to learn representations. The pattern recognizer may include a pattern storage system that exploits hierarchy and analytical abilities using a hierarchical network of nodes. The nodes may operate on the input patterns one at a time. For every input pattern, the node may provide one of three operations: 1. Storing patterns, 2. Learning transition probabilities, and 3. Context specific grouping.

A node may have a memory that stores patterns within the field of view. This memory may permanently store patterns and give each pattern a distinct label (e.g. a pattern number). Patterns that occur in the input field of view of the node may be compared with patterns that are already stored in the memory. If an identical pattern is not in the memory, then the input pattern may be added to the memory and given a distinct pattern number. The pattern number may be arbitrarily assigned and may not reflect any properties of the pattern. In one embodiment, the pattern number may be encoded with one or more properties of the pattern.

In one embodiment, patterns may be stored in a node as rows of a matrix. In such an embodiment, C may represent a pattern memory matrix. In the pattern memory matrix, each row of C may be a different pattern. These different patterns may be referred to as C-1, C-2, etc., depending on the row in which the pattern is stored.

The nodes may construct and maintain a Markov graph. The Markov graph may include vertices that correspond to the store patterns. Each vertex may include a label of the pattern that it represents. As new patterns are added to the memory contents, the system may add new vertices to the Markov graph. The system may also create a link between to vertices to represent the number of transition events between the patterns corresponding to the vertices. For example, when an input pattern is followed by another input pattern j for the first time, a link may be introduced between the vertices i and j and the number of transition events on that link may be set to 1. System may then increment the number of transition counts on the link from i and j whenever a pattern from i to pattern j is observed. The system may normalize the Markov graph such that the links estimate the probability of a transaction. Normalization may be achieved by dividing the number of transition events on the outgoing links of each vertex by the total number of transition events from the vertex. This may be done for all vertices to obtain a normalized Markov graph. When normalization is completed, the sum of the transition probabilities for each node should add to 1. The system may update the In some embodiments of the present disclosure, a user or healthcare provider may create a user profile comprising, e.g., identifying, characterizing, and/or medical information, including information about a user's medical history, profession, and/or lifestyle. Further examples of information that may be stored in a user profile includes diagnostic information such as family medical history, medical symptoms, duration of hypertension, localized vs. general hypertension, etc. Further contemplated as part of a user profile are non-pharmacologic treatment(s) (e.g., chiropractic, radiation, holistic, psychological, acupuncture, etc.), lifestyle characteristics (e.g., diet, alcohol intake, smoking habits), cognitive condition, behavioral health, and social well-being.

The methods and systems disclosed herein may rely on one or more algorithm(s) to analyze one or more of the described metrics. The algorithm(s) may comprise analysis of data reported in real-time, and may also analyze data reported in real-time in conjunction with auxiliary data stored in a hypertension management database. Such auxiliary data may comprise, for example, historical user data such as previously-reported hypertension metrics (e.g., hypertension scores, functionality scores, medication use), personal medical history, and/or family medical history. In some embodiments, for example, the auxiliary data includes at least one set of hypertension metrics previously reported and stored for a user. In some embodiments, the auxiliary data includes a user profile such as, e.g., the user profile described above. Auxiliary data may also include statistical data, such as hypertension metrics pooled for a plurality of users within a similar group or subgroup. Further, auxiliary data may include clinical guidelines such as guidelines relating to hypertension management, including evidence-based clinical practice guidelines on the management of acute and/or chronic hypertension or other chronic conditions.

Analysis of a set of hypertension metrics according to the present disclosure may allow for calibration of the level, degree, and/or quality of hypertension experienced by providing greater context to user-reported data. For example, associating a hypertension score of 7 out of 10 with high functionality for a first user, and the same score with low functionality for a second user may indicate a relatively greater debilitating effect of hypertension on the second user than the first user. Further, a high hypertension score reported by a user taking a particular medication such as opioid analgesics may indicate a need to adjust the user's treatment plan. Further, the methods and systems disclosed herein may provide a means of assessing relative changes in a user's distress due to hypertension over time. For example, a hypertension score of 5 out of 10 for a user who previously reported consistently lower hypertension scores, e.g., 1 out of 10, may indicate a serious issue requiring immediate medical attention.

Any combination(s) of hypertension metrics may be used for analysis in the systems and methods disclosed. In some embodiments, for example, the set of hypertension metrics comprises at least one hypertension score and at least one functionality score. In other embodiments, the set of hypertension metrics may comprise at least one hypertension score, at least one functionality score, and medication use.

More than one set of hypertension metrics may be reported and analyzed at a given time. For example, a first set of hypertension metrics recording a user's current status and a second set of hypertension metrics recording the user's status at an earlier time may both be analyzed and may also be used to generate one or more recommended actions.

Each hypertension metric may be given equal weight in the analysis, or may also be given greater or less weight than other hypertension metrics included in the analysis. For example, a functionality score may be given greater or less weight with respect to a hypertension score and/or medication use. Whether and/or how to weigh a given hypertension metric may be determined according to the characteristics or needs of a particular user. As an example, User A reports a hypertension score of 8 (on a scale of 1 to 10 where 10 is the most severe hypertension) and a functionality score of 9 (on a scale of 1 to 10 where 10 is highest functioning), while User B reports a hypertension score of 8 but a functionality score of 4. The present disclosure provides for the collection, analysis, and reporting of this information, taking into account the differential impact of one hypertension score on a user's functionality versus that same hypertension score's impact on the functionality of a different user.

Hypertension metrics may undergo a pre-analysis before inclusion in a set of hypertension metrics and subsequent application of one or more algorithms. For example, a raw score may be converted or scaled according to one or more algorithm(s) developed for a particular user. In some embodiments, for example, a non-numerical raw score may be converted to a numerical score or otherwise quantified prior to the application of one or more algorithms. Users and healthcare providers may retain access to raw data (e.g., hypertension metric data prior to any analysis)

Algorithm(s) according, to the present disclosure may analyze the set of hypertension metrics according to any suitable methods known in the art. Analysis may comprise, for example, calculation of statistical averages, pattern recognition, application of mathematical models, factor analysis, correlation, and/or regression analysis. Examples of analyses that may be used herein include, but are not limited to, those disclosed in U.S. Patent Application Publication No. 2012/0246102 A1 the entirety of which is incorporated herein by reference.

The present disclosure further provides for the determination of an aggregated hypertension assessment score. In some embodiments, for example, a set of pairs metrics may be analyzed to generate a comprehensive and/or individualized assessment of hypertension by generating a composite or aggregated score. In such embodiments, the aggregated score may include a combination of at least one hypertension score, at least one functionality score, and medication use. Additional metrics may also be included in the aggregated score. Such metrics may include, but are not limited to, exercise habits, mental well-being, depression, cognitive functioning, medication side effects, etc. Any of the aforementioned types of analyses may be used in determining an aggregated score.

The algorithm(s) may include a software program that may be available for download to an input device in various versions. In some embodiments, for example, the algorithm(s) may be directly downloaded through the Internet or other suitable communications means to provide the capability to troubleshoot a health issue in real-time. The algorithm(s) may also be periodically updated, e.g., provided content changes, and may also be made available for download to an input device.

The methods presently disclosed may provide a healthcare provider with a more complete record of a user's day-to-day status. By having access to a consistent data stream of hypertension metrics for a user, a healthcare provider may be able to provide the user with timely advice and real-time coaching on hypertension management options and solutions. A user may, for example, seek and/or receive feedback on hypertension management without waiting for an upcoming appointment with a healthcare provider or scheduling a new appointment. Such real-time communication capability may be especially beneficial to provide users with guidance and treatment options during intervals between appointments with a healthcare provider. Healthcare providers may also be able to monitor a user's status between appointments to timely initiate, modify, or terminate a treatment plan as necessary. For example, a user's reported medication use may convey whether the user is taking too little or too much medication. In some embodiments, an alert may be triggered to notify the user and/or a healthcare provider of the amount of medication taken, e.g., in comparison to a prescribed treatment plan. The healthcare provider could, for example, contact the user to discuss the treatment plan. The methods disclosed herein may also provide a healthcare provider with a longitudinal review of how a user responds to hypertension over time. For example, a healthcare provider may be able to determine whether a given treatment plan adequately addresses a user's needs based on review of the user's reported hypertension metrics and analysis thereof according to the present disclosure.

Analysis of user data according to the methods presently disclosed may generate one or more recommended actions that may be transmitted and displayed on an output device. In some embodiments, the analysis recommends that a user make no changes to his/her treatment plan or routine. In other embodiments, the analysis generates a recommendation that the user seek further consultation with a healthcare provider and/or establish compliance with a prescribed treatment plan. In other embodiments, the analysis may encourage a user to seek immediate medical attention. For example, the analysis may generate an alert to be transmitted to one or more output devices, e.g., a first output device belonging to the user and a second output device belonging to a healthcare provider, indicating that the user is in need of immediate medical treatment. In some embodiments, the analysis may not generate a recommended action. Other recommended actions consistent with the present disclosure may be contemplated and suitable according to the treatment plans, needs, and/or preferences for a given user.

The present disclosure further provides a means for monitoring a user's medication use to determine when his/her prescription will run out and require a refill. For example, a user profile may be created that indicates a prescribed dosage and frequency of administration, as well as total number of dosages provided in a single prescription. As the user reports medication use, those hypertension metrics may be transmitted to a server and stored in a database in connection with the user profile. The user profile stored on the database may thus continually update with each added metric and generate a notification to indicate when the prescription will run out based on the reported medication use. The notification may be transmitted and displayed on one or more output devices, e.g., to a user and/or one or more healthcare providers. In some embodiments, the one or more healthcare providers may include a pharmacist. For example, a pharmacist may receive notification of the anticipated date a prescription will run out in order to ensure that the prescription may be timely refilled.

User data can be input for analysis according to the systems disclosed herein through any data-enabled device including, but not limited to, portable/mobile and stationary communication devices, and portable/mobile and stationary computing devices. Non-limiting examples of input devices suitable for the systems disclosed herein include smart phones, cell phones, laptop computers, netbooks, personal computers (PCs), tablet PCs, fax machines, personal digital assistants, and/or personal medical devices. The user interface of the input device may be web-based, such as a web page, or may also be a stand-alone application. Input devices may provide access to software applications via mobile and wireless platforms, and may also include web-based applications.

The input device may receive data by having a user, including, but not limited to, a user, family member, friend, guardian, representative, healthcare provider, and/or caregiver, enter particular information via a user interface, such as by typing and/or speaking. In some embodiments, a server may send a request for particular information to be entered by the user via an input device. For example, an input device may prompt a user to enter sequentially a set of hypertension metrics, e.g., a hypertension score, a functionality score, and information regarding use of one or more medications (e.g., type of medication, dosage taken, time of day, route of administration, etc.). In other embodiments, the user may enter data into the input device without first receiving a prompt. For example, the user may initiate an application or web-based software program and select an option to enter one or more hypertension metrics. In some embodiments, one or more hypertension scales and/or functionality scales may be preselected by the application or software program. For example, a user may have the option of selecting the type of hypertension scale and/or functionality scale for reporting hypertension metrics within the application or software program. In other embodiments, an application or software program may not include preselected hypertension scales or functionality scales such that a user can employ any hypertension scale and/or functionality scale of choice.

In exemplary system for mining health data for precision medicine, medical grade data from the user's physician/hospital, along with 3D models, and lab test equipment data are stored in a database. Omic test equipment also generates data that is stored in another database. EHR data from primary care physician (PHP), emergency room physicians (ER), and in-patient care data is also stored in a database. These databases form a clinical data repository that contains medical diagnosis and treatment information. The clinical data is high grade medical information that is secured by patient privacy laws such as HIPPA. One exemplary process for improving healthcare using precision medicine includes:

obtain clinical data from mirror and 3d party laboratory test equipment
    obtain clinical data from one or more omic test equipment
    obtain clinical data from a primary care physician database
    obtain clinical data from a specialist physician database
    obtain clinical data from an emergency room database
    obtain clinical data from an in-patient care database
    save the clinical data into a clinical data repository
    obtain health data from fitness devices and from mobile phones
    obtain behavioral data from social network communications and mobile device usage patterns
    save the health data and behavioral data into a health data repository separate from the clinical data repository
    mine the clinical data repository and health data repository for patients sharing similarity with the subject, including one or more similar biomarkers associated with health conditions
    identify at least one similar health conditions and identifying one or more corrective actions recorded in the repository and the result of each action for the one or more health conditions;
    present the corrective action and result to the subject and recommending an action to reduce risk from the predicted health condition
    monitor the health condition using updates in the clinical data repository and health data repository In another embodiment for cost effective health maintenance, the system includes a method of insuring a subject for cancer, by:

enrolling the subject into a cost-saving program;
    receiving a body sample during routine periodic examinations and characterizing the subject's omic information with a DNA sequencer; and
    using historical omic information to detect an occurrence of a disease such as cancer before the subject is suspected of having the disease; and
    proactively recommending early treatments based on the omic information received at each time interval to cost-effectively control disease.

Another exemplary process for applying the agents to a weight loss treatment scenario. The general goals of weight loss and management are: (1) at a minimum, to prevent further weight gain; (2) to reduce body weight; and (3) to maintain a lower body weight over the long term. The initial goal of weight loss therapy is to reduce body weight by approximately 10 percent from baseline. If this goal is achieved, further weight loss can be attempted, if indicated through further evaluation. A reasonable time line for a 10 percent reduction in body weight is 6 months of therapy. For overweight patients with BMIs in the typical range of 27 to 35, a decrease of 300 to 500 kcal/day will result in weight losses of about ½ to 1 lb/week and a 10 percent loss in 6 months. For more severely obese patients with BMIs>35, deficits of up to 500 to 1,000 kcal/day will lead to weight losses of about 1 to 2 lb/week and a 10 percent weight loss in 6 months. Weight loss at the rate of 1 to 2 lb/week (calorie deficit of 500 to 1,000 kcal/day) commonly occurs for up to 6 months. After 6 months, the rate of weight loss usually declines and weight plateaus because of a lesser energy expenditure at the lower weight.

The agents are adaptive to the patient and allow for program modifications based on patient responses and preferences. For example, the agent can be modified for weight reduction after age 65 to address risks associated with obesity treatment that are unique to older adults or those who smoke.

The event handler can be coded to:
    Receive message from patient or doctor (20)
    Determine user treatment modality (22)
    For each modality
    Determine relevant rules (26)
    For each rule
    Determine responsive agent(s) (30)
    For each agent
    Execute agent program (34)
    Get input from service provider if needed (36)
    Format & send the message for the patient's mobile device (38)

The system processes a communication from a patient according to one or more treatment scenarios. Each treatment scenario is composed of one or more rules to be processed in a sequence that can be altered when invoking certain agents.

The if then rules can be described to the system using a graphical user interface that runs on a web site, a computer, or a mobile device, and the resulting rules are then processed by a rules engine. In one embodiment, the if then rules are entered as a series of dropdown selectors whose possible values are automatically determined and populated for user selection to assist user in accurately specifying the rules.

Other risk factors can be considered as rules by the agent, including physical inactivity and high serum triglycerides (>200 mg/dL). When these factors are present, patients can be considered to have incremental absolute risk above that estimated from the preceding risk factors. Quantitative risk contribution is not available for these risk factors, but their presence heightens the need for weight reduction in obese persons.

One embodiment determines high interest disease- and drug-related variants in the pateint's genome and identifies top diseases with the highest probabilities. For each disease, the system determines the pretest probability according to the patient age, gender, and ethnicity. The system then determines the independent disease-associated SNVs used to calculate the subject's disease probability. For each disease, for example type 2 diabetes, the system determines probability using independent SNVs, a likelihood ratio (LR), number of studies, cohort sizes, and the posttest probability. Blood pressure and blood glucose trend measurements are also determined.

A patient motivation agent evaluates the following factors: reasons and motivation for weight reduction; previous history of successful and unsuccessful weight loss attempts; family, friends, and work-site support; the patient's understanding of the causes of obesity and how obesity contributes to several diseases; attitude toward physical activity; capacity to engage in physical activity; time availability for weight loss intervention; and financial considerations. In addition to considering these issues, the system can heighten a patient's motivation for weight loss and prepare the patient for treatment through normative messaging and warnings. This can be done by enumerating the dangers accompanying persistent obesity and by describing the strategy for clinically assisted weight reduction. Reviewing the patients' past attempts at weight loss and explaining how the new treatment plan will be different can encourage patients and provide hope for successful weight loss.

In an exemplary system for providing precision medicine, historical data from a large population is received and provided to a learning engine. The learning engine clusters the population into groups of similar characteristics and then creates a social network of patients who share enough health/medical similarity that they are apt to share many medical issues. Thus a user's likelihood of contracting a disease might be evaluated by knowing the disease status of other users in the same influence cluster or neighborhood, whether they are closely connected to that user or not.

The system, generally denoted by reference numeral 100, comprises one or more central processing units CP1 ... CPn, generally denoted by reference numeral 110. Embodiments comprising multiple processing units 110 are preferably provided with a load balancing unit 115 that balances processing load among the multiple processing units 110. The multiple processing units 110 may be implemented as separate processor components or as physical processor cores or virtual processors within a single component case. In a typical implementation the computer architecture 100 comprises a network interface 120 for communicating with various data networks, which are generally denoted by reference sign DN. The data networks DN may include local-area networks, such as an Ethernet network, and/or wide-area networks, such as the internet. In some implementations the computer architecture may comprise a wireless network interface, generally denoted by reference numeral 125. By means of the wireless network interface, the computer 100 may communicate with various access networks AN, such as cellular networks or Wireless Local-Area Networks (WLAN). Other forms of wireless communications include short-range wireless techniques, such as Bluetooth and various "Bee" interfaces, such as XBee, ZigBee or one of their proprietary implementations. Depending on implementation, a user interface 140 may comprise local input-output circuitry for a local user interface, such as a keyboard, mouse and display (not shown). The computer architecture also comprises memory 150 for storing program instructions, operating parameters and variables. Reference numeral 160 denotes a program suite for the server computer 100. Reference number 115-135 denotes an optional interface by which the computer obtains data from external sensors, analysis equipment or the like.

In some embodiments the data processing system is coupled with equipment that determines an organism's genotype from an in-vitro sample obtained from the organism. In other embodiments the genotypes are determined elsewhere and the data processing system may obtain data representative of the genotype via any of its data interfaces.

One exemplary sensor communicating with one of the interfaces 115-135 receives a biologic sample from an individual such as a bodily fluid (such as urine, saliva, plasma, or serum) or feces or a tissue sample (such as a buccal tissue sample or buccal cell). The biologic sample can then be used to perform a genome scan. For example, DNA arrays can be used to analyze at least a portion of the genomic sequence of the individual. Exemplary DNA arrays include GeneChip Arrays, GenFlex Tag arrays, and Genome-Wide Human SNP Array 6.0 (available from Affymetrix, Santa Clara, Calif.). In other examples, DNA sequencing with commercially available next generation sequencing (NGS) platforms is generally conducted: DNA sequencing libraries are generated by clonal amplification by PCR in vitro; then the DNA is sequenced by synthesis, such that the DNA sequence is determined by the addition of nucleotides to the complementary strand rather through chain-termination chemistry; next, the spatially segregated, amplified DNA templates are sequenced simultaneously in a massively parallel fashion without the requirement for a physical separation step. For microbiome analysis, cotton swabs are applied to forehead, behind ears, nose, among others, and fecal samples are analyzed using DNA sequencing machines. In certain embodiments, whole or partial genome sequence information is used to perform the genome scans. Such sequences can be determined using standard sequencing methods including chain-termination (Sanger dideoxynucleotide), dye-terminator sequencing, and SOLiD™ sequencing (Applied Biosystems). Whole genome sequences can be cut by restriction enzymes or sheared (mechanically) into shorter fragments for sequencing. DNA sequences can also be amplified using known methods such as PCR and vector-based cloning methods (e.g., *Escherichia coli*).

The sensors connecting to interfaces 115-135 can also include fitness sensors such as wearable watches/clothing/shoes that monitor activity, heart rate, ECG, blood pressure, blood oxygen level, among others. The sensors 115-135 can also detect purchase activities and on-line activities that reflect the user's health habits. For example, the sensors can be a data feed that picks up data relating to grocery purchases, food expenses, restaurant spending.

In yet other examples, the sensors connecting to interfaces 115-135 can be sensors in a phone. For example, in depression sensor, the phone can detect a person's activity and correlate to depression: people who stuck to a regular pattern of movement tended to be less depressed as people with mental health problems in general have disrupted circadian rhythms and a depressed mood may pull a user off her routine. Depressed people also spends more time on their phones or browsing aimlessly, as depressed people tend to start avoiding tasks or things they have to do, particularly when they're uncertain.

In addition to sensor captured healthcare data, healthcare data refers to any data related or relevant to a patient. Healthcare data may include, but is not limited to, fitness data and healthcare-related financial data. Clinical data, as used herein, refers to any healthcare or medical data particular to a patient. In embodiments, clinical data can be medical care or healthcare data resulting from or associated with a health or medical service performed in association with a clinician in a healthcare environment (e.g., lab test, diagnostic test, clinical encounter, ecare, evisit, etc.). Clinical data may include, but is not limited to, a health history of a patient, a diagnosis, a clinician assessment, clinician narrative, a treatment, a family history (including family health history and/or family genetics), an immunization record, a medication, age, gender, date of birth, laboratory values, diagnostics, a test result, an allergy, a reaction, a procedure performed, a social history, an advanced directive, frequency and/or history of healthcare facility visits, current healthcare providers and/or current healthcare provider location, preferred pharmacy, prescription benefit management data, an alert, claims data, a vital, data traditionally captured at the point of care or during the care process, a combination thereof, and the like. In the same or alternative embodiments, the clinical data may include medical compliance information. In certain embodiments, medical compliance information refers to a level of compliance of a particular patient with one or more prescribed medical treatments, such as medications, diet, physical therapy, follow up healthcare visits, and the like. In one or more embodiments, the clinical data may include data obtained from the natural language processing of one or more clinical assessments and/or clinical narratives.

By engaging and empowering patients to take an active role in data collection, the footwear applies inconspicuous foot data with analytics to improve health. One embodiment uses Google Maps to display health activity traffic; showing healthcare patterns based on real time reporting of anonymous data from healthcare footware devices. Healthcare organizations can tap the power of that data to engage patients and develop more effective and more personalized approaches to care, thereby lowering the overall cost of care.

The system identifies pre-detectable characteristics of a health condition, such that future incidents of the health condition may be predicted, i.e., before the health condition occurs for disease prevention. One implementation includes capturing data from mobile fitness devices and establishing a plurality of health related characteristics associated with the population including walking status, weight, calorie burn. The characteristics include a plurality of pre-detectable characteristics with a relationship between the health related characteristics and at least one health condition, and analyzing at least a portion of said population in response to the relationship.

Another embodiment includes establishing at least one pre-detectable characteristic associated with a health condition, applying an intervention in response to the characteristic, monitoring a success characteristic of the intervention, and determining a cause of the success characteristic.

Another embodiment builds a repository of health related characteristics associated with the population, the characteristics including a plurality of pre-detectable characteristics; and a processor configured to receive the health related characteristics, establish a relationship between the health related characteristics and at least one health condition, and analyzing at least a portion of the population in response to said relationship.

A population, as used herein, is any group of members. The population may include a high level of members, for example a group including one or more of the five kingdoms of living things, or a subgroup, for example a group including humans of a certain age range. The population may include living and/or dead members. The analysis may include predicting a likelihood of a member developing the health condition, in response to the relationship. The health condition may be any type of physical or mental health condition, disease, and/or ailment. In addition, the analysis may include predicting the incidence of the health condition. The analysis may also include performing a simple yes/no prediction regarding whether a member will likely develop the health condition. The analysis may be used to enable the management of a health care program, such as a program associated with a corporation, or a program offered to the public by a health care consultant or provider. If the analysis is associated with a corporation's healthcare program, the population may include some or all of the employees and retirees of the corporation, and associated spouses and dependents. The population may include other associated groups of the corporation, such as consultants, contractors, suppliers and/or dealers. The population may include participants from multiple corporations and/or the general public. If the health care program is offered to the public, the population may include members of the public, organizations, and/or corporations.

The health related characteristics may include a plurality of health characteristics, lifestyle characteristics and/or family health characteristics associated with the members of the population. Health characteristics may include characteristics indicative of a specific member's health. For example, lifestyle characteristic may include weight, heart rate, walking gait, sitting gait, running gait, exercise or activity as detected by accelerometers, diet, and other factors detectable by fitness devices such as watches, phones, or foot sensors detailed above. For other example, health characteristic may include medical characteristics (e.g., what medical visits, processes, procedures, or test have been performed associated with the member, the number of days the member has spent in a medical facility (e.g., a hospital), the number of visits the person has made to a doctor, etc.), drug characteristics (e.g., what type and amount of drugs are being consumed), a death characteristic (e.g., information associated with a death certificate), an absenteeism characteristic, disability characteristics, characteristics associated with existing health conditions, etc. Family health characteristics associated with the member may include information associated with the family medical history of a specific member. For example, a history of a particular health risk within the family, e.g., heart failure, cancer, high blood pressure, diabetes, anxiety, stress, etc. Lifestyle characteristic may include a specific member's behavior characteristic(s), of which some or all may be modifiable lifestyle characteristics. A modifiable lifestyle characteristic may include an exercise characteristic (e.g., does the member exercise, how often, what is the exercise, etc.) and/or a nutrition characteristic (e.g., what types of food does the member eat, and how often). Nutrition characteristics may also include the amount of salt consumed during a designated period (e.g., a day), and the amount of fat and/or saturated fat consumed during a designated period. In addition, modifiable lifestyle characteristics may include whether the member drinks alcohol (and if so how much), a drug intake characteristic, (i.e., does the member take drugs, and if so how often, what kind, and how much), a weight characteristic (e.g., what does the member weigh, what is the member's desired weight, is the member on a diet, what is the member's weight indicator e.g., obese, slightly overweight, underweight, normal, etc.), a smoking characteristic (does the member smoke and if so how much), a safety characteristic (what are the member's driving characteristics e.g., does the member where seat belts, have one or more infractions associated with driving under the influence, or speeding tickets, etc.). In addition, modifiable lifestyle characteristics may include a hypertension characteristic, a stress characteristic, a self-care characteristic, a self-efficacy characteristic, a readiness to change characteristics, and a prophylactic aspirin therapy characteristic.

One method for performing population health management includes establishing a plurality of health related characteristics associated with the population; establishing a relationship between the health related characteristics and at least one health condition; and analyzing at least a portion of said population in response to said relationship. The system can predict a likelihood of at least one of said members developing said at least one health condition, in response to said relationship and/or the members health related characteristics. The system can determine a prevalence of a health condition within said population in response to said health related characteristics. The plurality of health related characteristics associated with said population can be done by establishing a plurality of self-reported characteristics associated with at least a portion of said population. A prevalence of the health condition can be determined by: establishing a plurality of claims associated with at least one os said members, said claims including at least one of a drug claim and a medical claim; cross checking said plurality of claims (such as over a period of time, or over a number of tests); and establishing said prevalence in response to said cross checked claims. The system includes predicting a member's likelihood of developing a condition with a stage of said condition in response to said prediction. The system can predict a time period associated with said development. The system can classify said population in response to said prediction, and then prioritize treatment of the population in response to said prediction.

The system can recommend an intervention in response to said predicted likelihood of development. This can be done by establishing a plurality of intervention recommendations associated with said condition; establishing a success characteristics of said recommended intervention; establishing at least one of a readiness to change characteristic and a self-efficacy characteristic of said member; and recommending said intervention in response to said plurality of intervention recommendations, associated intervention success characteristics, and member health related characteristics, said health characteristics including said self-efficacy and said readiness to change characteristic.

The system can monitor failure/successful characteristic of said intervention, and determining causes resulting in said success characteristic. The system can capture a plurality of self-reported data associated with at least a portion of said population having said condition. The self-reported data includes at least one of a lifestyle characteristic, a family history characteristic, and a health characteristic. The predictive relationship can be done by establishing at least one objective of said relationship; dynamically selecting a statistical analysis technique in response to said objective; and establishing said relationship in response to said statistical analysis technique. The predictive relationship can be applied to at least a portion of said population; and predicting a likelihood of developing said condition in response to said application.

The system can be configured to analyze the health of a population having multiple members. In one embodiment, the method includes the steps of establishing a plurality of health related characteristics associated with the population, the characteristics including a plurality of pre-detectable characteristics, establishing a relationship between the health related characteristics and the health condition, and predicting an incident of the health condition associated with at least one of the members, in response to the relationship. The health condition may be any type of physical or mental health condition, disease, and/or ailment. For exemplary purposes the method and system will be discussed as they may relate to the health condition diabetes. A repository of health related characteristics associated with a population may be collected. The health related characteristics may be collected through sources such as medical claims, drug claims, and self-reported information. The characteristics may include health characteristics, lifestyle characteristics, and family history characteristics. The characteristics may include the amount of saturated fat, unsaturated fat, fiber, salt, alcohol, cholesterol, etc. that a member consumes in a give time period. The characteristics may include weight characteristic, such as a member's weight, BMI (Body Mass Index), abdominal girth, etc. The characteristics may also include the person's blood pressure, standing heart rate, exercise habits (type and duration), and whether the member has hypertension. The health related characteristics of the population may be analyzed to establish the prevalence of diabetes among the population. For example, a medical claim having an ICD code with the prefix 250 is an indicator that the member may have diabetes. In addition, drug claims having a medication code descriptive of an anti-diabetes medication are indicators that the member has diabetes. The medical and/or drug claims are analyzed to determine if two claims indicating a member may have diabetes, and that are separated by at least three months, occur. If two claims meeting the criteria are identified, then the member is determined to have diabetes. For example, if two separate ICD codes occur, separated by at least three months, or one such ICD code occurs and one drug code for anti diabetes medication occur, e.g., separated by at least three months, then the member may be determined to have diabetes.

Once the population has been analyzed to establish who has diabetes, the historical health related characteristics of the diabetics are then used to establish a relationship between diabetes and the health related characteristics. For example, the health related characteristics are used to establish a neural network model, or regression model. The trained neural network and/or regression model will then be able to predict the likelihood a member of the population will acquire diabetes. In one embodiment, the neural network will also be able to establish who has, or may acquire, the related diabetic characteristics of metabolic syndrome and or glucose intolerance. Alternatively, these may be inputs to the neural network if available.

The established relationship may be reviewed to determine what the pre-detectable characteristics associated with diabetes are. For example, it may be determined that salt intake, consumption of saturated fats, and alcohol consumption are three leading pre-detectable characteristics of acquiring diabetes. In addition, it may be determined that smoking is not a pre-detectable characteristic associated with diabetes. The population may then be reviewed using the established relationship. The health related characteristics of each member of the population not known to have diabetes may be analyzed using the relationship. The analysis may indicate the likelihood the person will acquire diabetes (e.g., 75% likely). In addition, the pre-detectable characteristics associated with diabetes that are exhibited by the person may be identified. In this manner, the likelihood of the acquiring diabetes may be established along with what pre-detectable characteristics are the primary contributors to this particular member having diabetes.

Once the population's health related characteristics are analyzed, the population may be ranked by the individual member's likelihood of acquiring diabetes. In this manner, the type of intervention may be recommended based on the risk of acquiring diabetes, and the pre-detectable characteristics the member exhibits. In one embodiment, the interventions may be recommended by using another relationship (or an elaboration of the predictive relationship) to automatically make the recommendation based on the health related characteristics of the member, which may include the likelihood of acquiring diabetes and specific pre-detectable characteristics exhibited, self-efficacy and readiness to change characteristics of the member, etc. In one embodiment, the intervention may include additional questionnaires or interviews to acquire more specific information associated with diabetes from the individual. Other forms of intervention include one on one counseling to convince the member of the seriousness of diabetes, the risk of acquiring diabetes associated with them, the ability to delay or prevent the onset of diabetes by changing specified lifestyle characteristics, and the specific actions the member may take to modify specific aspects of their lifestyle associated with the pre-detectable characteristics. For example, if dietary issues are causing the member to be overweight, the intervention may include, suggested changes to dietary consumption, cookbooks directed towards the desired diet, or even corporate sponsored diet counseling or involvement in a commercial diet control program. The specific intervention recommended may be based on the likelihood of acquiring diabetes the person has, the members willingness to change their diet and belief that they will be successful in long term dietary change, and how much of a factor dietary issues were in establishing this particular members likelihood of acquiring diabetes.

Once the intervention recommendation is provided additional monitoring may occur to determine if the member followed through with the recommendation (including why they did or didn't follow through), whether the intervention helped reduce the targeted characteristic (e.g., the targeted pre-detectable characteristic), and when the intervention did reduce the targeted characteristics, whether the ultimate occurrence of diabetes was either delayed (which may be a subjective determination) or prevented altogether. The results of this monitoring may then be used to update the established relationships. In addition, as incidents of diabetes occur, the health related characteristics of effected member may be used to further refine the established predictive relationship. In this manner, the health of the population may be analyzed and managed relative to diabetes.

The system can receive data from electronic medical records (EMRs), activity data from patient watches and wearable devices, population demographic information from govt databases, consumer profile information from credit card companies or consumer sales companies, provider (doctor, dentist, caregiver) entered information, one or more output registry databases. The EMRs may span multiple applications, multiple providers, multiple patients, multiple conditions, multiple venues, multiple facilities, multiple organizations, and/or multiple communities. Embodiments of the EMRs may include one or more data stores of healthcare records, which may include one or more computers or servers that facilitate the storing and retrieval of the healthcare records. In some embodiments, one or more EMRs may be implemented as a cloud-based platform or may be distributed across multiple physical locations. Example embodiments of the EMRs may include hospital, ambulatory, clinic, health exchange, and health plan records systems. The EMRs may further include record systems, which store real-time or near real-time patient (or user) information, such as wearable, bedside, or in-home patient monitors, for example. It is further contemplated that embodiments of the EMRs may use distinct clinical ontologies, nomenclatures, vocabularies, or encoding schemes for clinical information, or clinical terms. Further, in some embodiments, the EMRs may be affiliated with two or more separate health care entities and/or venues that use two or more distinct nomenclatures.

In embodiments, the EMRs described herein may include healthcare data. As used herein, healthcare data refers to any healthcare or medical care data related or relevant to a patient. Healthcare data may include, but is not limited to, clinical data and healthcare-related financial data. Clinical data, as used herein, refers to any healthcare or medical data particular to a patient. In embodiments, clinical data can be medical care or healthcare data resulting from or associated with a health or medical service performed in association with a clinician in a healthcare environment (e.g., lab test, diagnostic test, clinical encounter, ecare, evisit, etc.). Clinical data may include, but is not limited to, a health history of a patient, a diagnosis, a clinician assessment, clinician narrative, a treatment, a family history (including family health history and/or family genetics), an immunization record, a medication, age, gender, date of birth, laboratory values, diagnostics, a test result, an allergy, a reaction, a procedure performed, a social history, an advanced directive, frequency and/or history of healthcare facility visits, current healthcare providers and/or current healthcare provider location, preferred pharmacy, prescription benefit management data, an alert, claims data, a vital, data traditionally captured at the point of care or during the care process, a combination thereof, and the like. In the same or alternative embodiments, the clinical data may include medical compliance information. In certain embodiments, medical compliance information refers to a level of compliance of a particular patient with one or more prescribed medical treatments, such as medications, diet, physical therapy, follow up healthcare visits, and the like. In one or more embodiments, the clinical data may include data obtained from the natural language processing of one or more clinical assessments and/or clinical narratives.

In certain embodiments, healthcare-related financial data can refer to any financial information relevant to a patient, such as insurance data, claims data, payer data, etc. Such healthcare data (e.g., clinical data and healthcare-related financial data) may be submitted by a patient, a care provider, a payer, etc. In certain embodiments where the healthcare data is being submitted by anyone other than the patient, the patient may be required to approve of such submission and/or may opt-in to or opt-out of having such healthcare data being submitted.

In embodiments, activity data can refer to health actions or activities performed by a patient outside of, or remote from, a healthcare environment. Embodiments of activity data may include one or more data stores of activity data, which may include one or more computers or servers that facilitate the storing and retrieval of the activity data. In some embodiments, the activity data may be implemented as a cloud-based platform or may be distributed across multiple physical locations. Example embodiments of the activity data may include nutrition information and/or exercise information for a patient. In certain embodiments, at least a portion of the activity data may be recorded utilizing a personal fitness tracker, a smart phone, and/or an application provided by a smart phone. In various embodiments, the activity data may include data obtained from a patient's car. For example, in such embodiments, the activity data include data on the amount of driving the patient does versus the amount of walking the patient does.

In one or more embodiments, the activity data may be submitted by a patient, a third party associated with a personal fitness tracker and/or smart phone (such as a software developer or device manufacturer), a care provider, a payer, etc. In certain embodiments where the activity is being submitted by anyone other than the patient, the patient may be required to approve of such submission and/or may opt-in to or opt-out of having such healthcare data being submitted.

The patient and/or population demographic information may include age, gender, date of birth, address, phone number, contact preferences, primary spoken language, technology access (e.g., internet, phone, computer, etc.), transportation (e.g., common modes of transportation), education level, motivation level, work status (student, full-time, retired, unemployed, etc.), and/or income. In certain embodiments, the patient and/or population demographic information may include community resource information, which may include, but is not limited to, fitness facility information, pharmacy information, food bank information, grocery store information, public assistance programs, homeless shelters, etc. In embodiments, the motivation level can include the level of motivation a particular patient has for maintaining their health, which may be derived from other information (e.g., data from personal fitness tracker, indication the patient regularly visits a clinician for checkups, consumer profile information, etc.). Embodiments of the patient and/or population demographic information may include one or more data stores of demographic information which may include one or more computers or servers that facilitate the storing and retrieval of the demographic information. In some embodiments, the patient and/or population demographic information may be implemented as a cloud-based platform or may be distributed across multiple physical locations. In embodiments, the patient and/or population demographics may be obtained through any source known to one skilled in the art. For example, in certain embodiments, at least a portion of the patient and/or population demographic information may be submitted by a third party that relies on census data. In various embodiments, the patient and/or population demographic information may be obtained from more than one source. In one embodiment, the patient may submit any or all of the patient and/or population demographic information. In certain embodiments, all or a portion of the patient and/or population demographic information may be anonymized using techniques known to one skilled in the art.

In one or more embodiments, the consumer profile information may include any or all of the spending habits of one or more patients within a population. For instance, in certain embodiments, the consumer profile information may include information associated with grocery store purchases, athletic or exercise equipment purchases, restaurant purchases, and/or purchases of vitamins and/or supplements. Embodiments of the consumer profile information may include one or more data stores of consumer profile information which may include one or more computers or servers that facilitate the storing and retrieval of the consumer profile information. In some embodiments, the consumer profile information may be implemented as a cloud-based platform or may be distributed across multiple physical locations. In one embodiment, a patient may provide the consumer profile information, for example, by linking checking account and/or checking account purchase information to at least a portion of the population health management system and/or to a health insurance carrier.

The care provider information may include any information relating to a particular care provider or healthcare facility. In one embodiment, the care provider information may include information relating to the number of healthcare providers and their specialties at a particular care provider location. In the same or alternative embodiments, the care provider information may include information relating to non-personnel type resources at a particular care provider location, such as the amount and types of medications and/or the amount and types of surgical or other medical equipment. In one embodiment, the care provider information may include one or more of address and contact information, accepted payer information, status on accepting new patients, transactional systems, primary spoken language, hospital affiliations, and/or care delivery models. In embodiments, the care provider information may include information relating to the availability of any or all resources at a particular healthcare facility including personnel and/or non-personnel resources. Embodiments of the care provider information may include one or more data stores of care provider information which may include one or more computers or servers that facilitate the storing and retrieval of the care provider information. In some embodiments, the care provider information may be implemented as a cloud-based platform or may be distributed across multiple physical locations. In one embodiment, the care provider information can be provided by a healthcare provider, and/or a third party, such as an insurance provider or management entity.

Information in the output registry databases may be categorized or classified according to, for example, claims, diagnoses, wellness, satisfaction, population directories, and the like. In various embodiments, each output registry may be used by, for example, a healthcare organization to manage the health of a population segment. In one or more embodiments, each output registry may be condition specific. By way of example, a healthcare organization or clinician may manage diabetic patients within a proscribed geographic area. The condition in this example is diabetes mellitus and the output registry may help the healthcare organization manage a population segment with this condition. The output registry may, in one aspect, include identified patients within a population segment who have this condition or have risk factors that may lead to the development of diabetes, for example. The output registry may further include grouped patients within an identified segment by degree of severity or risk, such as those grouped by the grouping component of the population health server. The grouped patients in an output registry may facilitate the generation of interventions or action workflows designed to reduce disease severity or risk and to improve outcome. Additional uses for the output registries are to measure outcomes related to treatment interventions and also to attribute patients within the identified segment to appropriate healthcare providers (e.g., primary care physicians, care managers health coaches, specialists such as endocrinologists, podiatrists, and the like).

In embodiments, the plurality of EMRs may be associated with a plurality of healthcare providers, a plurality of patients, a plurality of medical conditions, a plurality of healthcare venues and/or facilities, a plurality of organizations, and/or a plurality of communities. In certain embodiments, in addition to or in place of the healthcare data, the system can receive activity data from fitness devices, demographic information, e.g., the patient and/or population demographic information; consumer information, e.g., the consumer profile information; and provider information, e.g., the care provider information.

The data processed by the system of FIG. 11 is reflective of a large population by including participants from diverse social, racial/ethnic, and ancestral populations living in a variety of geographies, social environments, and economic circumstances, and from all age groups and health statuses. One embodiment applies precision medicine treatment to many diseases, including common diseases such as diabetes, heart disease, Alzheimer's, obesity, and mental illnesses like depression, bipolar disorder, and schizophrenia, as well as rare diseases. Importantly, the system can focus on ways to increase an individual's chances of remaining healthy throughout life.

In an implementation, social network information may be maintained in a computer graph structure with nodes and edges such that each node represents a user or an organization in the network and each edge represents a known direct connection between two nodes. A number of attributes described within social networks may be stored in a database, associated with each user (also referred to herein as nodes) and strength of influence (also referred to herein as edges or distances). In some embodiments, the engine may be further configured to determine distances to one or more of the patient members closest to a current patient's biological data with a diameter of at least one grouping and to indicate that the new patient is associated with the grouping based on the comparison. In various embodiments, the engine is further configured to determine if the distance to one or more of the patient members closest to the new patient's filtered biological data is greater than a diameter of each grouping and to indicate that the new patient is not associated with each grouping based on the comparison. The medical characteristic may comprise a clinical outcome.

In one implementation, nodes may comprise attributes that include but are not limited to: a unique identifier assigned such as a user's name, address and/or other items of information; unique identifiers for the node in each external social network containing the node, statistical summaries of the node's network, and pointers to the user's medical data. In an implementation, edges of the social network may comprise attributes that include but are not limited to the unique identifiers of the two nodes that are connected by the edge, the source of the node's information (i.e. the external social network), the assigned social influence from the first node to the second node, and the assigned social influence from the second node to the first node, and statistical summaries of the edge's contribution to the network.

The above mentioned examples are not intended to be limiting, and it is intended that any medical data is included within the scope of this disclosure. In an implementation, a user may be able to designate which health provider sites or medical sites that may be desirable to obtain information from, or the sites may be automatically selected. The social health content may be presented to the user or alternatively to a health professional for assessment. For example, a user may be presented with a list of all of her medical connections from her health history sites. In such an example the user may wish to select all of the available connections, or may wish to limit the selection to only a certain number of connections. A user may be asked to assign a strength of influence (for example, a numerical value) for each of the connections received from the social networks. In an implementation, the method will receive user influence information (data) by asking the user to assign a strength of influence for a connection that represents the user's similarity to another user. Likewise, the method will receive user influence information (data) by asking the user to assign a strength of influence for a connection that represents the medical influence that any other user may have over the user herself. The strength of influence information may be recorded into memory as an influence metric. Influence metrics may be discussed in the terms of distance, even though an actual distance may not exist between the points of social data used in the method. A list of recommendations may be created for the user base on his medical neighborhood and the behavior of others within the health/medical neighborhood. For example, if influential patients of the neighborhood are using and talking about certain medication or treatment modalities, it is likely that the user may desire to apply the same medication/treatment. As such, a timely recommendation from a research would prove beneficial to both the treating professional and the patient/user.

Exemplary systems and methods for disease management are provided. In various embodiments, a method comprises identifying similar patient clusters, generating groups and interconnections of the groups, each group having one or more members that share medical similarities, each interconnection interconnecting groupings that share at least one common member, determining whether a new member shares medical similarities with the one or more members of each group and associating the new member with one or more groups. The similarities may represent similarities of measurements of gene expressions or similarities of sequencing.

The system or method described herein may be deployed in part or in whole through network infrastructures. The network infrastructure may include elements such as computing devices, servers, routers, hubs, firewalls, clients, wireless communication devices, personal computers, communication devices, routing devices, and other active and passive devices, modules or components as known in the art. The computing or non-computing device(s) associated with the network infrastructure may include, apart from other components, a storage medium such as flash memory, buffer, stack, RAM, ROM, or the like.

What is claimed is:

1. A method for rendering reality view for an object on a mobile device, a virtual reality device, or an augmented reality device, comprising:

downloading or streaming an immersive content about the object;

using the mobile device, virtual reality device, or augmented reality device with an accelerometer, performing motion tracking and area learning of an environment to provide dimension data of a physical environment to render as a virtual environment;

specifying a viewpoint for the object;

selecting a portion view of the object and blending the portion view with a pattern or color from a plurality of variations with the environment; and displaying the immersive content of the portion view and the environment based on the specified viewpoint and the position of the mobile device to span virtual and physical environments, wherein the environment is displayed using the mobile device, virtual reality device, or augmented reality device in a shared online space.

2. The method of claim 1, wherein the object comprises a person, comprising rendering the person with the viewpoint relative to the position on a smart phone, an extended, augmented or virtual reality viewer, or a portable camera.

3. The method of claim 1, comprising applying a 3D deformable template to the object and warping the template to one or more predetermined points on the object.

4. The method of claim 1, wherein the object comprises hair, foot, hand, finger, toe, wrist, neck, or ear, further comprising fabricating a jewelry.

5. The method of claim 1, comprising moving to a new view position and updating the portion view according to the new view position.

6. The method of claim 1, wherein the object comprises a body portion, a head, a chest region, a leg, further comprising providing a device or toy for the object.

7. The method of claim 1, comprising applying a hand movement to update the portion view.

8. The method of claim 1, comprising selecting a best fit from jewelry variation, shoe variations, clothing variations, apparel variations or footwear variations.

9. The method of claim 1, wherein the object comprises a face further comprising selecting one or more facial makeup products.

10. The method of claim 1, wherein the object comprises a head further comprising rendering head movements on a body portion.

11. The method of claim 1, comprising:

selecting a makeup pattern or color from a plurality of makeup product variations;

blending the makeup pattern or color onto a face model; and displaying the makeup color on the face model.

12. The method of claim 1, comprising modeling one or more applications of light foundation creme, eye disguise, highlighter, concealer or blush and recommending a makeup to the object.

13. The method of claim 4, wherein the jewelry comprises a cosmetic jewelry, a facial jewelry, a hand jewelry, a foot jewelry, an ear jewelry, a dental jewelry, a navel jewelry or a hair jewelry.

14. The method of claim 1, comprising motion tracking, area learning and depth sensing a body portion and rendering the body portion of one or more people based on the viewpoint.

15. The method of claim 1, comprising matching used jewelry or consigned jewelry to the object.

16. The method of claim 1, comprising rendering user requested model characteristic or color variations.

17. The method of claim 1, comprising providing augmented reality view or virtual reality view.

18. A method for rendering views, comprising:

selecting one or more models from a product database;

downloading or streaming an immersive content about the one or more models;

specifying a viewpoint for the one or more models;

using a mobile device, a virtual device, or an augmented reality device with an accelerometer, performing motion tracking and area learning of an environment to provide dimension data on a physical environment to render as a virtual environment;

selecting a portion view of the object and blending the portion view with a pattern or color with the environment; and displaying the one or more models and the environment based on the specified viewpoint to span virtual and physical environments and enable people to work together, wherein the environment is displayed using the mobile device, virtual reality device, or augmented reality device.

19. A method for rendering views, comprising:

selecting one or more models from a product or content database;

downloading or streaming an immersive content about the one or more models selected from the database;

using a mobile device with an accelerometer, performing motion tracking and area learning of an environment;

selecting a view of the one or more models and blending the view with a pattern or color variations with the environment; and generating an updated view based on a viewpoint and rendering one or more interactions between at least one model and the environment to span virtual and physical environments and enable people to work together, wherein the environment is displayed using the mobile device, virtual reality device, or augmented reality device.

20. The method of claim 19, comprising providing augmented reality view or virtual reality view of the one or more products with a user custom view.

* * * * *